(12) United States Patent
Wu et al.

(10) Patent No.: US 10,460,188 B2
(45) Date of Patent: Oct. 29, 2019

(54) BIO-SENSING APPARATUS

(71) Applicant: Gingy Technology Inc., Hsinchu (TW)

(72) Inventors: Jen-Chieh Wu, Pingtung (TW); Chuck Chung, Hsinchu (TW); Patrick Lin, Hsinchu (TW); Cheng-Jyun Huang, Hsinchu (TW); Kuo-Liang You, Hsinchu (TW)

(73) Assignee: Gingy Technology Inc., Hsinchu (TW)

( * ) Notice: Subject to any disclaimer, the term of this patent is extended or adjusted under 35 U.S.C. 154(b) by 0 days.

(21) Appl. No.: 16/008,037

(22) Filed: Jun. 14, 2018

(65) Prior Publication Data
US 2018/0373945 A1    Dec. 27, 2018

Related U.S. Application Data

(63) Continuation-in-part of application No. 15/713,693, filed on Sep. 24, 2017, now Pat. No. 10,043,847, (Continued)

(30) Foreign Application Priority Data

Aug. 26, 2014    (TW) .............................. 103129359 A
Dec. 22, 2014    (TW) .............................. 103144744 A
(Continued)

(51) Int. Cl.
*G06K 9/00*    (2006.01)
*A61B 5/1172*    (2016.01)
(Continued)

(52) U.S. Cl.
CPC ........ *G06K 9/00892* (2013.01); *A61B 5/1172* (2013.01); *G02B 27/0988* (2013.01);
(Continued)

(58) Field of Classification Search
CPC ............. G06K 9/00892; G06K 9/0004; G06K 9/00046; A61B 5/1172; G02B 27/0988;
(Continued)

(56) References Cited

U.S. PATENT DOCUMENTS

| | | |
|---|---|---|
| 5,177,802 A | 1/1993 | Fujimoto et al. |
| 7,361,472 B2 * | 4/2008 | Yguerabide ......... C12Q 1/6816 356/300 |

(Continued)

FOREIGN PATENT DOCUMENTS

| | | |
|---|---|---|
| JP | 2003-141514 | 5/2003 |
| TW | 200825943 | 6/2008 |
| TW | 201419165 | 5/2014 |

*Primary Examiner* — Manav Seth
(74) *Attorney, Agent, or Firm* — JCIPRNET

(57) ABSTRACT

A bio-sensing apparatus is used to sense a biopolymer. The bio-sensing apparatus includes a sensing element, a light-transmitting element and a surface plasma resonance layer. The bio-sensing apparatus is disposed on the sensing element. The surface plasma resonance layer is disposed on the light-transmitting element, and is used to receive the biopolymer. The light-transmitting element is disposed between the surface plasma resonance layer and the sensing element.

32 Claims, 49 Drawing Sheets

Related U.S. Application Data which is a continuation-in-part of application No. 15/208,619, filed on Jul. 13, 2016, now Pat. No. 9,977,947, which is a continuation-in-part of application No. 14/835,130, filed on Aug. 25, 2015, now abandoned, and a continuation-in-part of application No. 14/978,237, filed on Dec. 22, 2015, now Pat. No. 9,770,199, application No. 16/008,037, which is a continuation-in-part of application No. 15/719,575, filed on Sep. 29, 2017, which is a continuation-in-part of application No. 15/588,700, filed on May 8, 2017, said application No. 15/719,575 is a continuation-in-part of application No. 15/399,704, filed on Jan. 5, 2017, now Pat. No. 10,356,296, application No. 16/008,037, which is a continuation-in-part of application No. 15/942,386, filed on Mar. 30, 2018, now Pat. No. 10,122,899, which is a continuation-in-part of application No. 15/826,711, filed on Nov. 30, 2017, now Pat. No. 9,964,436, which is a continuation-in-part of application No. 15/239,842, filed on Aug. 18, 2016, now Pat. No. 10,049,256, application No. 16/008,037, which is a continuation-in-part of application No. 15/976,883, filed on May 11, 2018, now Pat. No. 10,091,402, which is a continuation-in-part of application No. 15/239,842, filed on Aug. 18, 2016, now Pat. No. 10,049,256, application No. 16/008,037, which is a continuation-in-part of application No. 15/989,123, filed on May 24, 2018, now Pat. No. 10,181,069, which is a continuation-in-part of application No. 15/239,842, filed on Aug. 18, 2016, now Pat. No. 10,049,256, application No. 16/008,037, which is a continuation-in-part of application No. 15/956,875, filed on Apr. 19, 2018, which is a continuation-in-part of application No. 15/588,700, filed on May 8, 2017, said application No. 15/956,875 is a continuation-in-part of application No. 15/399,704, filed on Jan. 5, 2017, now Pat. No. 10,356,296, said application No. 15/956,875 is a continuation-in-part of application No. 15/719,575, filed on Sep. 29, 2017, application No. 16/008,037, which is a continuation-in-part of application No. 16/004,459, filed on Jun. 11, 2018, now abandoned, which is a continuation-in-part of application No. 15/239,842, filed on Aug. 18, 2016, now Pat. No. 10,049,256.

(60) Provisional application No. 62/486,954, filed on Apr. 18, 2017, provisional application No. 62/371,230, filed on Aug. 5, 2016, provisional application No. 62/413,974, filed on Oct. 27, 2016, provisional application No. 62/266,002, filed on Dec. 11, 2015, provisional application No. 62/533,632, filed on Jul. 17, 2017, provisional application No. 62/563,045, filed on Sep. 25, 2017, provisional application No. 62/574,222, filed on Oct. 19, 2017, provisional application No. 62/620,985, filed on Jan. 23, 2018.

(30) Foreign Application Priority Data

| Jul. 18, 2016 | (TW) | 105122567 A |
|---|---|---|
| Sep. 26, 2016 | (TW) | 105214737 U |
| Nov. 4, 2016 | (TW) | 105135846 A |
| Mar. 17, 2017 | (CN) | 2017 2 0260844 U |
| Jun. 29, 2017 | (TW) | 106121692 A |
| Jul. 25, 2017 | (CN) | 2017 1 0612541 |
| Aug. 8, 2017 | (TW) | 106126793 A |
| Sep. 20, 2017 | (CN) | 2017 1 0852899 |
| Dec. 5, 2017 | (CN) | 2017 1 1271306 |
| Jan. 7, 2018 | (CN) | 2018 2 0021470 U |
| Mar. 1, 2018 | (CN) | 2018 2 0286719 U |
| Apr. 24, 2018 | (CN) | 2018 2 0588432 U |

(51) Int. Cl.
  *G02B 27/09* (2006.01)
  *H01L 27/146* (2006.01)

(52) U.S. Cl.
  CPC ....... *G06K 9/0004* (2013.01); *G06K 9/00046* (2013.01); *H01L 27/14623* (2013.01); *H01L 27/14627* (2013.01); *H01L 27/14629* (2013.01); *H01L 27/14678* (2013.01)

(58) Field of Classification Search
  CPC ......... H01L 27/14627; H01L 27/14629; H01L 27/14678; H01L 27/14623
  See application file for complete search history.

(56) References Cited

U.S. PATENT DOCUMENTS

| 7,847,948 | B2* | 12/2010 | Lee | G06K 9/0004 |
|---|---|---|---|---|
| | | | | 356/326 |
| 8,391,569 | B2 | 3/2013 | Wu | |
| 8,649,001 | B2* | 2/2014 | Wu | G06K 9/00046 |
| | | | | 356/71 |
| 9,064,768 | B2* | 6/2015 | Ishiguro | A61B 5/1455 |
| 9,159,760 | B2* | 10/2015 | Ootsuka | H04N 5/335 |
| 9,811,710 | B2* | 11/2017 | Gao | G06K 9/0004 |
| 9,811,711 | B2* | 11/2017 | Huang | G02B 5/20 |
| 9,829,614 | B2* | 11/2017 | Smith | G02B 27/58 |
| 9,892,303 | B2* | 2/2018 | Li | G06K 9/0004 |
| 9,964,436 | B1* | 5/2018 | Chung | G01J 1/0437 |
| 10,102,411 | B2* | 10/2018 | Lillie | G06K 9/0002 |
| 10,169,630 | B2* | 1/2019 | Fomani | G01J 1/0214 |
| 10,176,355 | B2* | 1/2019 | Smith | G06K 9/0008 |
| 10,181,070 | B2* | 1/2019 | Smith | G02B 5/005 |
| 10,268,884 | B2* | 4/2019 | Jones | G06K 9/0053 |
| 2003/0096302 | A1* | 5/2003 | Yguerabide | C12Q 1/6816 |
| | | | | 435/7.1 |
| 2005/0117157 | A1* | 6/2005 | Tarsa | G01N 21/39 |
| | | | | 356/437 |
| 2006/0034729 | A1* | 2/2006 | Poponin | G01N 21/658 |
| | | | | 422/82.05 |
| 2006/0119837 | A1* | 6/2006 | Raguin | G06K 9/00046 |
| | | | | 356/71 |
| 2008/0131939 | A1* | 6/2008 | Roper | C12Q 1/686 |
| | | | | 435/91.2 |
| 2009/0015831 | A1* | 1/2009 | Yguerabide | C12Q 1/6816 |
| | | | | 356/337 |
| 2013/0050123 | A1 | 2/2013 | Lien et al. | |
| 2014/0307258 | A1* | 10/2014 | Kirkbride | A61B 5/0075 |
| | | | | 356/300 |
| 2016/0013234 | A1* | 1/2016 | Ootsuka | H04N 5/335 |
| | | | | 257/432 |
| 2016/0117543 | A1 | 4/2016 | Huang et al. | |
| 2016/0132712 | A1* | 5/2016 | Yang | G06K 9/0002 |
| | | | | 348/77 |
| 2016/0224816 | A1 | 8/2016 | Smith et al. | |
| 2017/0212358 | A1 | 7/2017 | Fan et al. | |
| 2017/0317128 | A1* | 11/2017 | Ootsuka | H04N 5/335 |

* cited by examiner

BIO-SENSING APPARATUS

BACKGROUND OF THE INVENTION

Field of the Invention

The disclosure relates to a sensing apparatus, and particularly relates to a bio-sensing apparatus.

Description of Related Art

In a conventional identity recognition technique, a biological feature is, for example, implemented by pressing ink by a finger for transferring to a paper to form a fingerprint pattern, and then inputting the fingerprint pattern into a computer through optical scanning to establish a file or implement comparison. The above identity recognition method has a disadvantage of none real-time processing, and cannot satisfy the demand for real-time identity recognition in today's society. Therefore, electronic biological feature identification elements become a main stream of technologies development. However, a biological feature identification element has only a function of a biological feature identification generally. Therefore, a development direction is that functions of the biological feature identification element should be added so as to increase an additional value of the biological feature identification element.

SUMMARY OF THE INVENTION

The invention provides a bio-sensing apparatus able to sense biopolymers.

A bio-sensing apparatus of an embodiment of the invention includes a sensing element, a spatial filter element, a light-transmitting element and a surface plasma resonance layer. The sensing element has a sensing surface, and the spatial filter element has spatial filter sheets. Each of the spatial filter sheets includes a light-transmitting layer and a spatial filter layer disposed on the light-transmitting layer. The spatial filter layer has light-transmitting portions and light-blocking portions. Each of the light-transmitting portions is surrounded by light-blocking portions of the light-blocking portions. Light-transmitting layers of the spatial filter sheets and spatial filter layers of the spatial filter sheets are stacked alternately in a normal direction of the sensing surface. The light-transmitting element disposed on the spatial filter element. The spatial filter element is disposed between the light-transmitting element and the sensing element. The surface plasma resonance layer is disposed on the light-transmitting element and adapted to receive the biopolymer. The light-transmitting element is disposed between the surface plasma resonance layer and the spatial filter element.

A bio-sensing apparatus of an embodiment of the invention includes a light guide, a first reflection device, a sensing element, a light-transmitting element and a surface plasma resonance layer. The light guide has a top surface and a bottom surface opposite to the top surface. The first reflection device is disposed on a bottom surface of the light guide. The sensing element is disposed beside the bottom surface of the light guide. The light-emitting element is used to emit a light beam. The light beam is reflected by the first reflection device so as to be transmitted to the sensing element. The surface plasma resonance layer is disposed on the light guide and adapted to receive biopolymers. The light guide is located between the surface plasma resonance layer and the sensing element.

Based on the foregoing, the bio-sensing apparatus according to an embodiment of the invention has multiple functions of biometric identification and biological detection, and an additional value of the bio-sensing apparatus is high.

To make the aforementioned and other features and advantages of the invention more comprehensible, several embodiments accompanied with drawings are described in detail as follows.

DESCRIPTION OF THE EMBODIMENTS

Figure 1:
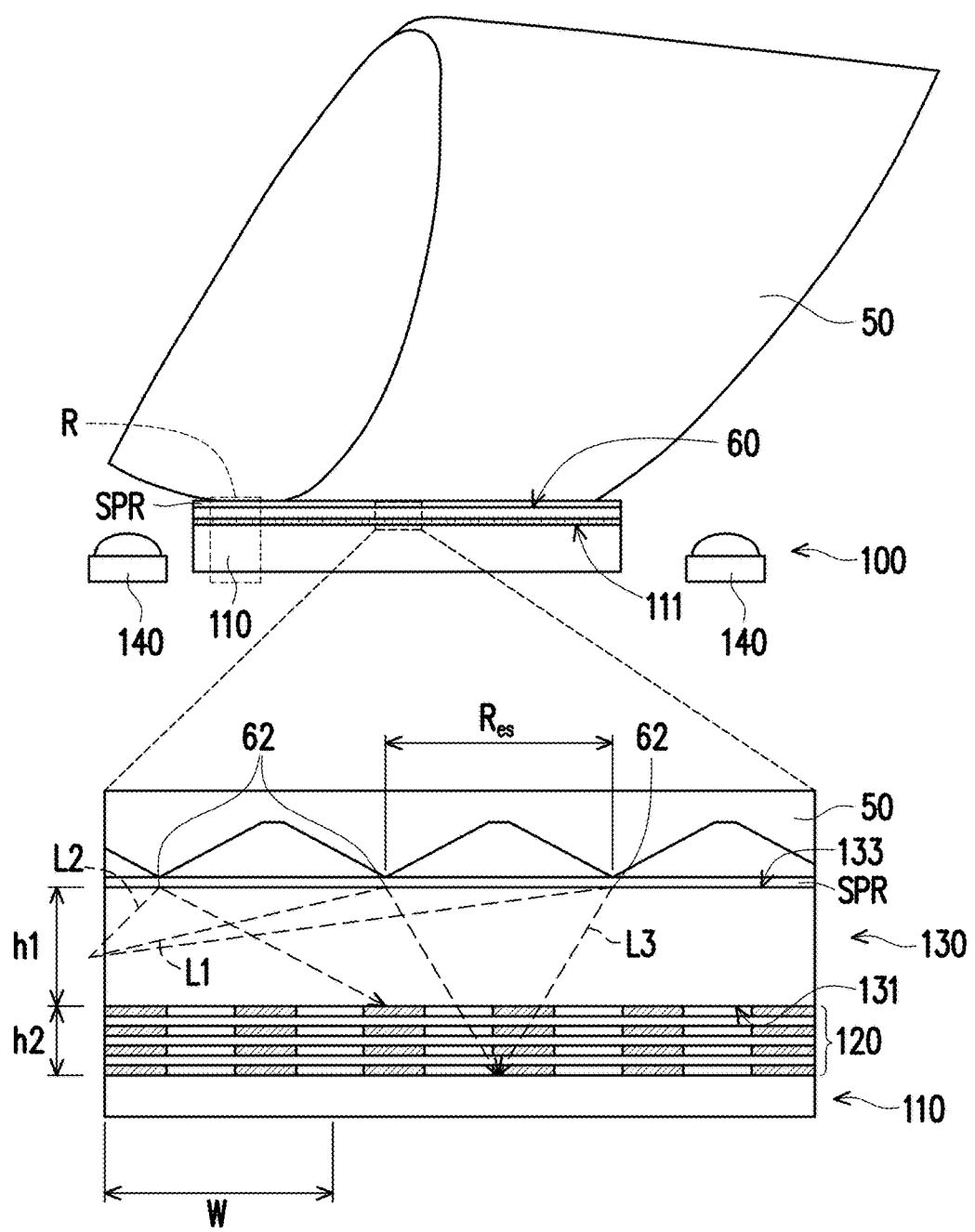
FIG. 1 is a schematic diagram and a partially enlarged view of a bio-sensing apparatus according to an embodiment of the invention.

In the following detailed description of each of embodiments, reference is made to the accompanying drawings which form a part hereof, and in which are shown by way of illustration specific embodiments in which the invention may be practiced. In this regard, directional terminology, such as "top," "bottom," "front," "back," "left," "right," etc., is used with reference to the orientation of the Figure(s) being described. As such, the directional terminology is used for purposes of illustration and is in no way limiting. Moreover, in any one of embodiments, the same or similar reference numerals denote the same or similar components.

FIG. 1 is a schematic diagram and a partially enlarged view of a bio-sensing apparatus according to a first embodiment of the invention. Referring to FIG. 1, the bio-sensing apparatus 100 is adapted to sense a fingerprint 60 of a finger of a user 50, and the bio-sensing apparatus 100 includes a sensing element 110, a light-transmitting element 130 and a spatial filter element 120 disposed between the light-transmitting element 130 and the sensing element 110. The sensing element 110 includes a sensing surface 111, and the spatial filter element 120 is disposed on the sensing surface 111. In other words, in the bio-sensing apparatus 100 of the present exemplary embodiment, a light is adapted to be transmitted from the light-transmitting element 130 to the sensing element 110, and the light has to pass through the spatial filter element 120 before being transmitted to the sensing element 110.

The spatial filter element 120 of the present exemplary embodiment includes a plurality of light-blocking portions 122 and a plurality of light-transmitting portions 124, and each of the light-transmitting portions 124 is surrounded by a part of the light-blocking portions 122, i.e. each of the light-transmitting portions 124 is surrounded by a plurality of light-blocking portions 122. The light-transmitting element 130 of the present embodiment is disposed on the spatial filter element 120, and the light-transmitting element 130 is adapted to contact the finger of the user 50, and the fingerprint 60 of the user 50 can be pressed on the light-transmitting element 130.

The light-transmitting element 130 of the present embodiment is adapted to transmit sensing lights L1, L2 and L3 from the finger of the user 50 to the spatial filter element 120, and the light-blocking portions 122 of the spatial filter element 120 are adapted to block a portion of the sensing lights (for example, the sensing light L2), and another portion of the sensing lights (for example, the sensing lights L1, L3) is transmitted to the sensing surface 111 through the light-transmitting portions 124.

In the bio-sensing apparatus 100 of the present embodiment, since each of the light-transmitting portions 124 of the spatial filter element 120 is surrounded by the light-blocking portions 122, the light-blocking portions 122 surrounding the light-transmitting portion 124 may control the sensing light received by a part of the sensing surface 111 under the light-transmitting portion 124 surrounded by the light-blocking portions 122, and prevent scattered lights coming from other places of the fingerprint 60 from being transmitted to the part of sensing surface 111 under the aforementioned light-transmitting portion 124. In other words, if the incident angle of the sensing light propagates to the spatial filter element 120 of the present embodiment is too large, the light-blocking portions 122 of the spatial filter element 120 may block the above sensing light with large incident angle, such that the sensing element 110 may accurately receive images coming from different positions of the fingerprint 60, and sensing accuracy of the bio-sensing apparatus 100 is improved. Further, the fingerprint 60 of the user 50 has a plurality of peaks 62, and the bio-sensing apparatus 100 of the present embodiment allows the sensing surface 111 under each of the light-transmitting portions 124 to receive the sensing lights $L_1$, $L_3$ coming from less than two peaks 62 of the fingerprint 60, such that the sensing element 110 may sense one fingerprint image or fingerprint information that is easy to be recognized.

To be specific, referring to the enlarged view of FIG. 1, the sensing element 110 of the present embodiment includes a plurality of sensing units 112, where the sensing units 112 are arranged on the sensing surface 111, and each of the light-transmitting portions 124 corresponds to one of the sensing units 112. In other words, the light-transmitting portions 124 of the present embodiment cover the sensing units 112, and the sensing units 112 may receive the sensing light through the light-transmitting portions 124. On the other hand, the light-blocking portions 122 may prevent the sensing units 112 from receiving the sensing lights coming from the fingerprint 60 located at a farther area, so as to ensure that the sensing units 112 may receive the sensing lights coming from the fingerprint 60 located at an adjacent area right above the sensing unit 112, and the bio-sensing apparatus 100 may accurately sense an image signal of the fingerprint 60 of the user 50.

Referring to FIG. 1, in detail, the bio-sensing apparatus 100 of the present embodiment further includes a light-emitting unit 140, and the light-emitting unit 140 is adapted to send the sensing light to a surface (i.e. the fingerprint 60) of the finger of the user 50. The light-emitting unit 140 of the present embodiment is, for example, adapted to send the sensing light with a wavelength in a visible light spectrum or an invisible light spectrum to the fingerprint 60 of the user 50, and the sensing element 110 is adapted to receive lights with a wavelength the same or similar to that of the sensing light.

Further, the light-blocking portions 122 of the spatial filter element 120 of the present embodiment are adapted to absorb the sensing light, i.e. the light-blocking portions 122 are adapted to absorb lights with a wavelength the same or similar to that of the sensing light, such that the bio-sensing apparatus 100 may provide accurate fingerprint sensing. Moreover, the spatial filter element 120 of the present application may be formed by a collimator, micro-structures, optical fibers, an optical grating etc., but the application is not limited thereto.

To be specific, the sensing element 110 of the present embodiment is, for example, an image sensor such as a charge-coupled device (CCD) or a complementary metal-oxide semiconductor (CMOS), and the sensing units 112 are, for example, sensing pixels on the image sensor, though the invention is not limited thereto. In other embodiments, the sensing units 112 can be closely arranged on the sensing surface 111 covered by the spatial filter element 120, i.e. the spatial filter element 120 of the present embodiment can be used in collaboration with various image sensors to provide a good fingerprint sensing effect.

Figure 2:
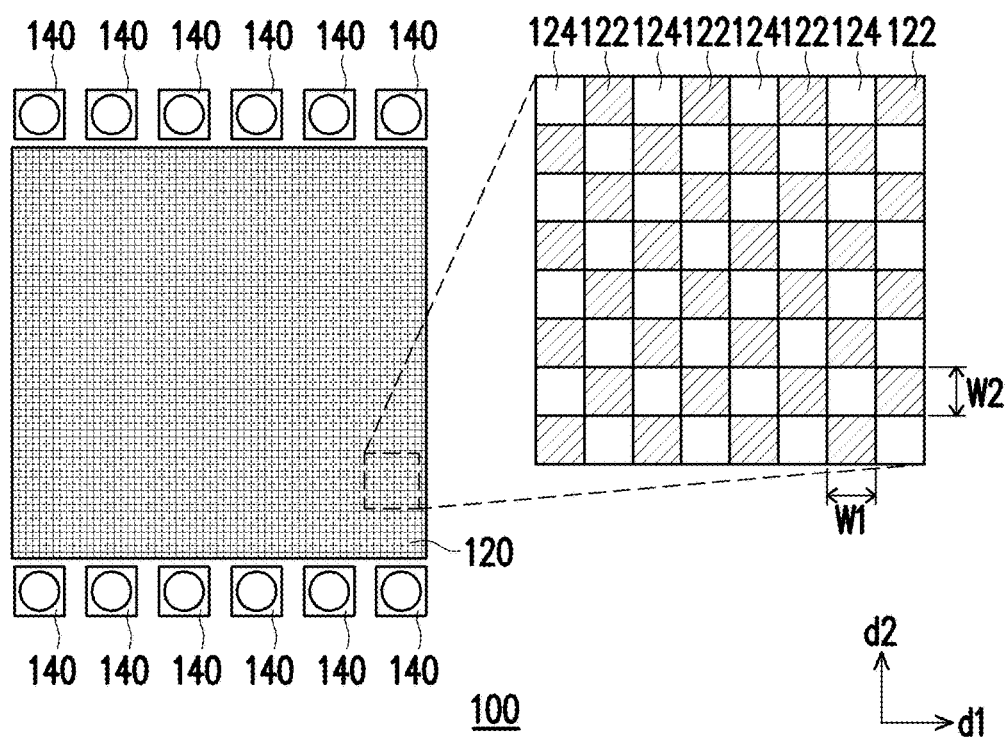
FIG. 2 is a top view of a bio-sensing apparatus according to an embodiment of the invention.

FIG. 2 is a top view of a bio-sensing apparatus according to the first embodiment of the invention. In order to clearly describe positions and relative relations of various components of the present embodiment, the light-transmitting element of the bio-sensing apparatus is omitted. Referring to FIG. 2, in the first embodiment of the invention, the light-blocking portions 122 and the light-transmitting portions 124 of the spatial filter element 120 are arranged in alternation on the sensing surface 111 along a first direction d1 and a second direction d2, where the first direction d1 is perpendicular to the second direction d2, and the first direction d1 and the second direction d2 are all perpendicular to a normal of the sensing surface 111. In other words, each of the light-transmitting portions 124 of the present embodiment is located between two light-blocking portions 122 in the first direction d1, and each of the light-transmitting portions 124 is located between two light-blocking portions 122 in the second direction d2, so that the light-blocking portions 122 and the light-transmitting portions 124 are arranged in a chessboard-type manner. Since each of the light-transmitting portions 124 of the spatial filter element 120 is surrounded by four light-blocking portions 122, the sensing light can be more accurately transmitted to the sensing surface 110 from the fingerprint 60, so as to provide a good fingerprint sensing effect.

Referring to FIG. 2, the light-emitting units 140 of the present embodiment are, for example, disposed at two sides of the spatial filter element 120, the light-transmitting element 130 and the sensing element 110, though the invention is not limited thereto. In other embodiments, the light-emitting units 140 can be further disposed at corners, periphery or a combination thereof around the spatial filter element 120, the light-transmitting element 130 and the sensing element 110.

On the other hand, a refractive index of a material of the light-transmitting element 130 is the same to a refractive index of a material of the light-transmitting portions 124 of the spatial filter element 120, so that the light-transmitting portions 124 may provide a good optical transmitting effect between the spatial filter element 120 and the sensing element 110.

Referring to FIG. 2, a width W1 of the light-transmitting portion 124 in the first direction d1 is smaller than or equal to a width of the sensing unit 112 in the first direction d1, and a width W2 of the light-transmitting portion 124 in the second direction d2 is smaller than or equal to a width of the sensing unit 112 in the second direction d2. Referring to FIG. 1, the spatial filter element 120 of the bio-sensing apparatus 100 of the present embodiment can be perfectly matched with a width of the fingerprint 60 of the user 50. Further, a pitch between two adjacent light-blocking regions 122 is substantially the same with a distance $R_{es}$ of the sensing units 112 of sensing element 110 to be resolved (i.e. a width between two adjacent peaks in the fingerprint to be sensed), and the bio-sensing apparatus 100 of the present embodiment is complied with $$h_2 \geq \frac{h_1 W}{R_{es} - W},$$

where $h_1$ is a height of the light-transmitting element 130 along a direction parallel to the normal of the sensing surface 111, and $h_2$ is a height of the spatial filter element 120 along the direction parallel to the normal of the sensing surface 111, and W is the minimum width of each of the light-transmitting portions 124 along a direction perpendicular to the normal of the sensing surface 111. Therefore, the light-blocking portions 122 of the spatial filter element 120 may provide a good light-blocking effect, so as to prevent the scattered light with a large angle to form a noise, and accordingly improve the sensing accuracy of the bio-sensing apparatus 100.

On the other hand, the spatial filter element 120 of the present embodiment is complied with $$\frac{h_1}{2} \leq h_2 \leq h_1,$$

where $h_1$ and $h_2$ are respectively heights of the light-transmitting element 110 and the spatial filter element 120 along the direction parallel to the normal of the sensing surface 111. Therefore, the size of the light-transmitting portions 124 in the spatial filter element 120 of the bio-sensing apparatus 100 can be perfectly matched with the width of the fingerprint 60 to be detected, so as to provide a good fingerprint detecting effect.

Referring to FIG. 1, in the present embodiment, the light-transmitting element 130 further includes a connection surface 131 and a contact surface 133. The contact surface 133 is adapted to contact the finger of the user 50, and the connection surface 131 is connected to the spatial filter element 120, the spatial filter element 120 is connected to the sensing surface 111 of the sensing element 110, and the contact surface 133, the connection surface 131 and the sensing surface 111 are parallel to each other. Therefore, the light-blocking portions 122 and the light-transmitting portions 124 of the spatial filter element 120 are arranged in alternation between the sensing surface 111 and the connection surface 131 along the direction perpendicular to the normal of the sensing surface 111, so that the sensing light sensed by the sensing surface 111 may accurately correspond to the fingerprint 60 on the contact surface 133.

Figure 3:
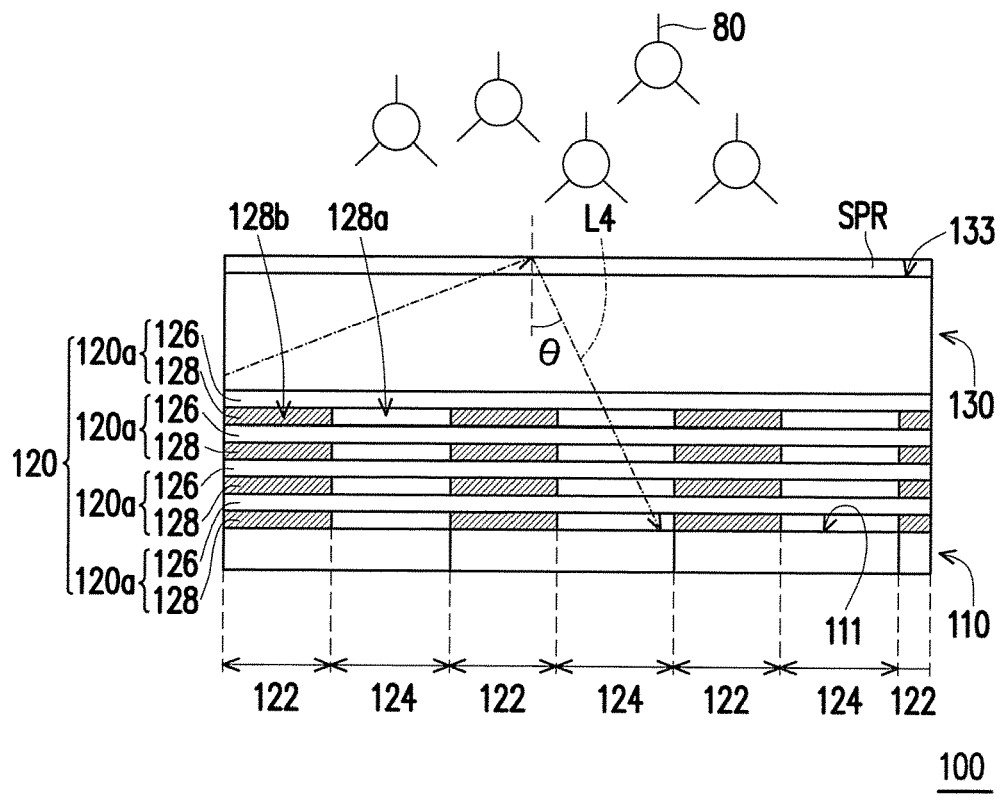
FIG. 3 is a partial enlarged view of a part R of the bio-sensing apparatus of FIG. 1.

FIG. 3 is a partial enlarged view of a part R of the bio-sensing apparatus of FIG. 1. Referring to FIG. 1 and FIG. 3, the spatial filter element 120 of the present embodiment includes spatial filter sheet 120a. Each of the spatial filter sheet 120a includes a light-transmitting layer 126 and a spatial filter layer 128 disposed on the light-transmitting layer 126. The spatial filter layer 128 includes a plurality of light-transmitting portions 128a and a plurality of light-blocking portions 128b. Each of the transmitting portions 128a is surrounded by the light-blocking portions 128b. The spatial filter layer 128 may be referred as a light shielding layer has a specific pattern, the light-blocking portions 128b may be referred as light shielding material portions of the light shielding layer, and the light-transmitting portions 128a may be referred as light-transmitting opening of the light shielding layer. Light-transmitting layers 126 of the spatial filter sheet 120a and spatial filter layers 128 of the spatial filter sheet 120a are alternately stacked in a normal direction N of sensing surface 111. Light-blocking portions 128b of the spatial filter layers 128 of the spatial filter sheet 120a define light-blocking portions 122 of the spatial filter element 120. Light-transmitting portions 128a of the spatial filter layers 128 of the spatial filter sheet 120a define light-transmitting portions 124 of the spatial filter element 120.

Referring to FIG. 1 and FIG. 3, it should be noted that the bio-sensing apparatus 100 of the present embodiment further includes a surface plasma resonance layer SPR. The surface plasma resonance layer SPR is disposed on a surface 133 of the light-transmitting element 130. The light-transmitting element 130 is disposed between the surface plasma resonance layer SPR and the spatial filter element 120. In the present embodiment, for example, a material of the surface plasma resonance layer SPR includes a metal, a thinness of the surface plasma resonance layer SPR is approximately 50 nm, but the invention is not limited thereto.

The surface plasma resonance layer SPR is used to receive biopolymers 80, the biopolymers 80 may be sweat, blood, urine, bacteria, viruses etc., but the invention is not limited thereto. At least one light-emitting unit 140 is used to emit a sensing light L4 toward the surface plasma resonance layer SPR. The sensing light L4 reflected by the surface plasma resonance layer SPR has reflection angles θ.

When the biopolymers 80 are formed on the surface plasma resonance layer SPR, reflectivity of a portion of the sensing light L4 having a specific reflection angle (i.e. a resonance angle) of the reflection angles θ is greatly reduced. The sensing element 100 receives the sensing light L4 reflected by the surface plasma resonance layer SPR and having the reflection angles θ. The specific reflection angle (i.e. a resonance angle) can be determined by analyzing a light distribution of the sensing light L4 received by the sensing element 100. The biopolymers 80 disposed on the surface plasma resonance layer SPR can be identified by the specific reflection angle. In the following below, more details accompanied with FIG. 4 are provided.

Figure 4:
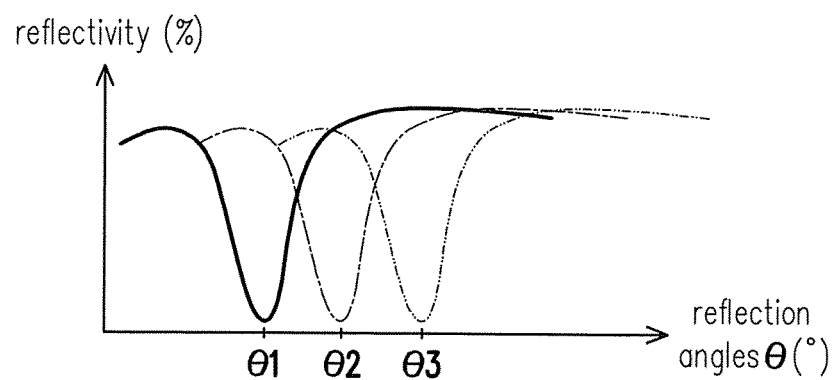
FIG. 4 shows the relationship between reflection angles θ of the sensing light L4 reflected by the surface plasma resonance layer SPR and its reflectivity.

FIG. 4 shows the relationship between reflection angles θ of the sensing light L4 reflected by the surface plasma resonance layer SPR and its reflectivity. Referring to FIG. 3 and FIG. 4, for example, when first type biopolymers 80 are formed on the surface plasma resonance layer SPR, reflectivity of a portion of the sensing light L4 having a specific reflection angle θ1 of the reflection angles θ is greatly reduced, the specific reflection angle θ1 can be determined by analyzing a light distribution of the sensing light L4 having the reflection angles θ and received by the sensing element 100, and the first type biopolymers 80 disposed on the surface plasma resonance layer SPR can be identified by the specific reflection angle θ1. When second type biopolymers 80 are formed on the surface plasma resonance layer SPR, reflectivity of a portion of the sensing light L4 having a specific reflection angle θ2 of the reflection angles θ is greatly reduced, the specific reflection angle θ2 can be determined by analyzing a light distribution of the sensing light L4 having the reflection angles θ and received by the sensing element 100, and the second type biopolymers 80 disposed on the surface plasma resonance layer SPR can be identified by the specific reflection angle θ2. When third type biopolymers 80 are formed on the surface plasma resonance layer SPR, reflectivity of a portion of the sensing light L4 having a specific reflection angle θ3 of the reflection angles θ is greatly reduced, the specific reflection angle θ3 can be determined by analyzing a light distribution of the sensing light L4 having the reflection angles θ and received by the sensing element 100, and the third type biopolymers 80 disposed on the surface plasma resonance layer SPR can be identified by the specific reflection angle θ3.

Figure 5:
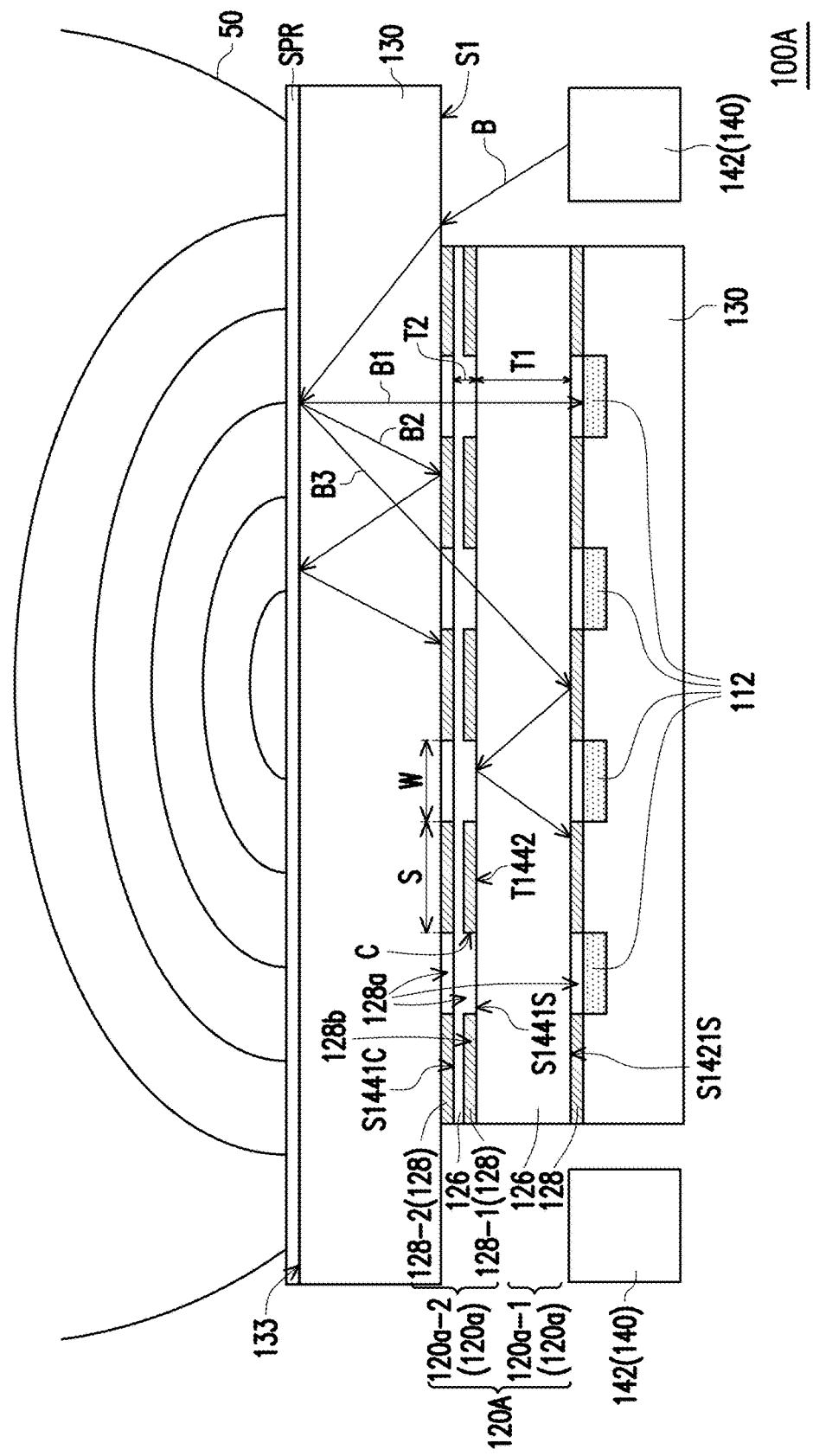
FIG. 5 is a sectional view of a bio-sensing apparatus according to a first exemplary embodiment of the invention
Figure 6:
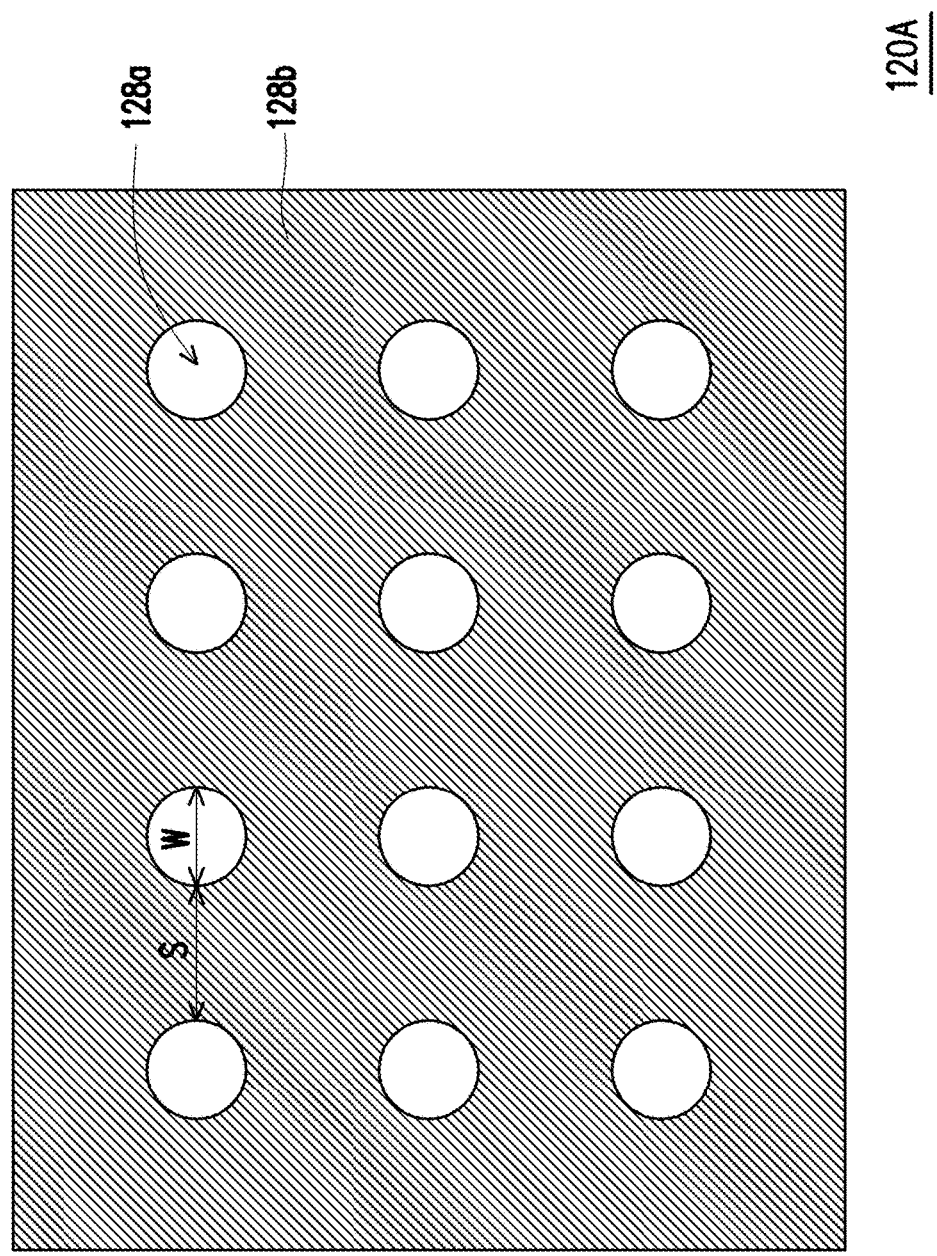
FIG. 6 is a top view of a spatial filter element illustrated in FIG. 5.

FIG. 5 is a sectional view of a bio-sensing apparatus according to a first exemplary embodiment of the invention. FIG. 6 is a top view of a spatial filter element illustrated in FIG. 5. Referring to FIGS. 5 and 6, a bio-sensing apparatus 100A according to the first exemplary embodiment of the invention is adapted to capture the biological characteristics of a user 50 to be identified. For example, the biological characteristics may be fingerprints or veins, but the invention is not limited thereto.

The bio-sensing apparatus 100A includes a light-transmitting element 130, a light-emitting element 140, a sensing element 110 and a spatial filter element 120A. The sensing element 110 is disposed beside the light-emitting element 140. The light-emitting element 140 and the sensing element 110 are on the same side of the light-transmitting element 130. The spatial filter element 120A is disposed between the light-transmitting element 130 and the sensing element 110 and may be fixed between the light-transmitting element 130 and the sensing element 110 through an adhesion layer (not illustrated) or a fixing mechanism (not illustrated).

The light-transmitting element 130 is adapted to protect elements disposed below, and the light-transmitting element 130 may be a glass substrate or a plastic substrate. The glass substrate may be chemically or physically strengthened or not strengthened at all. The plastic substrate may be made from polycarbonate (PC), polyethylene terephthalate (PET), polymethylmethacrylate (PMMA), or polyimide (PI) or the like, but is not limited thereto.

The light-transmitting element 130 includes an inner surface SI and a surface 133 that is opposite to the inner surface SI. The inner surface SI of the light-transmitting element 130 is a surface of the light-transmitting element 130 facing toward the sensing element 110, and the surface 133 of the light-transmitting element 130 is a contact surface of the user 50. In other words, the user 50 contacts the surface 133 of the light-transmitting element 130 to identify the biological characteristics.

The light-emitting element 140 is adapted to provide a light beam B radiating the user 50. The light-emitting element 140 may include a plurality of light emitting elements 142. Each of the light emitting elements 142 emits the light beam B toward the user 50. The light emitting elements 142 may include a light emitting diode, a laser diode or a combination thereof. Besides, the light beam B may include visible light, invisible light or a combination thereof. Invisible light may be infrared light, but is not limited thereto.

The sensing element 110 is adapted to receive a portion of the light beam B reflected by the user 50 (i.e. a light beam B1 with information on fingerprint patterns). In one exemplary embodiment of the invention, the sensing element 110 may be integrated with a pulse-width modulation circuit. The pulse-width modulation circuit controls light emitting time of the light emitting elements 142 and image capturing time of the sensing element 110, so that the light emitting time of the light emitting elements 142 is synchronized with image capturing time of the sensing element 110 to achieve accurate control, but the exemplary embodiment is not limited thereto.

The spatial filter element 120A is adapted to collimate the portion of the light beam B that is reflected by the user 50 and transmitted toward the sensing element 110. The spatial filter element 120A includes a plurality of spatial filter sheets 120a overlapping with each other. In the exemplary embodiment, the spatial filter element 120A includes two spatial filter sheets 120a, i.e. a first spatial filter sheet 120a-1 and a second spatial filter sheet 120a-2, and the first spatial filter sheet 120a-1 is disposed between the second spatial filter sheet 120a-2 and the sensing element 100. However, for the spatial filter element 120A, the number of the spatial filter sheets and the relative location relationship between the spatial filter sheets may vary based on demand, and are not limited to what is illustrated in FIG. 5.

Each of the spatial filter sheets includes a light-transmitting layer 126 and a spatial filter layer 128 disposed on the light-transmitting layer 126. For instance, the first spatial filter sheet 120a-1 includes a light-transmitting layer 126 and a spatial filter layer 128 that is disposed on a surface S1421S of the light-transmitting layer 126 facing toward the sensing element 110 and located between the light-transmitting layer 126 and the sensing element 110. The second spatial filter sheet 120a-2 includes a light-transmitting layer 126, a spatial filter layer 128-1 and a spatial filter layer 128-2, wherein the spatial filter layer 128-1 is disposed on a surface S1441S of the light-transmitting layer 126 facing toward the sensing element 110 and located between the light-transmitting layer 126 of the first spatial filter sheet 120a-1 and the light-transmitting layer 126 of the second spatial filter sheet 120a-2, and the spatial filter layer 128-2 is disposed on a surface S1441C of the light-transmitting layer 126 facing toward the light-transmitting element 130 and located between the light-transmitting element 130 and the light-transmitting layer 126 of the second spatial filter sheet 120a-2.

For each of the spatial filter sheets 120a, the numbers of the light-transmitting layers 126 and the spatial filter layers 128, the relative location relationship between the light-transmitting layer 126 and the spatial filter layer 128 and a method of forming the spatial filter layer 128 can vary based on demand, but are not limited to what is illustrated in FIG. 5. A plurality of indentations C are formed on the surface S1441S of the light-transmitting layer 126, and the spatial filter layer 128 is disposed in the indentations C of the light-transmitting layer 126, allowing an outer surface T1442 of the spatial filter layer 128 to line up with a portion of the surface S1441S without the indentations C. The method of forming the spatial filter layer 128 may include the following steps: Firstly, the indentations C are formed on the surface S1441S of the light-transmitting layer 126; secondly, light absorbing materials are formed in the indentations C; and afterwards, the spatial filter layer 128 is formed by curing the light absorbing materials. In one exemplary embodiment, the light-transmitting layer 126 and the indentations C may be formed through mold casting with the formation of the indentations C omitted.

In each of the spatial filter sheets 120a, the light-transmitting layers 126 provide bearing surfaces for the spatial filter layers 128, and the light-transmitting layers may be glass substrates or plastic substrates. The spatial filter layers 128 are configured to absorb large-angle light beams (such as a light beam B2 or a light beam B3) of the light beam B that are reflected by the user 50 to collimate the light beams transmitted to the sensing element 110. The spatial filter layer 128 exhibits high absorptance and low reflectance to reduce the proportion of the light beams that are transmitted to and reflected by the spatial filter layer 128 and the frequency of the light beams reflected by the spatial filter layer 128, further effectively reducing the proportion of the large-angle light beams received by the sensing element 110. The low reflectance means the reflectance is less than 10% in visible and infrared bands. For instance, the spatial filter layer 128 may be made from ink with low reflectance, but is not limited thereto.

In addition, in order to allowed the portion of the light beam B that is reflected by the user 50 (such as the light beam B1) to be received by the sensing element 110, the spatial filter layer includes a plurality of light-transmitting portions 128a. The light-transmitting portions 128a expose a plurality of sensing units 112 of the sensing element 110. Specifically, the light-transmitting portions 128a of the spatial filter layer 128 are disposed relative to the sensing units 112 of the sensing element 110.

Spacing between the light-transmitting portions 128a is S. A width of each of the light-transmitting portions 128a is W, and 0.3 W<S. A light-transmitting layer 126 thickness of the first spatial filter sheet 120a-1 is T1, a light-transmitting layer 126 thickness of the second spatial filter sheet 144 is T2, and the bio-sensing apparatus 100 satisfies:

$$0.3 \times \frac{W}{S} \times T1 \le T2 \le T1.$$

The light-transmitting layer 126 thickness of the spatial filter sheet 120a refers to a total thickness of all the light-transmitting layers 126 in the spatial filter sheet 120a. In the exemplary embodiment, the first spatial filter sheet 120a-1 includes only one light-transmitting layer, and the second spatial filter sheet 120a-2 includes only one light-transmitting layer. Therefore, the light-transmitting layer thickness T1 of the first spatial filter sheet 120a-1 is a thickness of the light-transmitting layer 126, and the light-transmitting layer thickness T2 of the second spatial filter sheet 120a-2 is a thickness of the light-transmitting layer 126, but not limited thereto.

Under the design of $$0.3 \times \frac{W}{S} \times T1 \le T2 \le T1,$$

the large-angle light beams (i.e. the light beam B2 and the light beam B3) are reflected several times between the spatial filter sheets 120a and absorbed by the spatial filter layer 128 to effectively address the problem of crosstalk and enable the bio-sensing apparatus 100A to have a good identification capability. In one exemplary embodiment, if the bio-sensing apparatus 100A satisfies the condition $$0.3 \times \frac{W}{S} \times T1 \le T2 \le 0.9 \times \frac{W}{S} \times T1,$$

the proportion of the large-angle light beams received by the sensing element 110 may be further reduced, and a signal-to-noise ratio increases effectively to help a back end recognize a signal and noise, and thus raise possibilities of successful identification. In another exemplary embodiment, if the bio-sensing apparatus 100A satisfies the condition $$0.9 \times \frac{W}{S} \times T1 \le T2 \le T1,$$

the signal-to-noise ratio may be close to 0.

Referring to FIG. 5, the bio-sensing apparatus 100A further includes a surface plasma resonance layer SPR. A function of the surface plasma resonance layer SPR of the bio-sensing apparatus 100A and a function of the surface plasma resonance layer SPR of the above bio-sensing apparatus 100 are the same, and which will not be repeated here.

Figure 7:
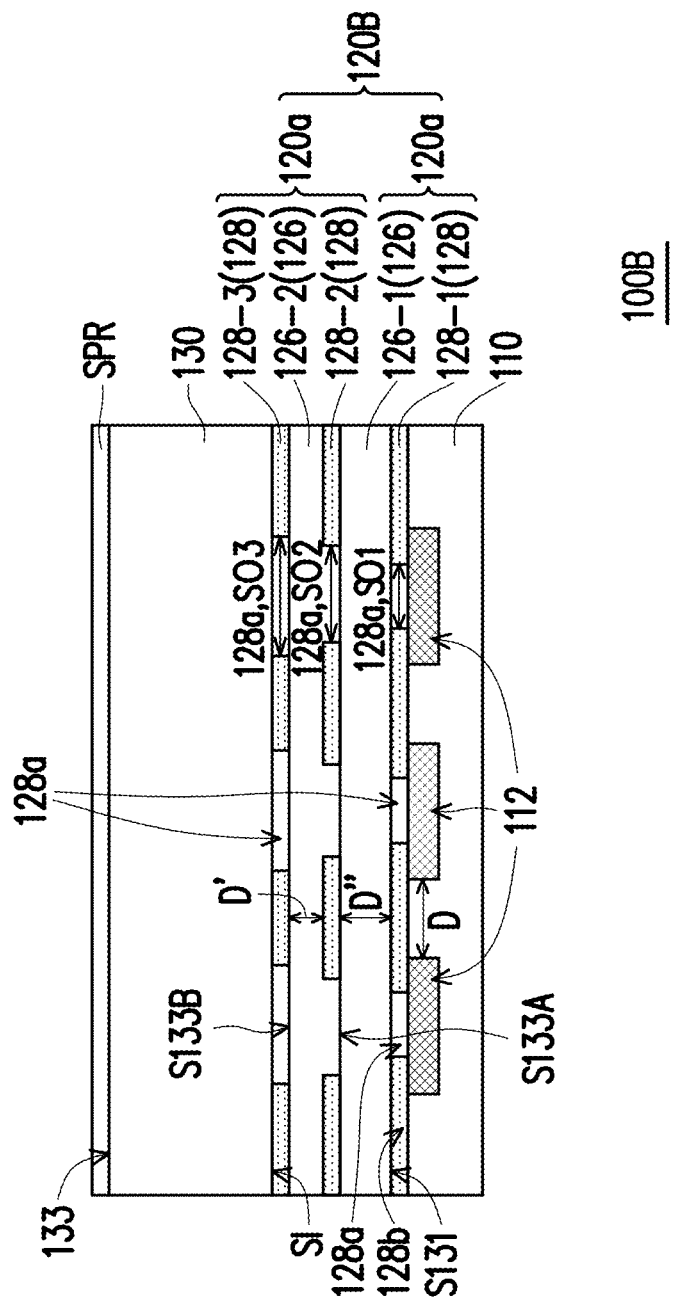
FIG. 7 is a cross-sectional schematic diagram illustrating a bio-sensing apparatus according to an exemplary embodiment of the invention.
Figure 8:
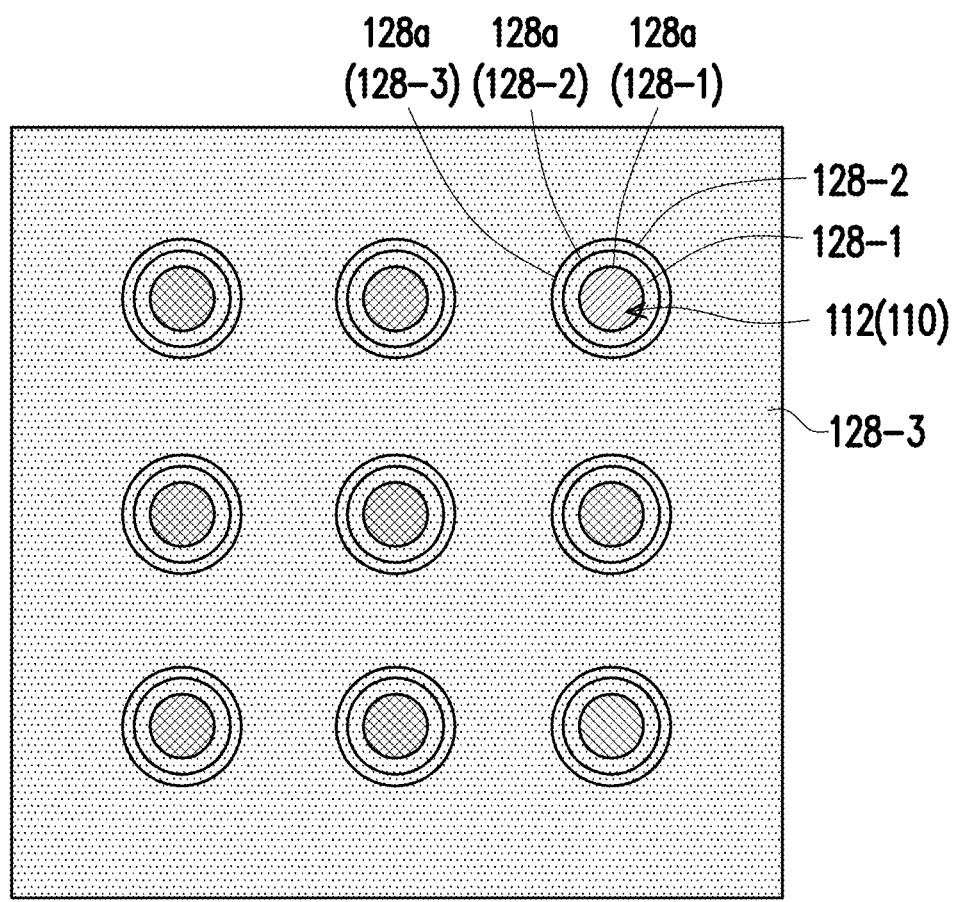
FIG. 8 and FIG. 9 are top schematic diagrams respectively illustrating the bio-sensing apparatus according to a bio-sensing apparatus 100B of the exemplary embodiment of FIG. 7 in a case where a process tolerance is absent and in a case where a process tolerance is present.
Figure 9:
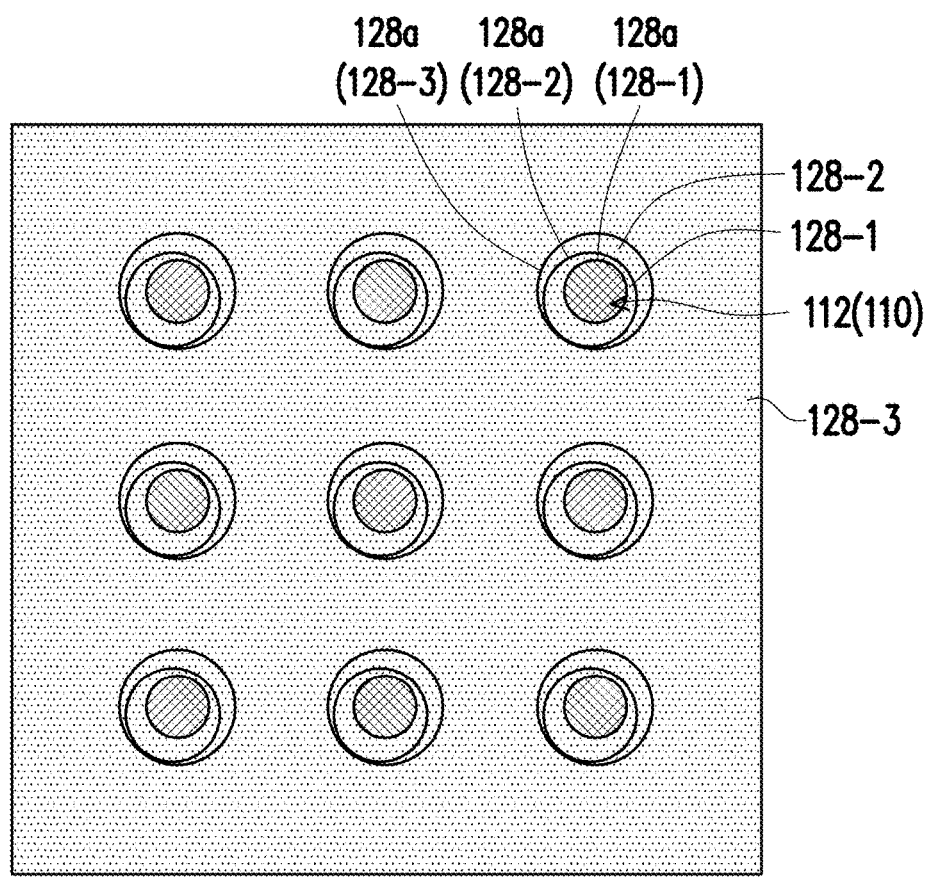

FIG. 7 is a cross-sectional schematic diagram illustrating a bio-sensing apparatus according to an exemplary embodiment of the invention. FIG. 8 and FIG. 9 are top schematic diagrams respectively illustrating the bio-sensing apparatus according to a bio-sensing apparatus 100B of the exemplary embodiment of FIG. 7 in a case where a process tolerance is absent and in a case where a process tolerance is present.

Referring to FIG. 7 and FIG. 8, the bio-sensing apparatus 100B is adapted to capture a biometric feature of an object under test. For example, the object under test may be a finger or a palm, and the biometric feature may be a fingerprint, a palm print, or a vein, but the invention is not limited hereto.

The bio-sensing apparatus 100B includes a light-transmitting element 130, a sensing element 110, and a spatial filter element 120B.

The spatial filter element 120B is disposed between the light-transmitting element 130 and the sensing element 110 and is adapted to collimate the light beam that is reflected by the object under test and transmitted towards the sensing element 110. Specifically, the spatial filter element 120B includes a first spatial filter layer 128-1, a second spatial filter layer 128-2, and a third spatial filter layer 128-3 that are overlapped with each other.

In order to allow the light beam reflected by the object under test to be received by the sensing element 110, the first spatial filter layer 128-1, the second spatial filter layer 128-2, and the third spatial filter layer 128-3 respectively include a plurality of first light-transmitting portions 128a, a plurality of second light-transmitting portions 128a and a plurality of third light-transmitting portions 128a. Each of the first light-transmitting portions 128a is overlapped with one of the second light-transmitting portions 128a, one of the third light-transmitting portions 128a, and a corresponding sensing unit 112, such that a small-angle light beam transmitted towards the sensing unit 112 is transmitted to the corresponding sensing unit 112 through the one first light-transmitting portion 128a, the one second light-transmitting portion 128a, and the one third light-transmitting portion 128a that are overlapped with each other.

The spatial filter element 120B satisfies the following condition: a size SO3 of each of the third light-transmitting portions 128a is larger than or equal to a size SO2 of each of the second light-transmitting portions 128a, and the size SO2 of each of the second light-transmitting portions 128a is larger than a size SO1 of each of the first light-transmitting portions 128a; or the size SO3 of each of the third light-transmitting portions 128a is larger than the size SO2 of each of the second light-transmitting portions 128a, and the size SO2 of each of the second light-transmitting portions 128a is larger than or equal to the size SO1 of each of the first light-transmitting portions 128a. In a framework where a shape of the light-transmitting portions is circular, the size of the light-transmitting portions refers to a diameter of the light-transmitting portions. In a framework where the shape of the light-transmitting portions is a rectangle, another polygon, or a combination of the foregoing shapes, the size of the light-transmitting portions refers to a width of one of edges of the light-transmitting portions.

In a case where sizes of the plurality of light-transmitting portions of the plurality of spatial filter layers are all identical, the larger the sizes of the plurality of light-transmitting portions, the larger an amount of light entering the sensing units 112, but crosstalk is likely to occur. Conversely, as the sizes of the plurality of light-transmitting portions become smaller, although crosstalk is effectively improved, the amount of entering light is likely to be overly small. Moreover, it is likely that centers of the plurality of light-transmitting portions of the different spatial filter layers cannot be aligned due to a process tolerance. In other words, the spatial filter layer closer to the sensing units 112 may block the light-transmitting portions above it (i.e., a hole blocking phenomenon), which causes an effective opening value (i.e., an intersecting region of the light-transmitting portions of the different spatial filter layers) corresponding to each of the sensing units 112 to be smaller than a predetermined effective opening value (i.e., the sizes of the light-transmitting portions) and thereby causes an actual amount of entering light of each of the sensing units 112 to be smaller than a predetermined amount of entering light of each of the sensing units 112.

Accordingly, in the exemplary embodiment, when designing the sizes of the plurality of light-transmitting portions of the different spatial filter layers, the crosstalk, the amount of entering light, and the hole blocking phenomenon caused by the process tolerance are all taken into consideration. For example, the size SO1 of the first light-transmitting portions 128a of the first spatial filter layer 128-1 is designed according to the size of each of the sensing units 112, a transverse distance D between two adjacent sensing units 112, and a longitudinal distance (including a longitudinal distance D' and a longitudinal distance D") between two adjacent spatial filter layers, to improve issues of crosstalk and an overly small amount of entering light at the same time. Moreover, the size of the light-transmitting portions of at least one layer of the other spatial filter layers (e.g., at least one of the second spatial filter layer 128-2 and the third spatial filter layer 128-3) is configured to be larger than the size SO1 of the first light-transmitting portions 128a of the first spatial filter layer 128-1. Accordingly, even if the centers of the plurality of light-transmitting portions of the different spatial filter layers cannot be aligned due to the process tolerance (see FIG. 9), the spatial filter layer closer to the sensing units 112 is prevented from blocking the light-transmitting portions above it, such that the effective opening value corresponding to each of the sensing units 112 is equal to or similar to the predetermined effective opening value (i.e., the size SO1 of the first light-transmitting portions 128a) and thereby the amount of light entering the sensing element 110 is not overly limited while crosstalk is improved.

In the exemplary embodiment, the size SO3 of each of the third light-transmitting portions 128a is larger than the size SO2 of each of the second light-transmitting portions 128a, and the size SO2 of each of the second light-transmitting portions 128a is larger than the size SO1 of each of the first light-transmitting portions 128a. Moreover, the first spatial filter layer 128-1, the second spatial filter layer 128-2, and the third spatial filter layer 128-3 are sequentially arranged from the sensing element 110 towards the light-transmitting element 130. However, relative relations between the sizes of the different light-transmitting portions and arrangement of the different spatial filter layers may be changed according to the requirement and are not limited to those illustrated in FIG. 7.

According to different requirements, the spatial filter element 120B may further include other components. For example, the spatial filter element 120B may further include a first light-transmitting layer 126-1 and a second light-transmitting layer 126-2 to carry the spatial filter layers. The first light-transmitting layer 126-1 and the second light-transmitting layer 126-2 are adapted to allow the light beam to pass through. For example, the light-transmitting layer may be glass substrates, plastic substrates, or transparent photoresists but are not limited hereto.

The first light-transmitting layer 126-1 is located between the sensing element 110 and the light-transmitting element 130, and the second light-transmitting layer 126-2 is located between the first light-transmitting layer 126-1 and the light-transmitting element 130. The second spatial filter layer 128-2 is located between the first light-transmitting layer 126-1 and the second light-transmitting layer 126-2. The first spatial filter layer 128-1 is located between the sensing element 110 and the first light-transmitting layer 126-1. The third spatial filter layer 128-3 is located between the second light-transmitting layer 126-2 and the light-transmitting element 130. In the exemplary embodiment, the first spatial filter layer 128-1 is disposed on a surface S131 of the first light-transmitting layer 126-1 facing the sensing element 110, the second spatial filter layer 128-2 is embedded in a surface S133A of the second light-transmitting layer 126-2 facing the first light-transmitting layer 126-1, and the third spatial filter layer 128-3 is disposed on a surface S133B of the second light-transmitting layer 126-2 facing the light-transmitting element 130, but the invention is not limited hereto. In an exemplary embodiment, the first spatial filter layer 128-1 may be embedded in the surface S131 of the first light-transmitting layer 126-1 facing the sensing element 110. Moreover, the second spatial filter layer 128-2 may be disposed on the surface S133A of the second light-transmitting layer 126-2 facing the first light-transmitting layer 126-1. In addition, the third spatial filter layer 128-3 may be embedded in the surface S133B of the second light-transmitting layer 126-2 facing the light-transmitting element 130.

An adhesive layer (not illustrated) or a fixing mechanism (not illustrated) may be provided between the light-transmitting element 130 and the second light-transmitting layer 126-2, between the second light-transmitting layer 126-2 and the first light-transmitting layer 126-1, and between the first light-transmitting layer 126-1 and the sensing element 110 to fix them together. The adhesive layer may be an optical clear adhesive (OCA) or a die attach film (DAF) but is not limited hereto. When the light-transmitting element 130 and the second light-transmitting layer 126-2 are fixed together through the adhesive layer, the adhesive layer may be located in a light-transmitting portion 128a (i.e. a light-transmitting opening of the spatial filter layer 128) between the light-transmitting element 130 and the second light-transmitting layer 126-2, between the third spatial filter layer 128-3 and the light-transmitting element 130, or a combination of the two. In other words, a light-transmitting medium in the light-transmitting portion 128a between the light-transmitting element 130 and the second light-transmitting layer 126-2 may be air or the adhesive layer. Moreover, when the second light-transmitting layer 126-2 and the first light-transmitting layer 126-1 are fixed together through the adhesive layer, the adhesive layer may be located between the second light-transmitting layer 126-2 and the first light-transmitting layer 126-1, between the second spatial filter layer 128-2 and the first light-transmitting layer 126-1, or a combination of the two. In addition, when the first light-transmitting layer 126-1 and the sensing element 110 are fixed together through the adhesive layer, the adhesive layer may be located in a light-transmitting portion 128a (i.e. a light-transmitting opening of the spatial filter layer 128) between the first light-transmitting layer 126-1 and the sensing element 110, between the first spatial filter layer 128-1 and the sensing element 110, or a combination of the two. In other words, a light-transmitting medium in the light-transmitting portion 128a (i.e. a light-transmitting opening of the spatial filter layer 128) between the first light-transmitting layer 126-1 and the sensing element 110 may be air or the adhesive layer.

Figure 10:
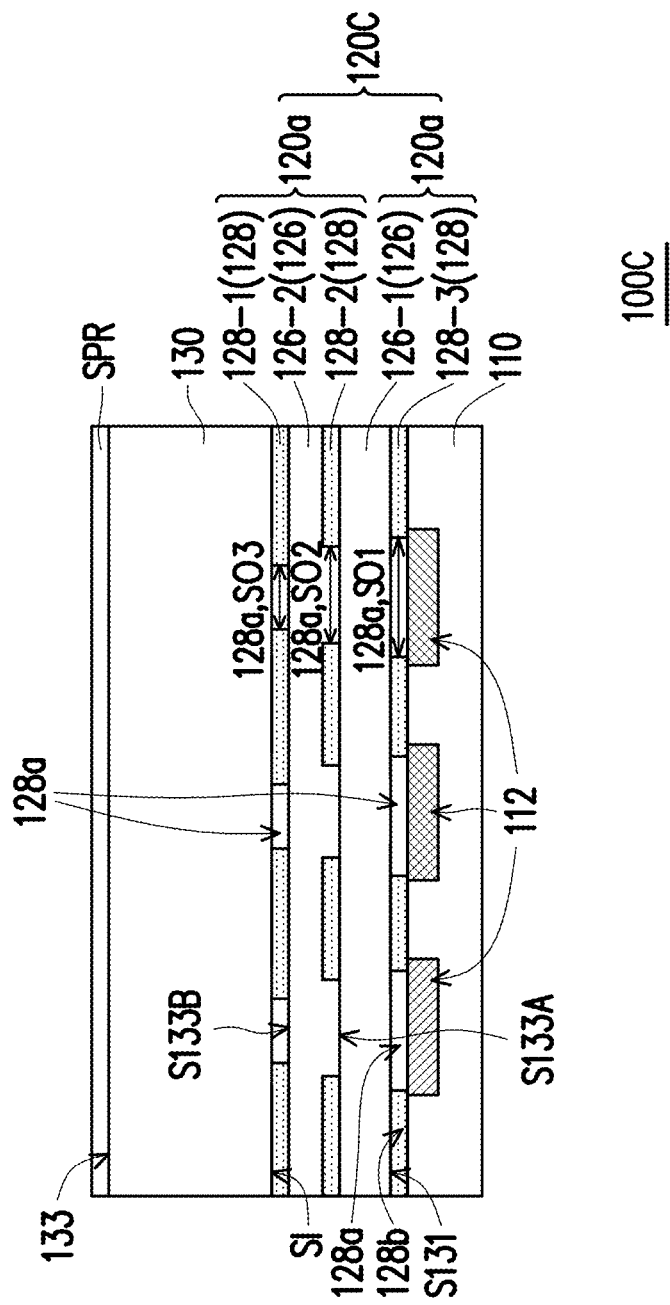
FIG. 10 is a cross-sectional schematic diagram illustrating a bio-sensing apparatus according to an exemplary embodiment of the invention.

FIG. 10 is a cross-sectional schematic diagram illustrating a bio-sensing apparatus according to an exemplary embodiment of the invention. Referring to FIG. 10, the main differences between a bio-sensing apparatus 100C and the bio-sensing apparatus 100B of FIG. 7 are described below. In the bio-sensing apparatus 100B of FIG. 7, the sizes of the plurality of light-transmitting portions 128a of the different spatial filter layers 128 are incrementally increased from the sensing element 110 towards the light-transmitting element 130. In contrast, in the bio-sensing apparatus 100C of FIG. 10, the sizes of the plurality of light-transmitting portions 128a of the different spatial filter layers 128 are incrementally decreased from the sensing element 110 towards the light-transmitting element 130.

Specifically, the first spatial filter layer 128-1, the second spatial filter layer 128-2, and the third spatial filter layer 128-3 are sequentially arranged from the light-transmitting element 130 towards the sensing element 110, such that the third spatial filter layer 128-3 is located between the sensing element 110 and the first light-transmitting layer 126-1, and the first spatial filter layer 128-1 is located between the second light-transmitting layer 126-2 and the light-transmitting element 130. In the exemplary embodiment, the third spatial filter layer 128-3 is disposed on the surface S131 of the first light-transmitting layer 126-1 facing the sensing element 110, and the first spatial filter layer 128-1 is disposed on the surface S133B of the second light-transmitting layer 126-2 facing the light-transmitting element 130, but the invention is not limited hereto. In an exemplary embodiment, the third spatial filter layer 128-3 may be embedded in the surface S131 of the first light-transmitting layer 126-1 facing the sensing element 110, and the first spatial filter layer 128-1 may be embedded in the surface S133B of the second light-transmitting layer 126-2 facing the light-transmitting element 130.

Referring to FIG. 7 and FIG. 10, the bio-sensing apparatus 100B and the bio-sensing apparatus 100B respectively includes surface plasma resonance layers SPR. Functions of the surface plasma resonance layers SPR of the bio-sensing apparatus 100B and the bio-sensing apparatus 100C and a function of the surface plasma resonance layer SPR of the above bio-sensing apparatus 100 are the same, and which will not be repeated here.

Figure 11:
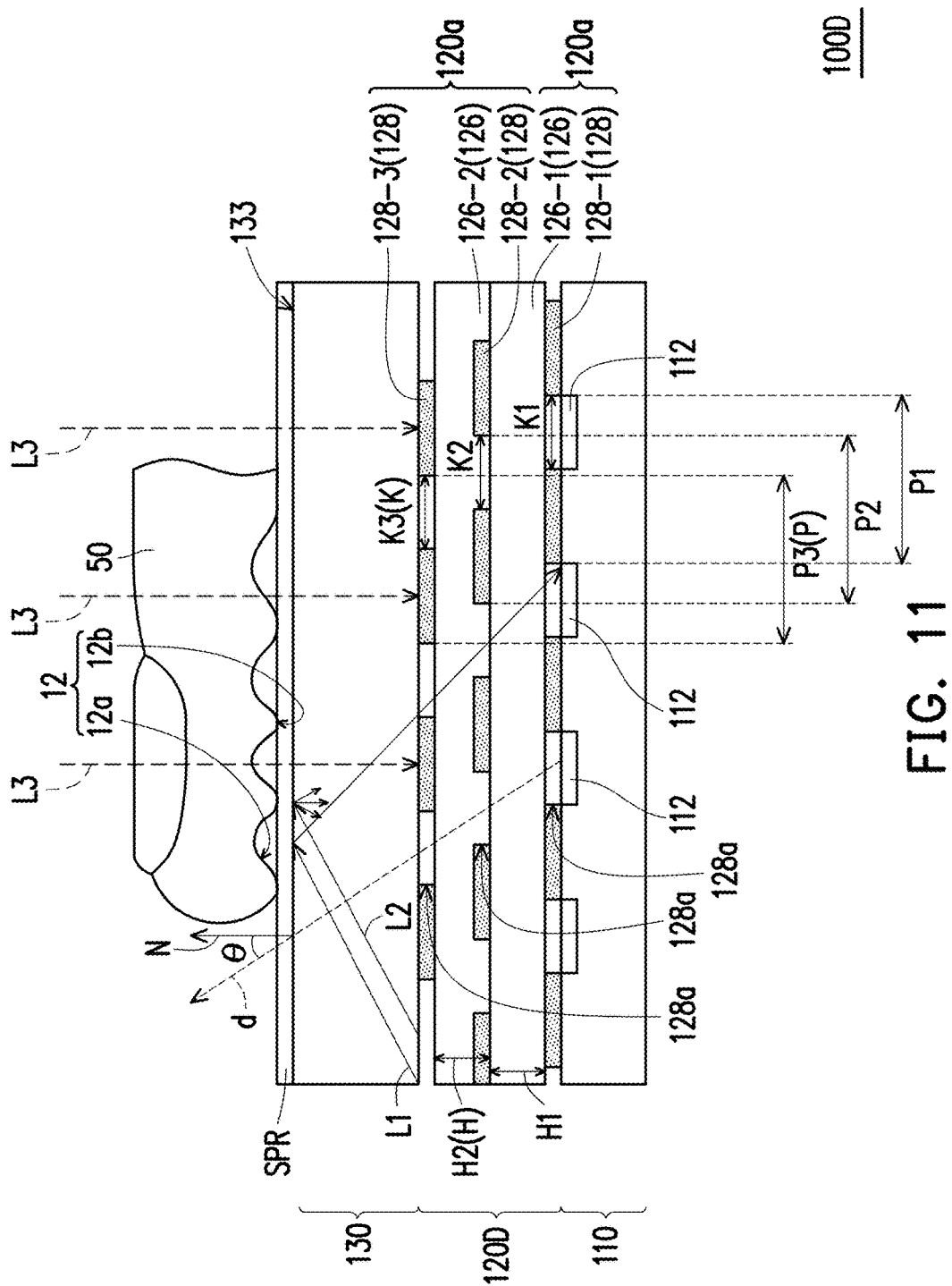
FIG. 11 is a cross section of a bio-sensing apparatus of an embodiment of the invention.

FIG. 11 is a cross section of a bio-sensing apparatus of an embodiment of the invention. Referring to FIG. 11, a bio-sensing apparatus 100D is configured to obtain a fingerprint 12 image. The bio-sensing apparatus 100 includes a light-transmitting element 110, an sensing element 120 disposed opposite to the light-transmitting element 110, and a spatial filter element 130 disposed between the light-transmitting element 110 and the sensing element 120.

The bio-sensing apparatus 100D further includes a light-emitting element (not shown) configured to emit the sensing light beams L1 and L2. In the present embodiment, the sensing light beams L1 and L2 can be transmitted to a pressing surface 110a via the light-transmitting element 110. The fingerprint 12 of a user 50 located on the pressing surface 110a has a valley 12a and a peak 12b. When a portion of the sensing light beam L1 is incident on a portion of the pressing surface 110a corresponding to the valley 12a, the total reflection of the portion of the sensing light beam L1 is not destroyed and then is obliquely incident on a corresponding sensing unit 120a. When a portion of the sensing light beam L2 is incident on a portion of the pressing surface 110a corresponding to the peak 12b, the total reflection of the portion of the sensing light beam L2 is destroyed and scattered, and then is incident on the corresponding sensing unit 120a. The energy of the portion of the sensing light beam L1 incident on the sensing unit 120a and corresponding to the valley 12a is strong, the energy of the sensing light beam L2 incident on the sensing unit 120a and corresponding to the peak 12b is weak, and therefore the sensing element 120 can capture a light and dark fingerprint 12 image.

The spatial filter element 130 includes a plurality of spatial filter layers 132 and a plurality of light-transmitting layers 134. The plurality of spatial filter layers 132 and the plurality of light-transmitting layers 134 are alternately stacked. Each of the spatial filter layers 132 has a plurality of light-transmitting portions 132a respectively corresponding to the plurality of sensing units 120a of the sensing element 120. For instance, in the present embodiment, the spatial filter element 130 can optionally include three spatial filter layers 132-1, 132-2, and 132-3 and two light-transmitting layers 134-1 and 134-2, wherein the spatial filter layer 132-1, the light-transmitting layer 134-1, the spatial filter layer 132-2, the light-transmitting layer 134-2, and the spatial filter layer 132-3 are arranged from the sensing element 120 toward the light-transmitting element 110 in order.

It should be mentioned that, the number of the spatial filter layer 132 and the number of the light-transmitting layer 134 above and shown in the figures are only exemplary to the invention and are not intended to limit the invention. According to other embodiments, the number of the spatial filter layer 132 and the number of the light-transmitting layer 134 of the spatial filter element 130 can also be designed as other suitable numbers based on actual need.

It should be mentioned that, light-transmitting portions 132a of the plurality of spatial filter layers 132-1, 132-2, and 132-3 corresponding to one sensing unit 120a is arranged along an oblique direction d, the oblique direction d and a normal direction N of the pressing surface 110a have an included angle θ, and 0°<θ<90°. For instance, in the present embodiment, preferably, 35°<θ<85°. Specifically, in the present embodiment, θ can equal to 60°, but the invention is not limited thereto.

In the present embodiment, the plurality of light-transmitting portions 132a of one spatial filter layer 132-1 of the plurality of spatial filter layers 132 of the spatial filter element 130 closest to the sensing element 120 are respectively aligned with the plurality of sensing units 120a of the sensing element 120, and light-transmitting portions 132a of the other spatial filter layers 132-2 and 132-3 of the spatial filter element 130 are not aligned with the plurality of sensing units 120a of the sensing element 120 and is offset toward the same side (such as toward the left), wherein the degree of offset of the plurality of light-transmitting portions 132a of the spatial filter layers 132-2 and 132-3 farther from the sensing element 120 is greater compared to the plurality of corresponding sensing units 120a. In another embodiment of the invention, the plurality of light-transmitting portions 132a of one spatial filter layer 132-1 in the plurality of spatial filter layers 132 of the spatial filter element 130 closest to the sensing element 120 is respectively not aligned with the plurality of sensing units 120a of the sensing element 120 (for instance, the light-transmitting portion of the spatial filter layer 132-1 is slightly less than the sensing unit 120a), but the invention is not limited thereto.

It should be mentioned that, the plurality of light-transmitting portions 132a of the plurality of spatial filter layers 132-1, 132-2, and 132-3 arranged along the oblique direction d forms a plurality of optical channels, and since the optical channels are obliquely disposed, an ambient beam L3 (such as sunlight) substantially perpendicularly incident on the pressing surface 110a does not readily pass through the optical channels and is transmitted to the image-sensing element 120. Accordingly, the ambient beam L3 does not readily interfere with the fingerprint 12 information carried by the sensing light beams L1 and L2, such that the fingerprint 12 image quality can be significantly increased.

In the present embodiment, the plurality of light-transmitting portions 132a of the plurality of different spatial filter layers 132 are arranged at equal spacing. Specifically, the plurality of light-transmitting portions 132a of the spatial filter layer 132-1 are arranged at a spacing P1, the plurality of light-transmitting portions 132a of the spatial filter layer 132-2 are arranged at a spacing P2, the plurality of light-transmitting portions 132a of the spatial filter layer 132-3 are arranged at a spacing P3, and the spacing P1, the spacing P2, and the spacing P3 can substantially be the same. For instance, in the present embodiment, the spacing P1, the spacing P2, and the spacing P3 can all be 50 µm, but the invention is not limited thereto.

In the present embodiment, the diameter of light-transmitting portions 132a corresponding to one sensing unit 120a can be substantially identical. In other words, one light-transmitting portion 132a of the spatial filter layer 132-1, one light-transmitting portion 132a of the spatial filter layer 132-2, and one light-transmitting portion 132a of the spatial filter layer 132-3 correspond to one sensing unit 120a, one light-transmitting portion 132a of the spatial filter layer 132-1 has a diameter K1, one light-transmitting portion 132a of the spatial filter layer 132-2 has a diameter K2, and one light-transmitting portion 132a of the spatial filter layer 132-3 has a diameter K3, and the diameter K1, the diameter K2, and the diameter K3 are substantially one, but the invention is not limited thereto. For instance, the diameter K1, the diameter K2, and the diameter K3 can be 15 µm, but the invention is not limited thereto. Moreover, in the present embodiment, a thickness H1 of the light-transmitting layer 134-1 and a thickness H2 of the light-transmitting layer 134-2 can be identical. For instance, the thickness H1 of the light-transmitting layer 134-1 and the thickness H2 of the light-transmitting layer 134-2 can both be 50 µm, but the invention is not limited thereto.

Figure 12:
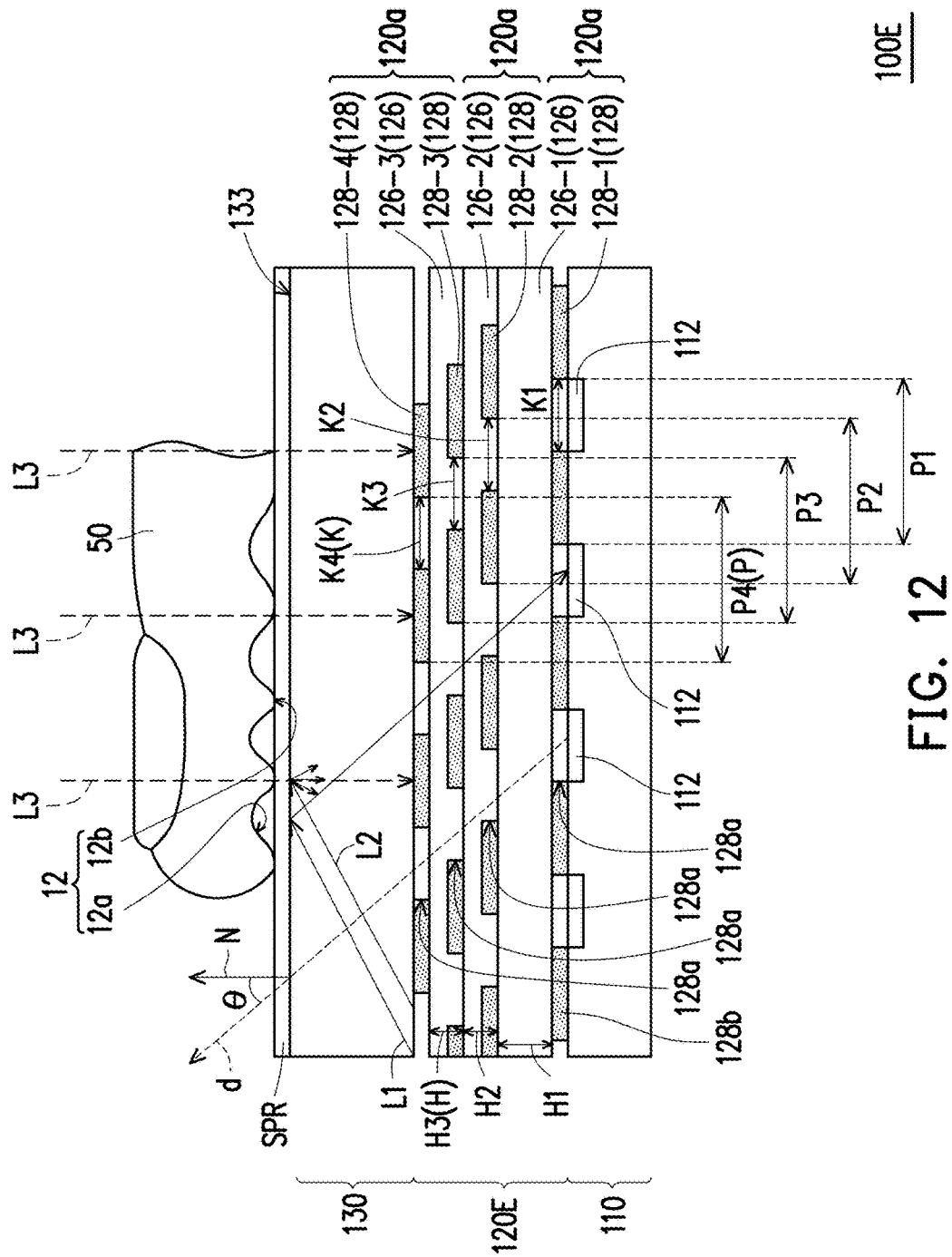
FIG. 12 is a cross section of a bio-sensing apparatus of an embodiment of the invention.

FIG. 12 is a cross section of a bio-sensing apparatus of an embodiment of the invention. Referring to FIG. 11 and FIG. 12, a bio-sensing apparatus 100E is similar to the bio-sensing apparatus 100D, and one or similar portions of the two are provided above and not repeated herein. The main difference between the bio-sensing apparatus 100E and the bio-sensing apparatus 100D is that the bio-sensing apparatus 100E further includes a light-transmitting layer 134-3 and a spatial filter layer 132-4, wherein the spatial filter layer 132-1, the light-transmitting layer 134-1, the spatial filter layer 132-2, the light-transmitting layer 134-2, the spatial filter layer 132-3, the light-transmitting layer 134-3, and the spatial filter layer 132-4 are arranged from the sensing element 120 toward the light-transmitting element 110 in order.

In the present embodiment, the plurality of light-transmitting portions 132a of the spatial filter layer 132-1 are arranged at a spacing P1, the plurality of light-transmitting portions 132a of the spatial filter layer 132-2 are arranged at a spacing P2, the plurality of light-transmitting portions 132a of the spatial filter layer 132-3 are arranged at a spacing P3, the plurality of light-transmitting portions 132a of the spatial filter layer 132-4 are arranged at a spacing P4, and the spacing P1, the spacing P2, the spacing P3, and the spacing P4 can be substantially identical. For instance, in the present embodiment, the spacing P1, the spacing P2, the spacing P3, and the spacing P4 can all be 50 µm, but the invention is not limited thereto.

In the present embodiment, one light-transmitting portion 132a of the spatial filter layer 132-1 has a diameter K1, one light-transmitting portion 132a of the spatial filter layer 132-2 has a diameter K2, one light-transmitting portion 132a of the spatial filter layer 132-3 has a diameter K3, one light-transmitting portion 132a of the spatial filter layer 132-4 has a diameter K4, and the diameter K1, the diameter K2, the diameter K3, and the diameter K4 can be substantially identical. For instance, in the present embodiment, the diameter K1, the diameter K2, the diameter K3, and the diameter K4 can all be 15 µm, but the invention is not limited thereto.

In the present embodiment, the thickness H1 of the light-transmitting layer 134-1, the thickness H2 of the light-transmitting layer 134-2, and the thickness H3 of the light-transmitting layer 134-3 are not identical. For instance, the thickness H1 of the light-transmitting layer 134-1, the thickness H2 of the light-transmitting layer 134-2, and the thickness H3 of the light-transmitting layer 134-3 can respectively be 50 μm, 25 μm, and 25 μm, but the invention is not limited thereto. Moreover, in the present embodiment, θ can equal to 60°, but the invention is not limited thereto.

Figure 13:
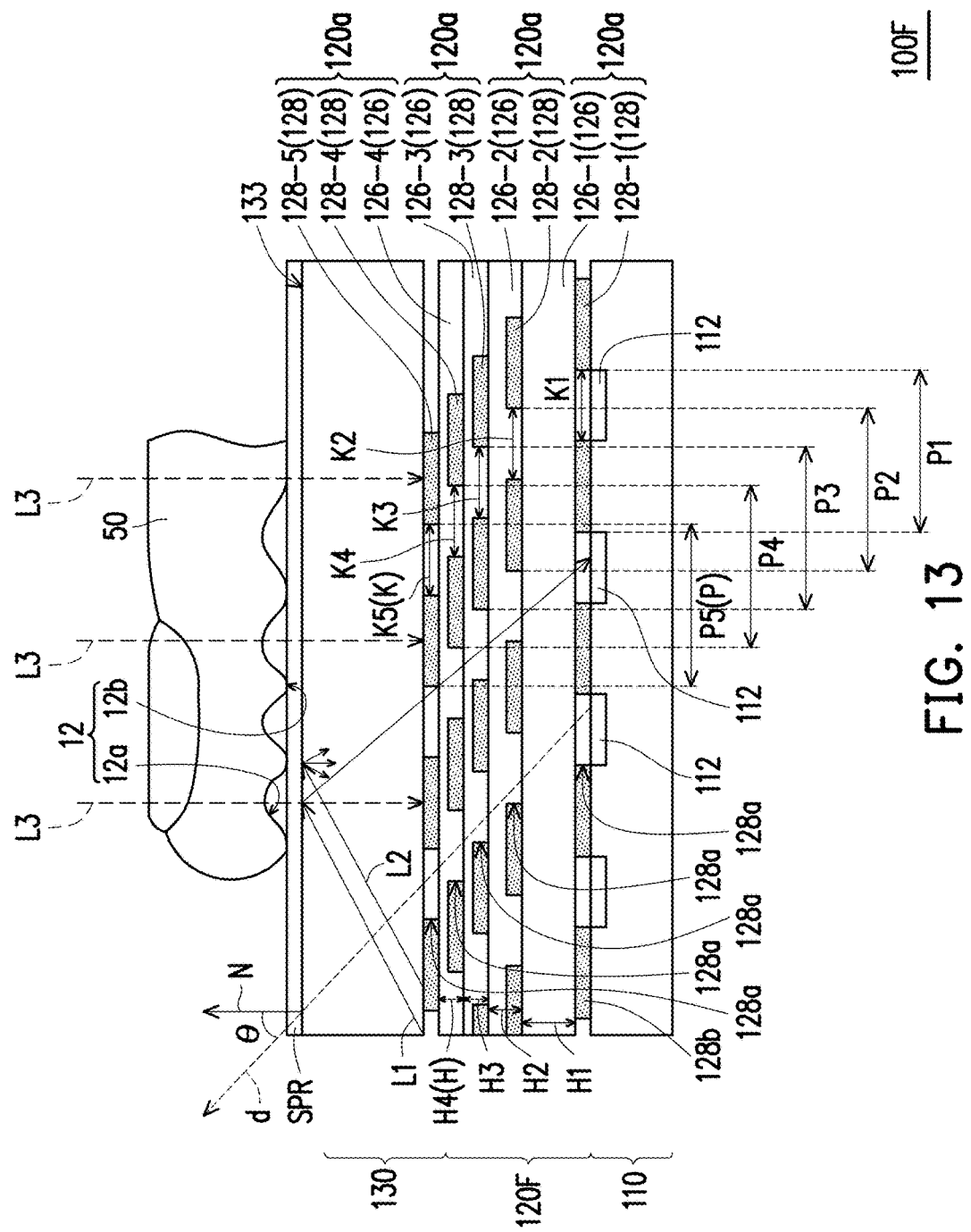
FIG. 13 is a cross section of a bio-sensing apparatus of an embodiment of the invention.

FIG. 13 is a cross section of a bio-sensing apparatus of an embodiment of the invention. Referring to FIG. 12 and FIG. 13, a bio-sensing apparatus 100F is similar to the bio-sensing apparatus 100E, and one or similar portions of the two are provided above and not repeated herein. The main difference between the bio-sensing apparatus 100F and the bio-sensing apparatus 100E is that the bio-sensing apparatus 100F further includes a light-transmitting layer 134-4 and a spatial filter layer 132-5, wherein the spatial filter layer 132-1, the light-transmitting layer 134-1, the spatial filter layer 132-2, the light-transmitting layer 134-2, the spatial filter layer 132-3, the light-transmitting layer 134-3, the spatial filter layer 132-4, the light-transmitting layer 134-4, and the spatial filter layer 132-5 are arranged from the sensing element 120 toward the light-transmitting element 110 in order.

In the present embodiment, the plurality of light-transmitting portions 132a of the spatial filter layer 132-1 are arranged at a spacing P1, the plurality of light-transmitting portions 132a of the spatial filter layer 132-2 are arranged at a spacing P2, the plurality of light-transmitting portions 132a of the spatial filter layer 132-3 are arranged at a spacing P3, the plurality of light-transmitting portions 132a of the spatial filter layer 132-4 are arranged at a spacing P4, the plurality of light-transmitting portions 132a of the spatial filter layer 132-5 are arranged at a spacing P5, and the spacing P1, the spacing P2, the spacing P3, the spacing P4, and the spacing P5 can be substantially identical, but the invention is not limited thereto. For instance, the spacing P1, the spacing P2, the spacing P3, the spacing P4, and the spacing P5 can all be 50 μm, but the invention is not limited thereto.

In the present embodiment, one light-transmitting portion 132a of the spatial filter layer 132-1 has a diameter K1, one light-transmitting portion 132a of the spatial filter layer 132-2 has a diameter K2, one light-transmitting portion 132a of the spatial filter layer 132-3 has a diameter K3, one light-transmitting portion 132a of the spatial filter layer 132-4 has a diameter K4, one light-transmitting portion 132a of the spatial filter layer 132-5 has a diameter K5, and the diameter K1, the diameter K2, the diameter K3, the diameter K4, and the diameter K5 can be substantially identical. For instance, the diameter K1, the diameter K2, the diameter K3, the diameter K4, and the diameter K5 can all be 15 μm, but the invention is not limited thereto.

In the present embodiment, the thickness H1 of the light-transmitting layer 134-1, the thickness H2 of the light-transmitting layer 134-2, the thickness H3 of the light-transmitting layer 134-3, and the thickness H4 of the light-transmitting layer 134-4 can respectively be 50 μm, 25 μm, 12.5 μm, and 12.5 μm, but the invention is not limited thereto. Moreover, in the present embodiment, θ can equal to 60°, but the invention is not limited thereto.

It should be mentioned that, in the present embodiment, the plurality of light-transmitting portions 132a of the spatial filter layer 132-5 are arranged at a spacing P (such as 50 μm), one light-transmitting portion 132a of the spatial filter layer 132-5 has a diameter K (such as 15 μm), the spatial filter layer 132-5 is disposed on the light-transmitting layer 134-4, the light-transmitting layer 134-4 has a thickness H (such as 12.5 μm), and the diameter K, the spacing P, and the thickness H satisfy the following formula (1):

$$\left(\frac{H}{P-D}\right) \leq 0.5.$$

In the present embodiment, the diameter K of formula (1) can refer to the diameter K5 of one light-transmitting portion 132a of the spatial filter layer 132-5, the spacing P of formula (1) can refer to the spacing P5 of a plurality of light-transmitting portions 132a of the spatial filter layer 132-5, and the thickness H of formula (1) can refer to the thickness H4 of the light-transmitting layer 134-4, wherein the spatial filter layer 132-5 is one spatial filter layer of the plurality of spatial filter layers 132-1, 132-2, 132-3, 132-4, and 132-5 of the spatial filter element 130 closest to the pressing surface 110a, and the light-transmitting layer 132-4 is one light-transmitting layer 134-2 of the plurality of light-transmitting layers 134-1, 134-2, 132-3, and 132-4 of the spatial filter element 130 closest to the pressing surface 110a. However, the invention is not limited thereto, and in other embodiments, the diameter K of formula (1) can also refer to the diameter K1 of one light-transmitting portion 132a closest to one spatial filter layer 132-1 of the sensing element 120, the spacing P of formula (1) can also refer to the spacing P1 of the plurality of light-transmitting portions 132a closest to one spatial filter layer 132-1 of the sensing element 120, and the thickness T of formula (1) can also refer to the thickness H1 of one light-transmitting layer 134-1 closest to the sensing element 120.

When the diameter K, the spacing P, and the thickness H satisfy formula (1), the bio-sensing apparatus 100F can alleviate the issue of cross-talk so as to obtain a fingerprint 12 image with good quality. Description is provided in the following with reference to FIG. 14 to FIG. 16.

Figure 14:
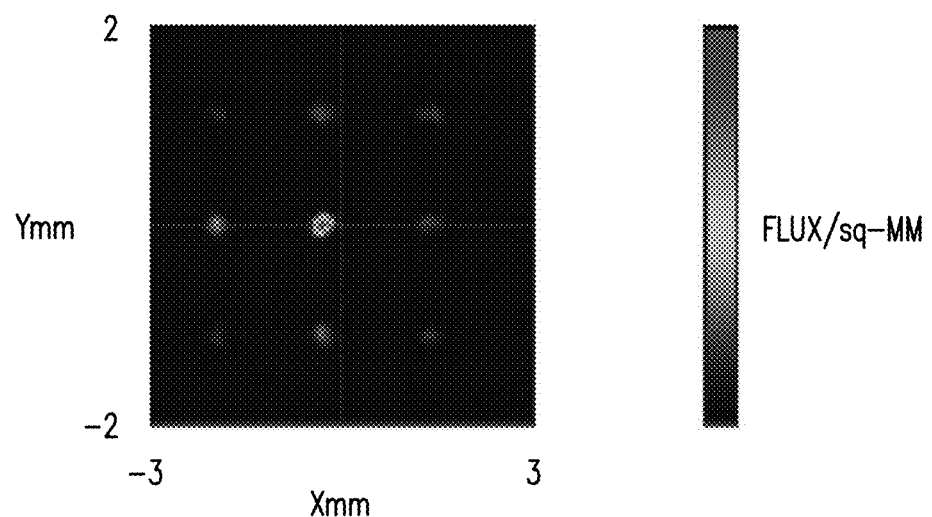
FIG. 14 is a simulated light distribution on a plurality of sensing units 120a of the bio-sensing apparatus 100D of FIG. 11.
Figure 15:
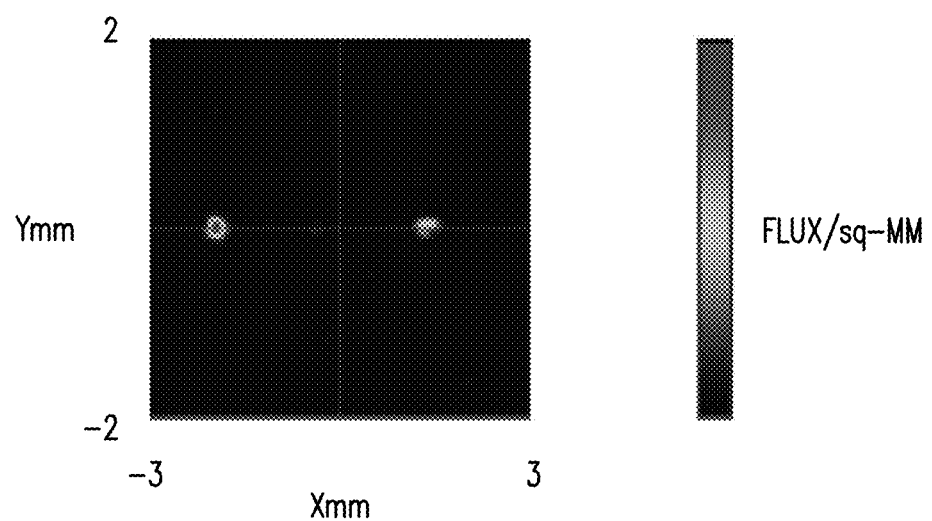
FIG. 15 is a simulated light distribution on a plurality of sensing units 120a of the bio-sensing apparatus 100E of FIG. 12.
Figure 16:
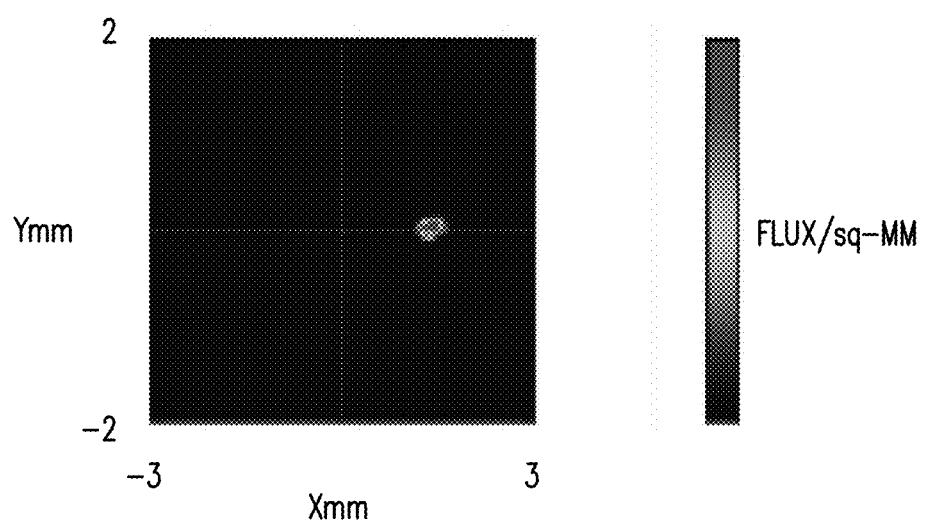
FIG. 16 is a simulated light distribution on a plurality of sensing units 120a of the bio-sensing apparatus 100F of FIG. 13.

FIG. 14 is a simulated light distribution on a plurality of sensing units 120a of the bio-sensing apparatus 100D of FIG. 11. FIG. 15 is a simulated light distribution on a plurality of sensing units 120a of the bio-sensing apparatus 100E of FIG. 12. FIG. 16 is a simulated light distribution on a plurality of sensing units 120a of the bio-sensing apparatus 100F of FIG. 13. The light-emitting elements configured to simulate FIG. 14, FIG. 15, and FIG. 16 have one divergence angles, such as 180°. It can be known from the comparison of FIG. 14, FIG. 15, and FIG. 16 that, when the diameter K, the spacing P, and the thickness H of the bio-sensing apparatus 100F of FIG. 14 corresponding to FIG. 16 satisfy formula (1), the cross-talk issue of the bio-sensing apparatus 100F is significantly alleviated.

Referring to FIG. 11, FIG. 12 and FIG. 13, the bio-sensing apparatus 100D, the bio-sensing apparatus 100E and the bio-sensing apparatus 100F respectively includes surface plasma resonance layers SPR. Functions of the surface plasma resonance layers SPR of the bio-sensing apparatus 100D, the bio-sensing apparatus 100E and the bio-sensing apparatus 100F and a function of the surface plasma resonance layer SPR of the above bio-sensing apparatus 100 are the same, and which will not be repeated here.

Figure 17:
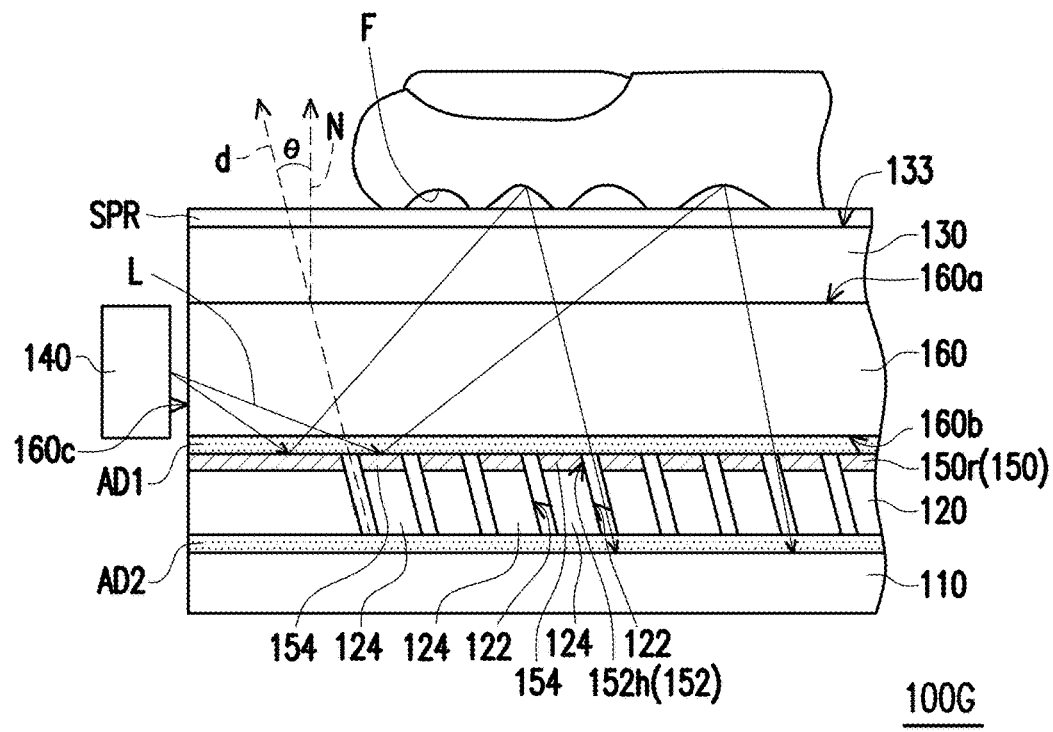
FIG. 17 is a cross-sectional view of a bio-sensing apparatus according to one embodiment of the disclosure.
Figure 18:
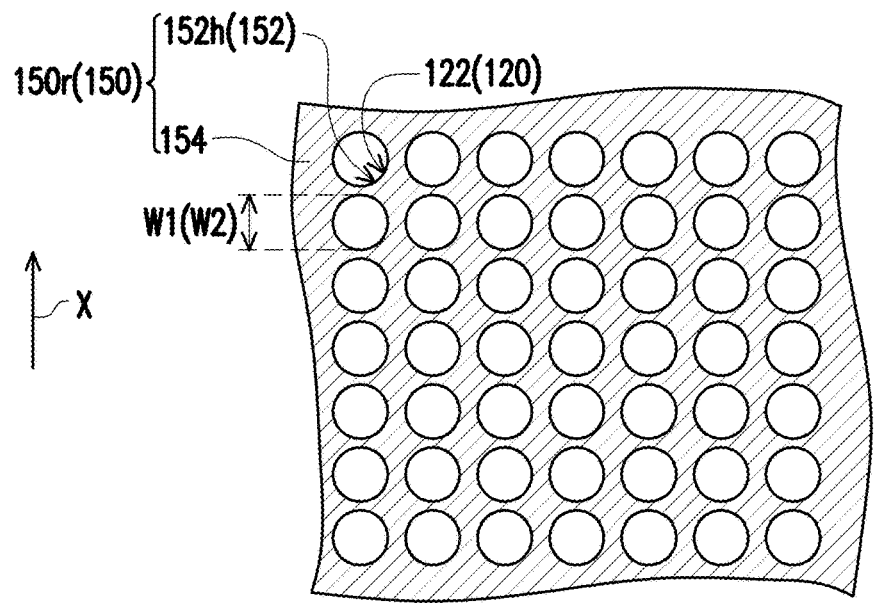
FIG. 18 is a top view of a reflector and a spatial filter element of the bio-sensing apparatus of FIG. 17.

FIG. 17 is a cross-sectional view of a bio-sensing apparatus according to one embodiment of the disclosure. FIG. 18 is a top view of a reflector and a spatial filter element of the bio-sensing apparatus of FIG. 17. Referring to FIG. 17, a bio-sensing apparatus 100G is configured to sense a fingerprint (or a palm print) F of a finger (or palm) and includes a sensing element 110, a light guide 160, at least one light-emitting element 140, a spatial filter element 120 and a reflector 150. The light guide 160 is disposed on the sensing element 110. The at least one light-emitting element 140 is disposed beside the light guide 160 and is configured to emit a light beam L.

The spatial filter element 120 is disposed between the light guide 160 and the sensing element 110 and has a plurality of light-transmitting portions 122 and a light-blocking portion 124 disposed between the two adjacent light-transmitting portions 122. In the embodiment, for example, each of the light-transmitting portions 122 and the light-blocking portions 124 of the spatial filter element 120 may be formed by a plurality of light transmitting layers (not shown) and light shielding layers (not shown) stacking on each other not in a straight line along an oblique direction d. The plurality of light transmitting layers and light shielding layers and workable stacking methods may be seen in Taiwanese Patent Application No. 107202731. The light guide 160 has an upper surface 160a, a lower surface 160b relative to the upper surface 160a and a side surface 160c connected between the upper surface 160a and the lower surface 160b. Each of the light-transmitting portions 122 extends in the oblique direction d, an angle θ is between the oblique direction d and a normal direction N of the upper surface 160a of the light guide 160, and 0°<θ<90°. For example, in the embodiment, the angle θ between 30° and 85° is more preferable. Specifically, in the embodiment, the angle θ may be equal to 42°, but the disclosure is not limited thereto.

The reflector 150 is disposed between the lower surface 160b of the light guide 160 and the spatial filter element 120 and has a plurality of light transmitting portions 152 and at least one reflective portion 154. Each of the light-transmitting portions 122 of the spatial filter element 120 overlaps the at least one light transmitting portion 152 of the reflector 150, and the at least reflective portion 154 of the reflector 150 is disposed on the light-blocking portion 124 of the spatial filter element 120. The light beam L emitted by the light-emitting element 140 is transmitted to a fingerprint F of the finger before being sequentially diffused by the fingerprint F of the finger and passing through the light guide 160, the light transmitting portion 152 of the reflector 150 and the light-transmitting portion 122 of the spatial filter element 120 to be transmitted to the sensing element 110. In the embodiment, the light transmitting portions 152 of the reflector 150 may be a plurality of apertures 152h of a reflective layer 150r which overlap the plurality of light-transmitting portions 122 of the spatial filter element 120, respectively.

Referring to FIGS. 17 and 18, the plurality of light-transmitting portions 122 of the spatial filter element 120 are arranged on the sensing element 110, and each of the light-transmitting portions 122 corresponds to each sensing unit (not shown) of the sensing element 110. The light-blocking portion 124 is distributed between the plurality of light-transmitting portions 122, and the reflective portion 154 of the reflector 150 is disposed on the light-blocking portion 124. Each of the light-transmitting portions 122 has a width W1 in a direction X (shown in FIG. 18), and the direction X is perpendicular to the normal direction N of the upper surface 160a of the light guide 160. Each of the light transmitting portions 152 (the apertures 152h) of the reflector 150 (the reflective layer 152r) has a width W2 in the direction X. In the embodiment, W1=W2, but the disclosure is not limited thereto. In another embodiment, it may be that W1<W2 or W1>W2.

It should be appreciated that the light beam L emitted by the light-emitting element 140 may be led to each position of the light guide 160 by the at least one reflective portion 154 disposed on the light-blocking portion 124. As a result, the light beam L may be distributed evenly in the light guide 160, and there is little likelihood that the intensity of light is higher in an area of the light guide 160 near the light-emitting element 140, while the intensity of light is lower in an area of the light guide 160 that is away from the light-emitting element 140. In this case, the light beam L emitted from the upper surface 160a of the light guide 160 may radiate to the fingerprint F of the finger evenly, and the quality of capturing images by the sensing element 110 improves.

In the embodiment, the bio-sensing apparatus 100G further includes a first adhesive layer AD1 which is disposed between the light guide 160 and the reflector 150 and a second adhesive layer AD2 which is disposed between the spatial filter element 120 and the sensing element 110. In the embodiment, the light guide 160 is bonded to the reflector 150 via the first adhesive layer AD1, and the spatial filter element 120 is bonded to the sensing element 110 via the second adhesive layer AD2. The first adhesive layer AD1 and the second adhesive layer AD2 are made of, for example, an optical clear adhesive (OCA) of high transmittance, but the disclosure is not limited thereto. In another embodiment, the first adhesive layer AD1 and the second adhesive layer AD2 are made of other suitable materials, and/or the first adhesive layer AD1 and the second adhesive layer AD2 may also be made of different materials.

In the embodiment, the bio-sensing apparatus 100G further includes a light-transmitting element 130 which is disposed on the upper surface 160a of the light guide 160 and has a pressing surface 133 for a finger to press. In the embodiment, the fingerprint F of the finger is placed on the pressing surface 133 of the light-transmitting element 130, and the light-emitting element 140 emits the light beam L which is sequentially reflected by the reflector 150 and passes through the light guide 160 and the pressing surface 133 of the light-transmitting element 130 to reach the position of the fingerprint F of the finger.

Figure 19:
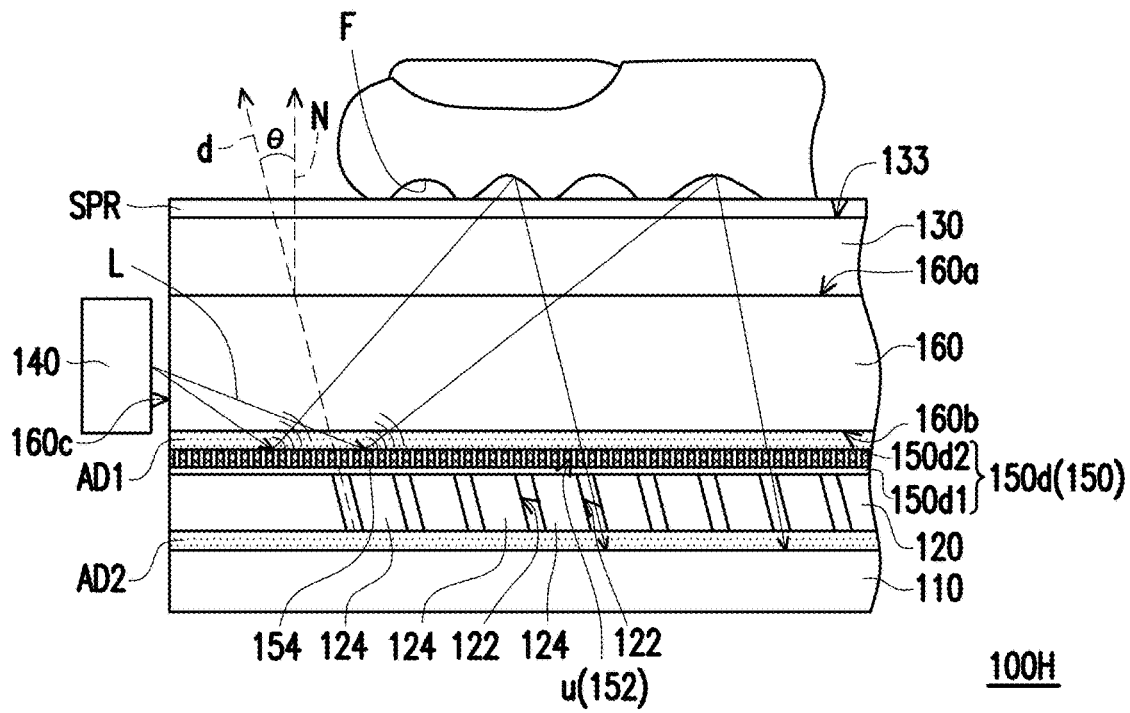
FIG. 19 is a cross-sectional view of a bio-sensing apparatus according to an embodiment of the disclosure.
Figure 20:
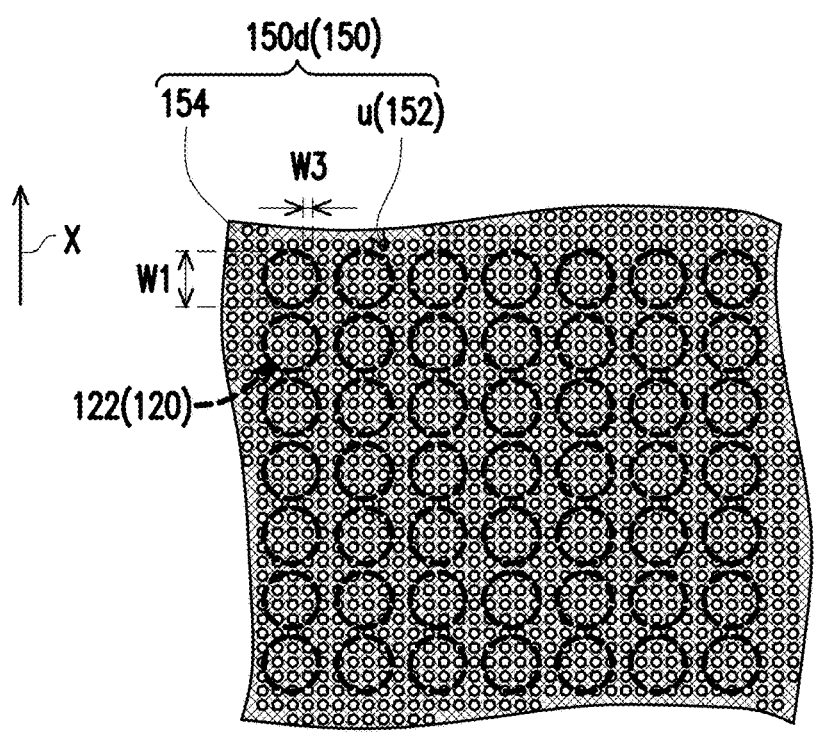
FIG. 20 is a top view of a reflector and a spatial filter element of the bio-sensing apparatus of FIG. 19.

FIG. 19 is a cross-sectional view of a bio-sensing apparatus according to an embodiment of the disclosure. FIG. 20 is a top view of a reflector and a spatial filter element of the bio-sensing apparatus of FIG. 19. Referring to FIG. 19, a bio-sensing apparatus 100H is similar to the bio-sensing apparatus 100G. Identical or similar parts of the bio-sensing apparatus 100H and the bio-sensing apparatus 100G are discussed above, and repeated descriptions are omitted accordingly. The main difference between the bio-sensing apparatus 100H and the bio-sensing apparatus 100G is that the reflector 150 in bio-sensing apparatus 100H is a reflective diffractive element 150d which may include a light transmitting film 150d1 and a reflective pattern layer 150d2 disposed on the light transmitting film 150d1. In the embodiment, the light transmitting film 150d1 may be disposed between the reflective pattern layer 150d2 and the spatial filter element 120, but the disclosure is not limited thereto. In another embodiment, the light transmitting film 150d1 may also be disposed between the light guide 160 and the reflective pattern layer 150d2.

In the embodiment, the light-transmitting portion 122 of the spatial filter element 120 is arranged in the direction X, each of the light-transmitting portions 122 has the width W1 in the direction X, each of the light transmitting portions 152 of the reflective diffractive element 150d has a width W3 in the direction X, and W3≤W1. For example, the light beam L has a wavelength λ, and (0.01) λ≤W3≤(100) λ. In other words, the size of the light transmitting portion 152 of the reflective diffractive element 150d is comparable to the wavelength of the light beam L, and the light beam L diffracts when passing through the light transmitting portion 152 of the reflective diffractive element 150d.

Referring to FIGS. 19 and 20, in the embodiment, the plurality of light transmitting portions 152 of the reflective diffractive element 150d may be a plurality of tiny apertures u. W3, the width of the light transmitting portion 152, is equal to a diameter of the tiny aperture u. The tiny apertures u overlap the light-transmitting portions 122 of the spatial filter element 120 and the light-blocking portions 124 of the spatial filter element 120, but the disclosure is not limited thereto. In another embodiment, the light transmitting portion 152 of the reflective diffractive element 150d may also be a slit structure having the width W3 similar to the wavelength λ of the light beam L. The slit structure is not limited to only have a single width W3 and nor are the plurality of slit structures limited to be disposed in parallel to each other. The plurality of slit structures may have different widths and be disposed parallel to each other or alternately.

In the embodiment, the light beam L diffracts on a surface of the reflective diffractive element 150d and is transmitted to the fingerprint F of the finger in a way of reflective diffraction. The bio-sensing apparatus 100H has similar effects and advantages to the aforementioned bio-sensing apparatus 100G, but repeated descriptions are omitted.

Figure 21:
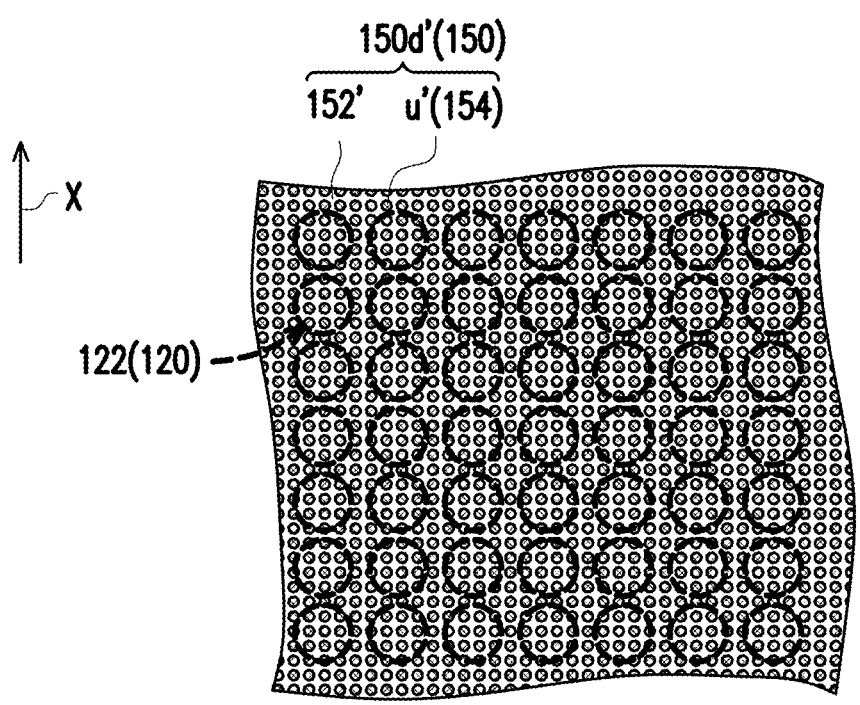
FIG. 21 is a top view of a reflector and a spatial filter element of a bio-sensing apparatus according to an embodiment of the disclosure.

FIG. 21 is a top view of a reflector and a spatial filter element of a bio-sensing apparatus according to an embodiment of the disclosure. Referring to FIGS. 20 and 21, the difference between a reflective diffractive element 150d' of FIG. 21 and the reflective diffractive element 150d of FIG. 20 is that the reflective portions 154 of the reflective diffractive element 150d' of FIG. 21 are a plurality of reflective tiny points u', and light transmitting portions 152' of the reflective diffractive element 150d' of FIG. 21 are light transmitting areas among the plurality of reflective tiny points u'. The reflective diffractive element 150d' of FIG. 21 has identical or similar functions to the reflective diffractive element 150d of FIG. 20. The reflective diffractive element 150d' of FIG. 21 may be configured to substitute for the reflective diffractive element 150d of FIG. 19. The bio-sensing apparatus formed in this way is also protected by the disclosure.

Referring to FIG. 17 and FIG. 19, the bio-sensing apparatus 100G and the bio-sensing apparatus 100H respectively includes surface plasma resonance layers SPR. Functions of the surface plasma resonance layers SPR of the bio-sensing apparatus 100G and the bio-sensing apparatus 100H and a function of the surface plasma resonance layer SPR of the above bio-sensing apparatus 100 are the same, and which will not be repeated here.

Figure 22:
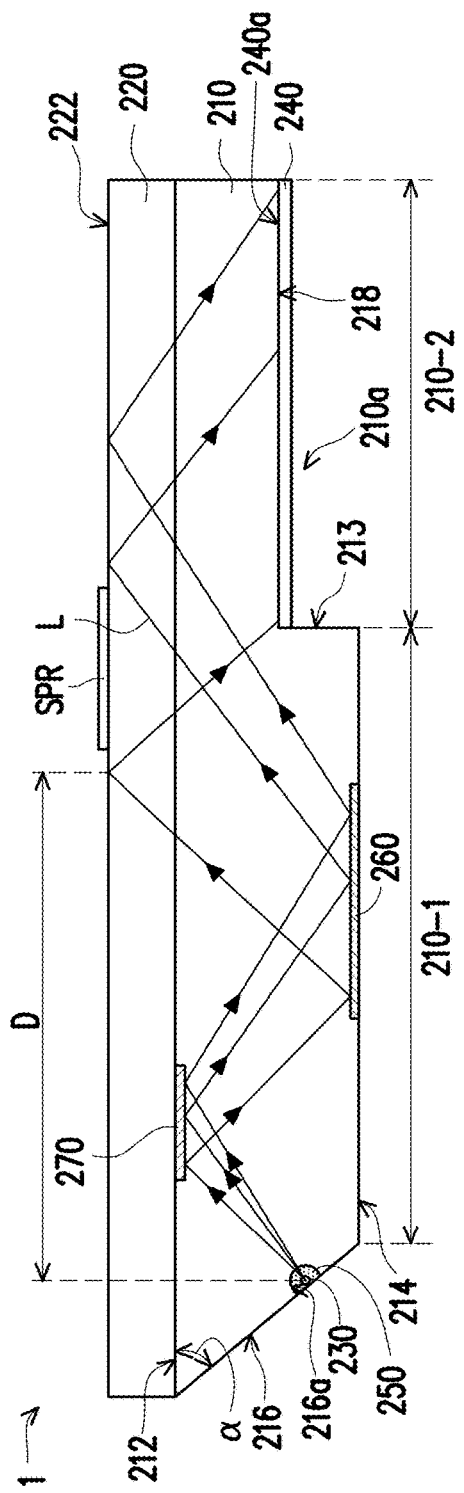
FIG. 22 is a schematic sectional view of a bio-sensing apparatus according to an embodiment of the invention.
Figure 23:
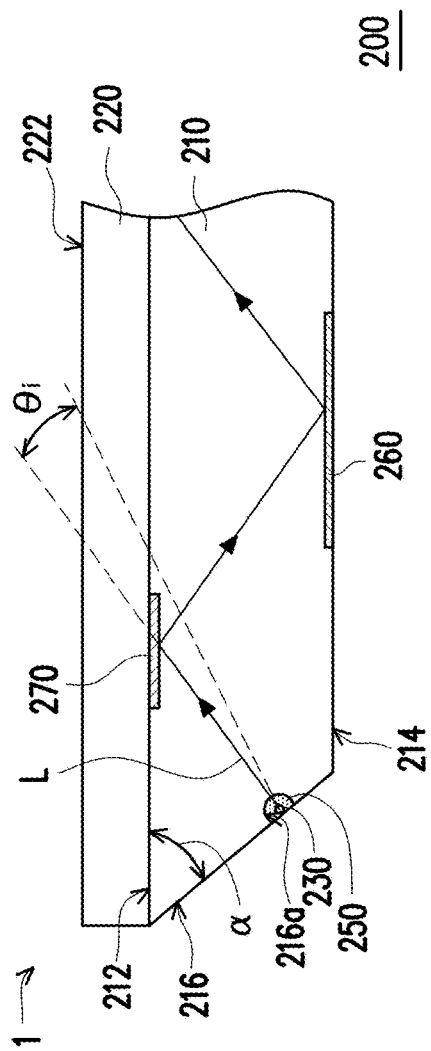
FIG. 23 is a schematic view of a part of the bio-sensing apparatus according to an embodiment of the invention.

FIG. 22 is a schematic sectional view of a bio-sensing apparatus according to an embodiment of the invention. FIG. 23 is a schematic view of a part of the bio-sensing apparatus according to an embodiment of the invention. Referring to FIG. 22 and FIG. 23, a bio-sensing apparatus 200 is located in an environment medium 1. In the present embodiment, the environment medium 1 is, for example, air. However, the invention is not limited thereto, and in another embodiment, the bio-sensing apparatus 200 may also be located in another type of environment medium. The bio-sensing apparatus 200 is used to capture an image of an object. In a normal condition, the object refers to a biological feature, e.g., a fingerprint, but the invention is not limited thereto.

The bio-sensing apparatus 200 includes a light guide 210. The light guide 210 includes a top surface 212, a bottom surface 214 opposite to the top surface 212, a light incident surface 216 connected between the top surface 212 and the bottom surface 214 and a light emitting surface 218. The light emitting surface 218 is opposite to the top surface 212. The bottom surface 214 is connected between the light incident surface 216 and the light emitting surface 218. Specially, the light incident surface 216 is inclined with respect to the top surface 212, and an acute angle α is included between the light incident surface 216 and the top surface 212.

In the present embodiment, the light guide 210 further includes an inner wall 213. The light emitting surface 218 is more adjacent to a light-transmitting element 120 than the bottom surface 214. The inner wall 213 is connected between the bottom surface 214 and the light emitting surface 218. A recess 210a is formed by the inner wall 213 and the light emitting surface 218. In other words, the light guide 210 includes a thick portion 210-1 having the bottom surface 214 and a thin portion 210-2 having the light emitting surface 218. In the present embodiment, the light emitting surface 218 and the bottom surface 214 may be selectively parallel to the top surface 110, but the invention is not limited thereto, and in another embodiment, the light emitting surface 218 may also be inclined with respect to the top surface 110, which will be described with reference to other drawings below.

The bio-sensing apparatus 200 includes the light-transmitting element 220. The light-transmitting element 220 is disposed on the top surface 212 of the light guide 210. In the present embodiment, the light-transmitting element 220 may be fixed onto the top surface 212 of the light guide 210 through an optical adhesive (not shown). A material of the light guide 210 and/or a material of the light-transmitting element 220 may be selected form glass, polymethylmethacrylate (PMMA), polycarbonate (PC) or other suitable transparent materials. In the present embodiment, refractive indices of the light guide 210, the optical adhesive and the light-transmitting element 220 may be the same or similar, but the invention is not limited thereto.

The bio-sensing apparatus 200 includes a light-emitting element 230. The light-emitting element 230 is disposed beside the light incident surface 216 and used to emit a light beam L. In the present embodiment, the light incident surface 216 of the light guide 210 has a recess 216a. The light-emitting element 230 is disposed in the recess 216a. The bio-sensing apparatus 200 further includes an optical adhesive 250. The optical adhesive 250 is filled in the recess 216a to cover the light-emitting element 230 and connect the light-emitting element 230 and the light guide 210. In the present embodiment, a refractive index of the optical adhesive 250 may by the same as or similar to the refractive index of the light guide 210 to reduce loss of the light beam L before entering the light guide 210, but the invention is not limited thereto. In the present embodiment, the light beam L is, for example, invisible light. Thereby, when an electronic product equipped with the bio-sensing apparatus 200 is used to capture the object image, the light beam L does not influence the appearance of the electronic product. However, the invention is not limited thereto, and in another embodiment, the light beam L may also be visible light or a combination of visible light and invisible light. In the present embodiment, the light-emitting element 230 is a light emitting diode (LED), but the invention is not limited thereto, and in another embodiment, the light-emitting element may also be other suitable light emitting devices.

The bio-sensing apparatus 200 includes a sensing element 240. The sensing element 240 is disposed on the light emitting surface 218 of the light guide 210. A light receiving surface 140a of the sensing element 240 faces the light emitting surface 218 of the light guide 210. In the present embodiment, the sensing element 240 is supported on the light emitting surface 218 of the light guide 210, and the light receiving surface 140a of the sensing element 240 may be substantially parallel to the light emitting surface 218 of the light guide 210. The sensing element 240 is, for example, a charge coupled device (CCD) or a complementary metal-oxide semiconductor (CMOS), but the invention is not limited thereto, and in another embodiment, the light-emitting element 140 may also be other suitable image sensors.

Referring to FIG. 22 and FIG. 23, the light beam L passing through the light incident surface 216 is transmitted toward the light-transmitting element 220, and at least a part of the light beam L is totally reflected by an interface 222 between the light-transmitting element 220 and the environment medium 1. When the object (e.g., convex parts of the fingerprint) contact the interface 222, the total reflection of the light beam L on a part of the interface 222 corresponding to the convex parts of the fingerprint may be destroyed, which leads the sensing element 240 to obtain dark lines corresponding to the convex parts of the fingerprint. Concave parts of the fingerprint does not contact the interface 222 while the convex parts of the fingerprint contact the part of the interface 222, and the total reflection of the light beam L on another part of the interface 222 corresponding to the concave parts of the fingerprint is not destroyed, which leads the sensing element 240 to obtain bright lines corresponding to the concave parts of the fingerprint. In this way, the sensing element 240 may obtain a bright and dark object image (e.g., a fingerprint image).

It should be noted that with the inclined light incident surface 216 (i.e., the design of the acute angle α), the light beam L emitted by the light-emitting element 230 may be totally reflected by the interface 222 between the light-transmitting element 220 and the environment medium 1 within a short distance k. In this way, the size of the bio-sensing apparatus 200 may be reduced, which is favorable for being installed in various electronic products. In the present embodiment, the size of the acute angle α may be adaptively designed, and thereby, a ratio of the total reflection of the light beam L occurring on the interface 222 may be further increased in a premise that the size of the bio-sensing apparatus 200 is reduced. For example, in the present embodiment, the acute angle α satisfies the following formula (1):

$$\theta_i \le \alpha - \sin^{-1}\left(\frac{n_1}{n_2}\right), \quad (1)$$

wherein $\theta_i$ is an incident angle of the light beam L entering the light guide 210 through the light incident surface 216, $n_1$ is a refractive index of the environment medium 1, and $n_2$ is the refractive index of the light guide 210. $\theta_i$ is negative if a direction from a normal line (e.g., the dotted line illustrated in FIG. 23 which is not parallel to the light beam L) of the light incident surface 216 to the light beam L is clockwise. $\theta_i$ is positive if the direction from the normal line (e.g., the dotted line illustrated in FIG. 23 which is not parallel to the light beam L) of the light incident surface 216 to the light beam L is counterclockwise. When the angle α satisfies the formula (1), the ratio of the total reflection of the light beam L occurring on the interface 222 is increased, which facilitates enhancing image capturing quality of the bio-sensing apparatus 200.

Referring to FIG. 22, in the present embodiment, the bio-sensing apparatus 200 may further include a second reflection device 270 and a first reflection device 260. The second reflection device 270 is disposed on the top surface 212 of the light guide 210 and located between the light-transmitting element 220 and the light guide 210. The first reflection device 260 is disposed on the bottom surface 214 of the light guide 210. The light beam L passing through the light incident surface 216 is sequentially reflected by the second reflection device 270 and the first reflection device 260 and expanded. The expanded light beam L is transmitted toward the light-transmitting element 220 and totally reflected by the interface 222 between the light-transmitting element 220 and the environment medium 1. The sensing element 240 is disposed more adjacently to the light-transmitting element 220 than the second reflection device 110 (for example, in the recess 210a).

It should be noted that with the beam expansion effect achieved by the second reflection device 270 and the first reflection device 260 and adjustment of a position of the sensing element (for example, the light receiving surface 140a of the sensing element 240 is configured to be adjacent to the light-transmitting element 220, or the light receiving surface 140a of the sensing element 240 is configured to be inclined with respect to the top surface 212), the sensing element 240 may capture a complete object image (e.g., a fingerprint image) by using the light receiving surface 140a with a small area. In other words, the area of the sensing element 240 can be reduced, and the size of the bio-sensing apparatus 200 including the sensing element 240 may be further reduced. However, the invention is not limited thereto, and in another embodiment, the bio-sensing apparatus 200 may not have to include the second reflection device 270 and the first reflection device 260, which will be described with reference to other drawings below.

Figure 24:
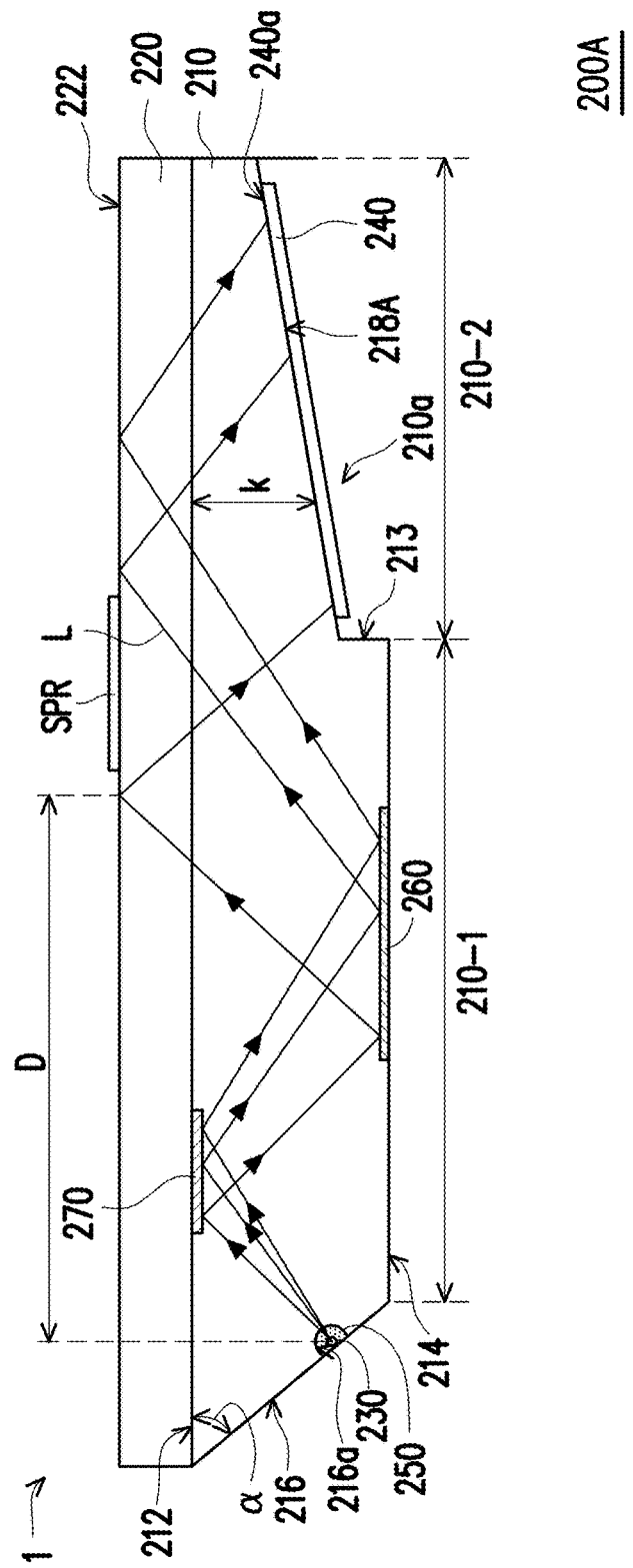
FIG. 24 is a schematic sectional view of a bio-sensing apparatus according to another embodiment of the invention.

FIG. 24 is a schematic sectional view of a bio-sensing apparatus according to another embodiment of the invention. Referring to FIG. 24, a bio-sensing apparatus 200A of the present embodiment is similar to the bio-sensing apparatus 200 described above, and thus, the same or corresponding elements are labeled by the same or corresponding numerals. The difference between the bio-sensing apparatus 200A and the bio-sensing apparatus 200 lies in a light emitting surface 218A of the bio-sensing apparatus 200A being different from that of the bio-sensing apparatus 200. The difference will be described below, and the same or corresponding parts may refer to the description above.

Referring to FIG. 24, the bio-sensing apparatus 200A includes the light guide 210, the light-transmitting element 220, the light-emitting element 230 and the sensing element 240. The light guide 210 includes the top surface 212, the bottom surface 214 opposite to the top surface 212, the light incident surface 216 connected between the top surface 212 and the bottom surface 214 and the light emitting surface 218A. The light emitting surface 218A is opposite to the top surface 212. The bottom surface 214 is connected between the light incident surface 216 and the light emitting surface 218A. An acute angle α is included between the light incident surface 216 and the top surface 212. The light-transmitting element 220 is disposed on the top surface 212 of the light guide 210. The light-emitting element 230 is disposed beside the light incident surface 216 and used to emit the light beam L. The light beam L passing through the light incident surface 216 is transmitted toward the light-transmitting element 220 and totally reflected by the interface 222 between the light-transmitting element 220 and the environment medium 1. The sensing element 240 is disposed on the light emitting surface 218A of the light guide 210.

Being different from that of the bio-sensing apparatus 200, the light emitting surface 218A of the bio-sensing apparatus 200A is inclined with respect to the top surface 212 and the bottom surface 214, and a distance k between the top surface 212 and the light emitting surface 218A is gradually decreased as being far away from the light-emitting element 230. The sensing element 240 is supported on the light emitting surface 218A, and the light receiving surface 240a of the sensing element 240 may be substantially parallel to the light emitting surface 218A of the light guide 210. The light receiving surface 240a of the sensing element 240 is also inclined with respect to the top surface 212 and the bottom surface 214. In addition to the effects and advantages of the bio-sensing apparatus 200, the bio-sensing apparatus 200A may also achieve reducing a probability of stray light entering the sensing element 240 with the inclined sensing element 240, so as to enhance quality of capturing the object image, for example, enhance a contrast of the object image.

Figure 25:
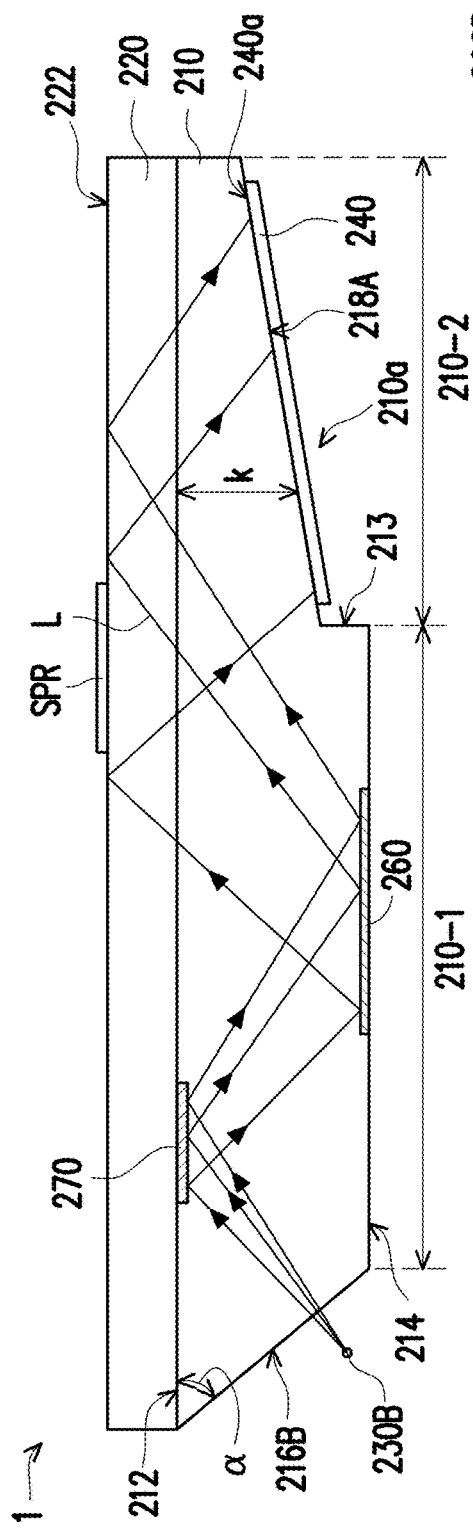
FIG. 25 is a schematic sectional view of a bio-sensing apparatus according to an embodiment of the invention.
Figure 26:
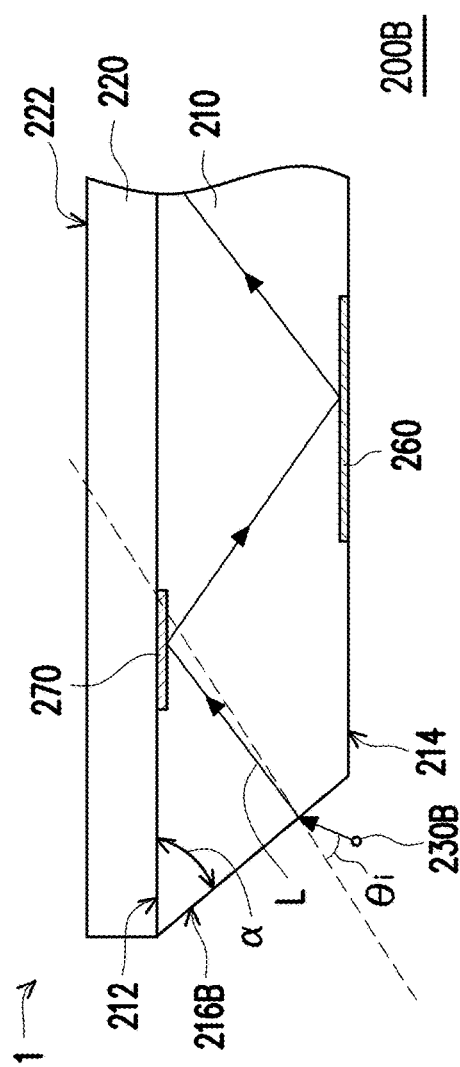
FIG. 26 is a schematic view of a part of the bio-sensing apparatus according to an embodiment of the invention.

Referring to FIG. 25 and FIG. 26, the bio-sensing apparatus 200B includes the light guide 210, the light-transmitting element 220, the light-emitting element 230B and the sensing element 240. The light guide 210 includes the top surface 212, the bottom surface 214 opposite to the top surface 212, a light incident surface 216B connected between the top surface 212 and the bottom surface 214 and the light emitting surface 218A. The light emitting surface 218A is opposite to the top surface 212. The bottom surface 214 is connected between the light incident surface 216B and the light emitting surface 218A. An acute angle α is included between the light incident surface 216B and the top surface 212. The light-transmitting element 220 is disposed on the top surface 212 of the light guide 210. The light-emitting element 230B is disposed beside the light incident surface 216 and used to emit the light beam L. The light beam L passing through the light incident surface 216B is transmitted toward the light-transmitting element 220 and totally reflected by the interface 222 between the light-transmitting element 220 and the environment medium 1. The sensing element 240 is disposed on the light emitting surface 218A of the light guide 210.

Being different from that of the bio-sensing apparatus 200A, the light incident surface 216B of the bio-sensing apparatus 200B does not have the recess 216a, and the light-emitting element 230B is disposed outside the light guide 210 and located in the environment medium 1. In other words, the light beam L emitted by the light-emitting element 230B has to be transmitted for a distance in the environment medium 1 and then, enters the light guide 210 through the light incident surface 216B. As the transmission path of the light beam L changes, a preferable range of the acute angle α in the bio-sensing apparatus 200B is also different from the preferable range of the acute angle α in the bio-sensing apparatus 200A. Specifically, in the bio-sensing apparatus 200B, the acute angle α satisfies the following formula (2):

$$\theta_i \leq \sin^{-1}\left\{\frac{n_2}{n_1}\sin\left[\alpha - \sin^{-1}\left(\frac{n_1}{n_2}\right)\right]\right\}, \tag{2}$$

wherein $\theta_i$ is an angle of the light beam L entering the light incident surface 216B, $n_1$ is the refractive index of the environment medium 1, and $n_2$ is the refractive index of the light guide 210. $\theta_i$ is negative if the direction from the normal line (e.g., the dotted line illustrated in FIG. 26) of the light incident surface 216B to the light beam L is clockwise. $\theta_i$ is positive if the direction from the normal line (e.g., the dotted line illustrated in FIG. 26) of the light incident surface 216B to the light beam L is counterclockwise. The bio-sensing apparatus 200B has effects and advantages similar to the bio-sensing apparatus 200A and will not be repeated.

Figure 27:
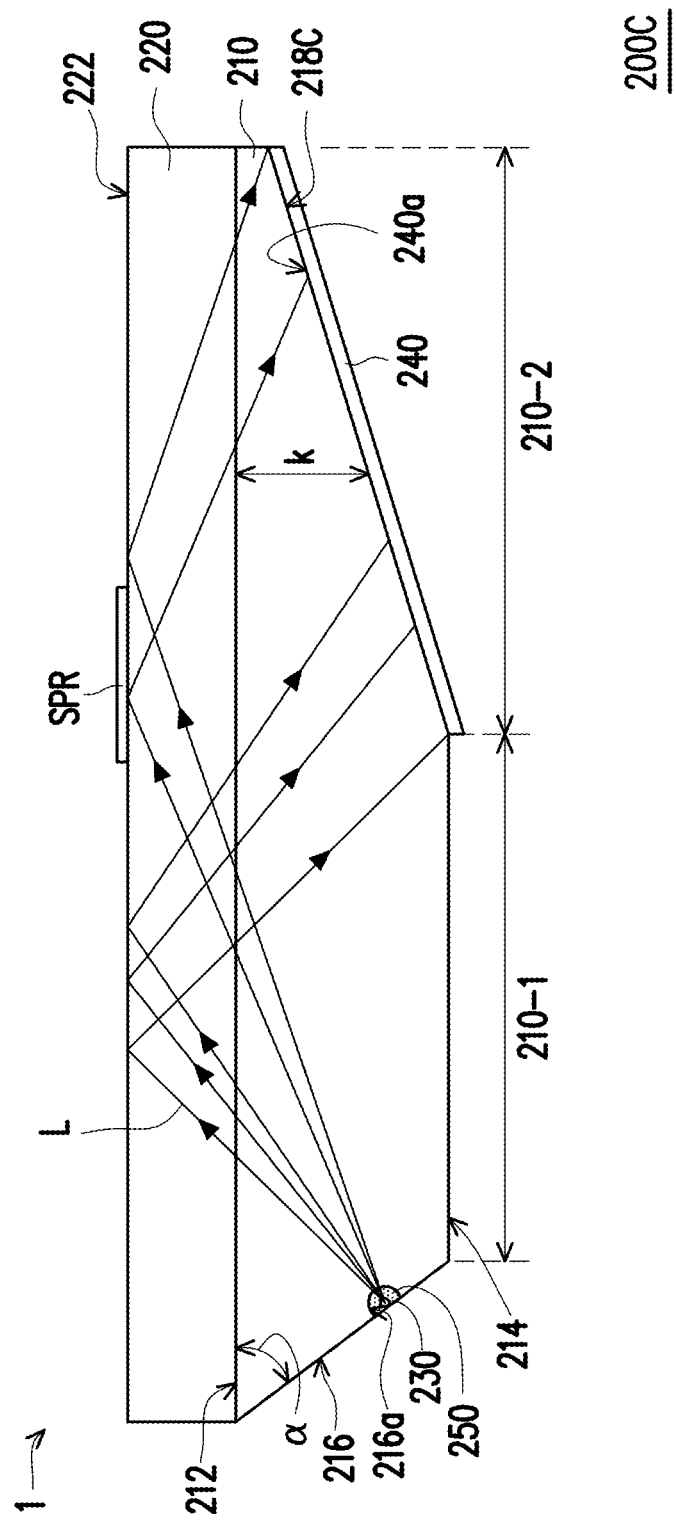
FIG. 27 is a schematic sectional view of a bio-sensing apparatus according to an embodiment of the invention.

FIG. 27 is a schematic sectional view of a bio-sensing apparatus according to still an embodiment of the invention. Referring to FIG. 27, a bio-sensing apparatus 200C of the present embodiment is similar to the bio-sensing apparatus 200A described above, and thus, the same or corresponding elements are labeled by the same or corresponding numerals. The difference between the bio-sensing apparatus 200C and the bio-sensing apparatus 200A lies in that the bio-sensing apparatus 200C may not have to include the second reflection device 270 and the first reflection device 260, and the light guide 210 of the bio-sensing apparatus 200C may not have to have the inner wall 213. The difference will be described below, and the same or corresponding parts may refer to the description above.

Referring to FIG. 27, the bio-sensing apparatus 200C includes the light guide 210, the light-transmitting element 220, the light-emitting element 230 and the sensing element 240. The light guide 210 includes the top surface 212, the bottom surface 214 opposite to the top surface 212, the light incident surface 216 connected between the top surface 212 and the bottom surface 214 and a light emitting surface 218C. The light emitting surface 218C is opposite to the top surface 212. The bottom surface 214 is connected between the light incident surface 216 and the light emitting surface 218C. The light emitting surface 218C is inclined with respect to the top surface 212, and a distance d between the top surface 212 and the light emitting surface 218C is gradually decreased as being far away from the light-emitting element 230. An acute angle α is included between the light incident surface 216 and the top surface 212. The light-transmitting element 220 is disposed on the top surface 212 of the light guide 210. The light-emitting element 230 is disposed beside the light incident surface 216 and used to emit the light beam L. The light beam L passing through the light incident surface 216 is transmitted toward the light-transmitting element 220 and totally reflected by the interface 222 between the light-transmitting element 220 and the environment medium 1. The sensing element 240 is disposed on the light emitting surface 218C of the light guide 210. The sensing element 240 is supported on the light emitting surface 218C, and the light receiving surface 240a of the sensing element 240 may be substantially parallel to the light emitting surface 218C of the light guide 210. In other words, the light receiving surface 240a of the sensing element 240 is also inclined.

Being different from that of the bio-sensing apparatus 200A, the light guide 210 of the bio-sensing apparatus 200C may not have the inner wall 213, and the light emitting surface 218C of the light guide 210 may be directly connected with the bottom surface 214. Additionally, the bio-sensing apparatus 200C may not have to include the second reflection device 270 and the first reflection device 260, and the light beam L passing through the light incident surface 216 may be directly transmitted toward the light-transmitting element 220 and totally reflected by the interface 222 between the light-transmitting element 220 and the environment medium 1. In other words, with the use of one reflection (i.e., the total reflection of the light beam L on the interface 222) and the inclined sensing element 240, the size of the bio-sensing apparatus 200C may also be reduced while the second reflection device 270 and the first reflection device 260 do not have to be disposed.

Figure 28:
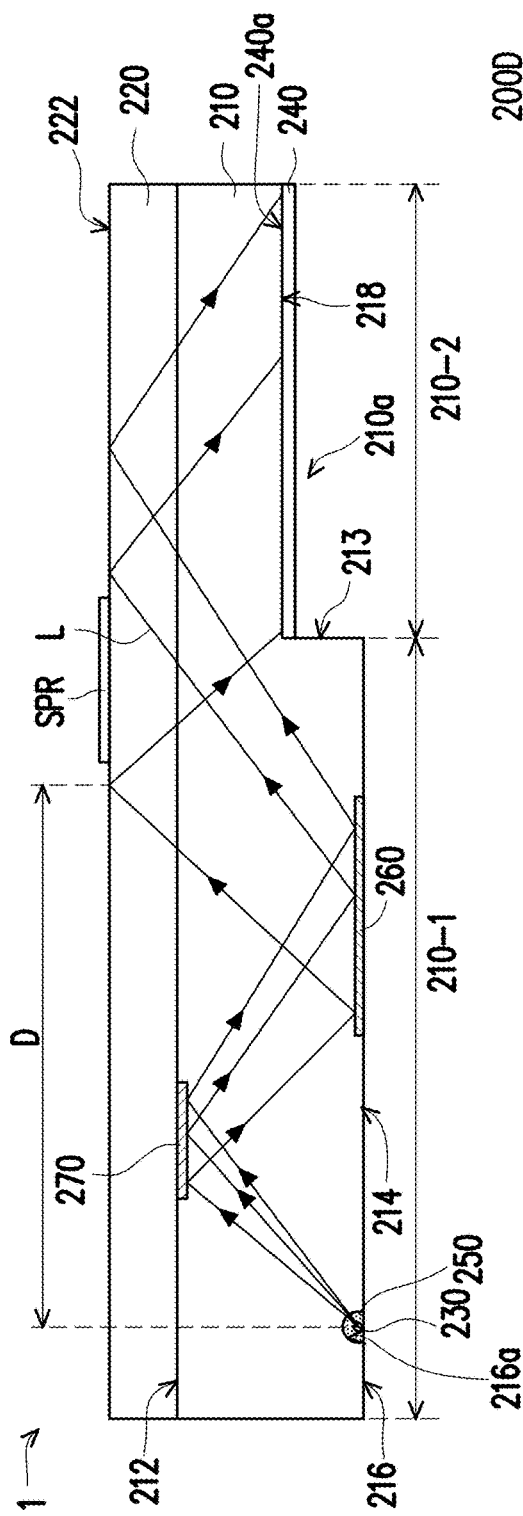
FIG. 28 is a schematic sectional view of a bio-sensing apparatus according to an embodiment of the invention.
Figure 29:
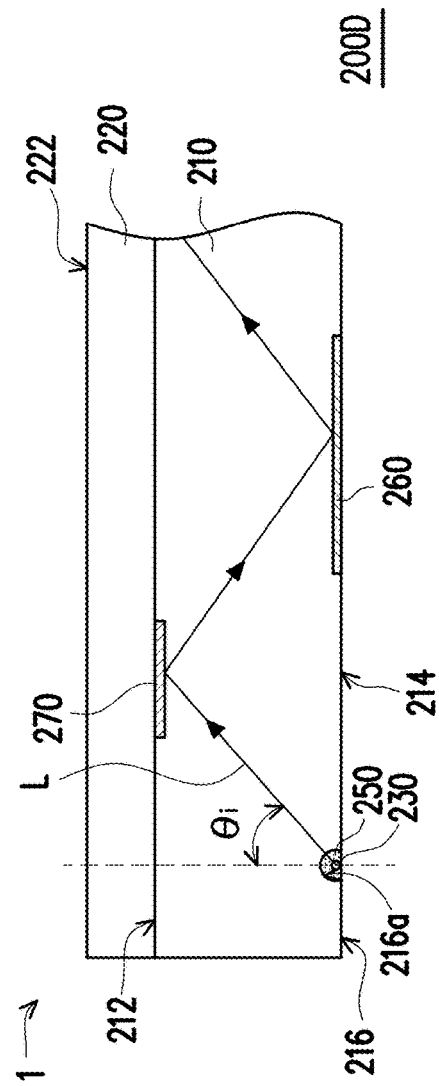
FIG. 29 is a schematic view of a part of the bio-sensing apparatus according to an embodiment of the invention.

FIG. 28 is a schematic sectional view of a bio-sensing apparatus according to an embodiment of the invention. FIG. 29 is a schematic view of a part of the bio-sensing apparatus according to an embodiment of the invention. Referring to FIG. 28 and FIG. 29, a bio-sensing apparatus 200D of the present embodiment is similar to the bio-sensing apparatus 200 described above, and thus, the same or corresponding elements are labeled by the same or corresponding numerals. The difference between the bio-sensing apparatus 200D and the bio-sensing apparatus 200 lies in the light incident surface 216 of the bio-sensing apparatus 200D being disposed on the bottom of the light guide 210. The difference will be described below, and the same or corresponding parts may refer to the description above.

Referring to FIG. 28 and FIG. 29, the bio-sensing apparatus 200D includes the light guide 210, the light-transmitting element 220, the light-emitting element 230 and the sensing element 240, the second reflection device 270 and the first reflection device 260. The light guide 210 includes the top surface 212, the bottom surface 214 opposite to the top surface 212, the light incident surface 216 connected between the top surface 212 and the bottom surface 214 and the light emitting surface 218. The light emitting surface 218 is opposite to the top surface 212. The bottom surface 214 is connected between the light incident surface 216 and the light emitting surface 218. The light-transmitting element 220 is disposed on the top surface 212 of the light guide 210. The light-emitting element is used to emit the light beam L. The sensing element 240 is disposed on the light emitting surface 218 of the light guide 210. The second reflection device 270 is disposed on the top surface 212 of the light guide 210 and located between the light-transmitting element 220 and the light guide 210. The first reflection device 260 is disposed on the bottom surface 214 of the light guide 210. The light beam L passing through the light incident surface 216 is reflected by the second reflection device 270 and the first reflection device 260. The light beam L reflected by the second reflection device 270 and the first reflection device 260 is totally reflected by the interface 222 between the light-transmitting element 220 and the environment medium 1.

Being different from that of the bio-sensing apparatus 200, the light incident surface 216 of the bio-sensing apparatus 200D is disposed on the bottom of the light guide 210. In other words, a part of the light incident surface 216 may substantially coplanar with the bottom surface 214, but the invention is not limited thereto. In the present embodiment, $\theta_i$ is an incident angle of the light beam L entering the light guide 210 through the light incident surface 216, and $\theta_i$ satisfies the following formula (3):

$$\theta_i \leq \pi - \sin^{-1}\left(\frac{n_1}{n_2}\right), \quad (3)$$

wherein $n_1$ is the refractive index of the environment medium, and $n_2$ is the refractive index of the light guide 210. $\theta_i$ is negative if the direction from the normal line (e.g., the dotted line illustrated in FIG. 29) of the light incident surface 216 to the light beam L is clockwise. $\theta_i$ is positive if the direction from the normal line (e.g., the dotted line illustrated in FIG. 29) of the light incident surface 216 to the light beam L is counterclockwise. The bio-sensing apparatus 200D has effects and advantages similar to the bio-sensing apparatus 200 and will not be repeated.

Figure 30:
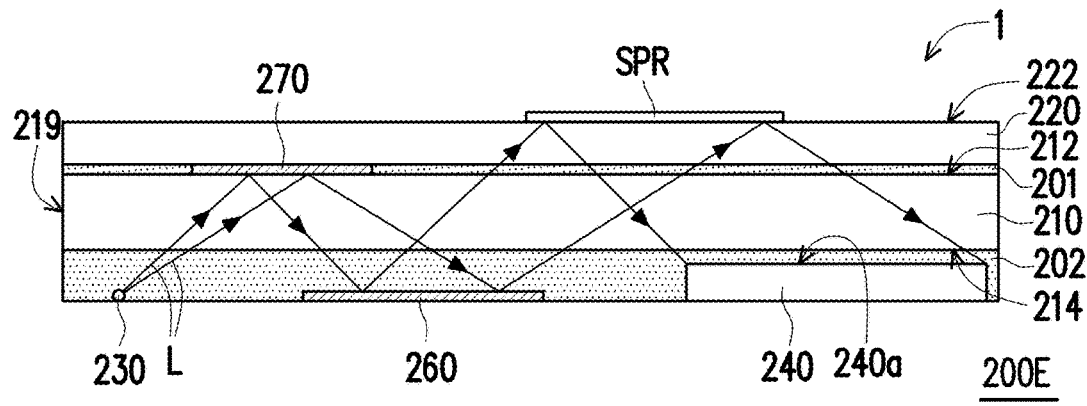
FIG. 30 is a schematic sectional view of a bio-sensing apparatus according to an embodiment of the invention.

FIG. 30 is a cross-sectional view of a bio-sensing apparatus according to an exemplary embodiment of the invention. Referring to FIG. 30, the bio-sensing apparatus 200 includes a light guide 210. The light guide 210 has a top surface 212 and a bottom surface 214 disposed opposite to each other. The light guide 210 further has a sidewall 219 connected between the top surface 212 and the bottom surface 214. In the present exemplary embodiment, the sidewall 219 is not incline relative to the top surface 212. In other words, the sidewall 219 is approximately perpendicular to the top surface 212. Though the invention is not limited thereto, and in other embodiments, the sidewall 219 can also be tilted relative to the top surface 212. In the present embodiment, a refractive index of the light guide 210 can be greater than or equal to 1.4 and smaller than or equal to 1.6. A material of the light guide 210 is, for example, glass, though the invention is not limited thereto, and in other embodiments, the material of the light guide 210 can also be other proper materials, for example, polymethylmethacrylate (PMMA), polycarbonate (PC) or other suitable transparent materials.

The bio-sensing apparatus 200 includes a light-transmitting element 220. The light-transmitting element 220 is disposed on the top surface 212 of the light guide 210. The light-transmitting element 220 has a surface 222 back-facing to the light guide 210. In the present embodiment, if the bio-sensing apparatus 200 is used for capturing a fingerprint and/or a finger vein, the surface 222 of the light-transmitting element 220 can be pressed by a finger.

The bio-sensing apparatus 200 includes a first optical adhesive 201. The first optical adhesive 201 is disposed between the light-transmitting element 220 and the top surface 212 of the light guide 210. The light-transmitting element 220 is connected to the top surface 212 of the light guide 210 through the first optical adhesive 201. In the present embodiment, the first optical adhesive 201 may have a refractive index the same or similar with that of the light guide 210 and/or the light-transmitting element 220, so as to reduce a loss of a light beam L at a boundary of the first optical adhesive 201 and the light guide 210 and/or a boundary of the first optical adhesive 201 and the light-transmitting element 220. In other words, the refractive index of the first optical adhesive 201 may also be greater than or equal to 1.4 and smaller than or equal to 1.6, though the invention is not limited thereto.

The bio-sensing apparatus 200E includes a sensing element 240. The sensing element 240 is disposed on the bottom surface 214 of the light guide 210. The light guide 210 is located between the light-transmitting element 220 and the sensing element 240. The sensing element 240 has a light receiving surface 240a facing to the light guide 210.

The bio-sensing apparatus 200E includes a second optical adhesive 202. The second optical adhesive 202 is disposed between the bottom surface 214 of the light guide 210 and the sensing element 240. The sensing element 240 is connected to the bottom surface 214 of the light guide 210 through the second optical adhesive 202. In the present embodiment, the second optical adhesive 202 may have a refractive index the same or similar with that of the light guide 210, so as to reduce a loss of the light beam L at a boundary of the second optical adhesive 202 and the light guide 210. In other words, the refractive index of the second optical adhesive 202 may also be greater than or equal to 1.4 and smaller than or equal to 1.6, though the invention is not limited thereto.

A material of the light guide 210 is different to a material of the first optical adhesive 201 and a material of the second optical adhesive 202. In other words, the light guide 210 with a lower material cost can be inserted between the light-transmitting element 220 and the sensing element 240 to reduce a usage amount of the optical adhesives filled between the light-transmitting element 220 and the sensing element 240. Since the usage amount of the first optical adhesive 201 and the second optical adhesive 202 with a high material cost is reduced, manufacturing cost of the bio-sensing apparatus 200E is reduced.

he bio-sensing apparatus 200E includes a light-emitting element 230. The light-emitting element 230 is adapted to emit the light beam L. The light beam L passed through the light guide 210 is transmitted toward the light-transmitting element 220, and is totally reflected by an interface (i.e. the surface 222) between the light-transmitting element 220 and the environment medium 1. When an object (for example, fingerprint convex portions) contacts the surface 222, the total reflection of the light beam L is spoiled on a part of the surface 222 corresponding to the fingerprint convex portions, such that the sensing element 240 obtains dark stripes corresponding to the fingerprint convex portions. While the fingerprint convex portions touch a part of the surface 222, fingerprint concave portions do not contact the surface 222, and the total reflection of the light beam L is not spoiled on another part of the surface 222 corresponding to the fingerprint concave portions, such that the sensing element 240 obtains bright stripes corresponding to the fingerprint concave portions. In this way, the sensing element 240 may obtain an object image (for example, a fingerprint image) with spaced bright and dark stripes. In the present embodiment, the light beam L is, for example, a visible light. However, the invention is not limited thereto, and in other embodiments, the light beam L can also be an invisible light or a combination of the invisible light and the visible light. The light-emitting element 230 is, for example, a light-emitting diode, though the invention is not limited thereto, and in other embodiments, the light-emitting element 230 can also be other suitable types of light-emitting device.

In the present exemplary embodiment, the bio-sensing apparatus 200E may further include a second reflecting device 270 and a first reflecting element 260. The second reflecting device 270 is disposed on the top surface 212 of the light guide 210. The second reflecting device 270 is located between the light-transmitting element 220 and the light guide 210. The first reflecting element 260 is disposed on the bottom surface 214 of the light guide 210. The light guide 210 is located between the second reflecting device 270 and the first reflecting element 260. The light beam L reflected by the second reflecting device 270 and the first reflecting element 260 is transmitted toward the light-transmitting element 220, and is totally reflected by the interface (i.e. the surface 222) between the light-transmitting element 220 and the environment medium 1. For example, in the present embodiment, the second reflecting device 270 and the first reflecting element 260 can be reflectors or reflecting layers formed by a coating method, which is not limited by the invention.

In the present embodiment, the light beam L is transmitted toward the top surface 212 of the light guide 210 before being transmitted to the second reflecting device 270 and the first reflecting element 260, and the light beam L can be sequentially reflected by the second reflecting device 270 and the first reflecting element 260, and transmitted to the light-transmitting element 220. However, the invention is not limited thereto, and in other embodiments, the light beam L can also be transmitted along other paths. Moreover, in the present embodiment, the second reflecting device 270 and the first reflecting element 260 can be staggered and partially overlapped. However, the invention is not limited thereto, and in other embodiments, the second reflecting device 270 and the first reflecting element 260 can be completely staggered without being overlapped, or can be configured in other suitable relative positions, which are described with reference of FIG. 31 and FIG. 32.

Figure 31:
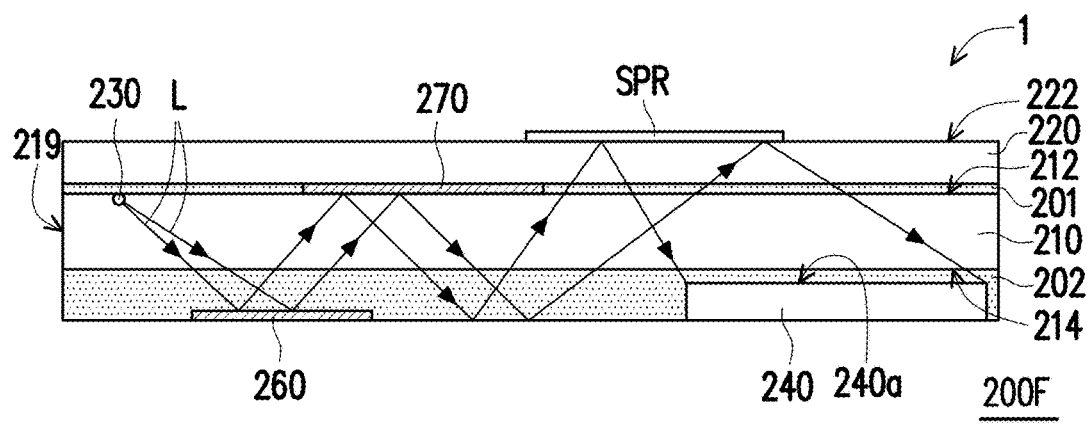
FIG. 31 is a schematic sectional view of a bio-sensing apparatus according to an embodiment of the invention.

FIG. 31 is a cross-sectional view of a bio-sensing apparatus according to an exemplary embodiment of the invention. The bio-sensing apparatus 200F of FIG. 31 is similar to the bio-sensing apparatus 200 of FIG. 30, so that the same or similar devices are denoted by the same or similar referential numbers. A difference between the bio-sensing apparatus 200F and the bio-sensing apparatus 200E is that in the embodiment of FIG. 31, the light beam L can be transmitted toward the bottom surface 214 of the light guide 210 before being transmitted to the second reflecting device 270 and the first reflecting element 260, and the light beam L can be sequentially reflected by the first reflecting element 260 and the second reflecting device 270, and transmitted to the light-transmitting element 220. For example, in the present embodiment, the second reflecting device 270 and the first reflecting element 260 can be reflectors or reflecting layers formed by a coating method, which is not limited by the invention. Moreover, in other embodiments, a reflection function of the first reflecting element 260 can also be replaced by an interface between the second optical adhesive 202 and an external air layer, where a refractive index of the second optical adhesive 202 is different to a refractive index of the external air layer.

Figure 32:
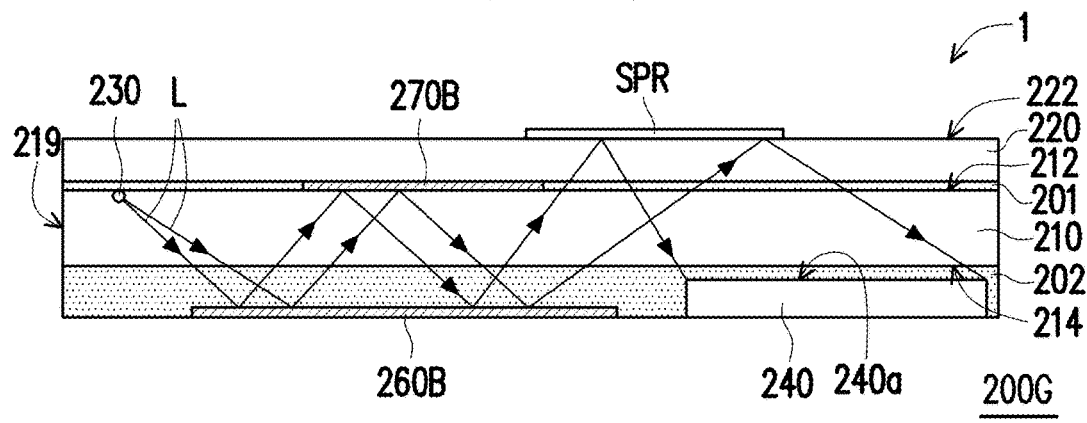
FIG. 32 is a schematic sectional view of a bio-sensing apparatus according to an embodiment of the invention.

FIG. 32 is a cross-sectional view of a bio-sensing apparatus according to an embodiment of the invention. The bio-sensing apparatus 200G of FIG. 32 is similar to the bio-sensing apparatus 200F of FIG. 31, so that the same or similar devices are denoted by the same or similar referential numbers. A difference between the bio-sensing apparatus 200G and the bio-sensing apparatus 200F is that in the embodiment of FIG. 32, the second reflecting element 270B and the first reflecting element 260B are not partially overlapped. In detail, the second reflecting element 270B may be located within an area of the first reflecting element 260B. In other words, an orthogonal projection of the second reflecting element 270B on the bottom surface 214 is completely located within an orthogonal projection of the first reflecting element 260B on the bottom surface 214. The light beam L can be sequentially reflected by a front end of the first reflecting element 260B, the second reflecting element 270B and a back end of the first reflecting element 260B, and transmitted to the light-transmitting element 220.

Figure 33:
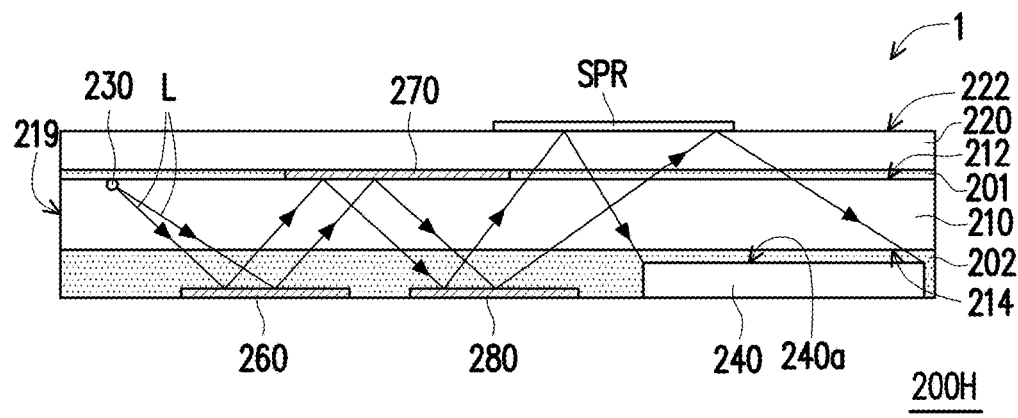
FIG. 33 is a schematic sectional view of a bio-sensing apparatus according to an embodiment of the invention.

FIG. 33 is a cross-sectional view of a bio-sensing apparatus according to an exemplary embodiment of the invention. The bio-sensing apparatus 200H of FIG. 33 is similar to the bio-sensing apparatus 200F of FIG. 31, so that the same or similar devices are denoted by the same or similar referential numbers. A difference between the bio-sensing apparatus 200H and the bio-sensing apparatus 200F is that the bio-sensing apparatus 200H of FIG. 33 further includes a third reflecting device 280. The third reflecting device 280 is disposed on the bottom surface 214 of the light guide 210. The light beam L is sequentially reflected by the first reflecting element 260, the second reflecting device 270 and the third reflecting device 280, and transmitted to the light-transmitting element 220. The first reflecting element 260 and the third reflecting device 280 can be separated. The first reflecting element 260 and the second reflecting device 270 are partially overlapped. In detail, the first reflecting element 260 is overlapped with a front end of the second reflecting device 270 and is not overlapped with a back end of the second reflecting device 270. The third reflecting device 280 and the second reflecting device 270 are partially overlapped. In detail, the third reflecting device 280 is overlapped with the back end of the second reflecting device 270 and is not overlapped with the front end of the second reflecting device 270. Moreover, the first reflecting element 260, the third reflecting device 280 or the sensing element 240 shown in FIG. 33 are not necessarily disposed in the second optical adhesive 202. In other embodiments, the first reflecting element 260, the third reflecting device 280 or the sensing element 240 may also be disposed on the bottom surface 214 of the light guide 210. In other words, the first reflecting element 260, the third reflecting device 280 or the sensing element 240 may also be disposed at another side of the second optical adhesive 202.

It should be noted that in any embodiments of FIG. 30 to FIG. 33, the light guide 210 has the sidewall 219 connected between the top surface 212 and the bottom surface 214, and a light absorbing layer (not shown) can be configured on the sidewall 219.

Figure 34:
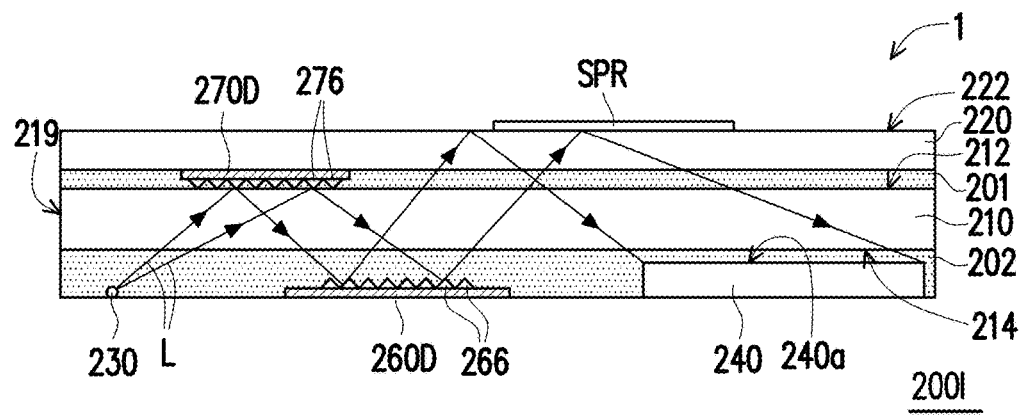
FIG. 34 is a schematic sectional view of a bio-sensing apparatus according to an embodiment of the invention.

FIG. 34 is a cross-sectional view of a bio-sensing apparatus according to an exemplary embodiment of the invention. The bio-sensing apparatus 200I of FIG. 34 is similar to the bio-sensing apparatus 200E of FIG. 30, so that the same or similar devices are denoted by the same or similar referential numbers. A difference between the bio-sensing apparatus 200I and the bio-sensing apparatus 200E is that in the embodiment of FIG. 34, at least one of the second reflecting device 270D and the first reflecting element 260D has one or a plurality of optical microstructures 276, 266. For example, both of the second reflecting device 270D and the first reflecting element 260D may selectively have one or a plurality of optical microstructures 276, 266. In an example of the present embodiment, the plurality of optical microstructures 276, 266 can be configured on the second reflecting device 270D and/or the first reflecting element 260D in a manner of continuous or interval configuration. In overall, the optical microstructures of the specification can be comprehensively or partially configured on any one of the reflecting devices. Moreover, the optical microstructures are not limited to be configured in continuous configuration or interval configuration. The light beam L can be reflected by one or a plurality of optical microstructures 276 of the second reflecting device 270D and/or one or a plurality of optical microstructures 266 of the first reflecting element 260D, and transmitted to the light-transmitting element 220. In the present embodiment, the optical microstructures 276 can be comprehensively (or partially) configured on the second reflecting device 270D, and the optical microstructures 266 can be comprehensively (or partially) configured on the first reflecting element 260D. Moreover, a function of configuring the optical microstructures 276 and/or the first reflecting element 260D is to increase an image capturing area and make the light beam L transmitted to the sensing element 240 to be more uniform, which avails an imaging effect.

Figure 35:
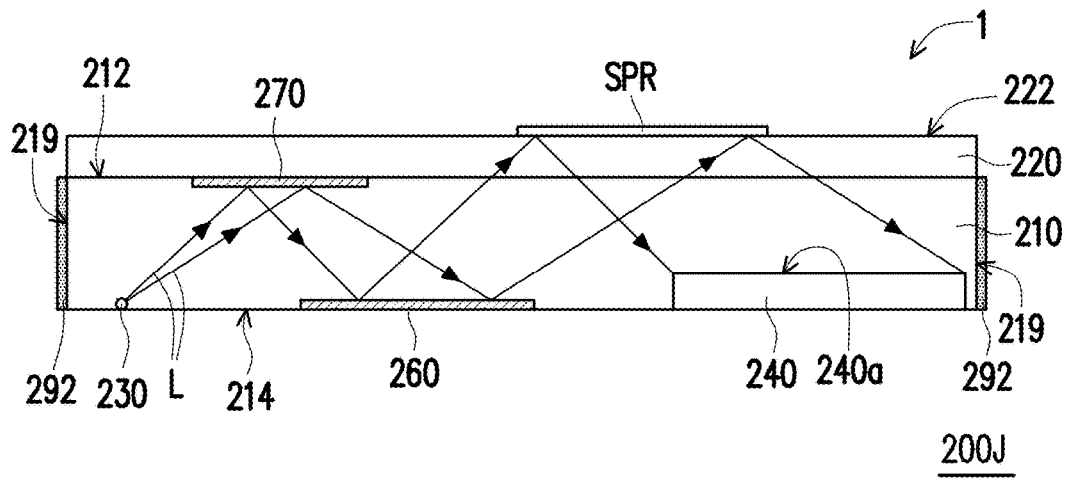
FIG. 35 is a schematic sectional view of a bio-sensing apparatus according to an embodiment of the invention.
Figure 36:
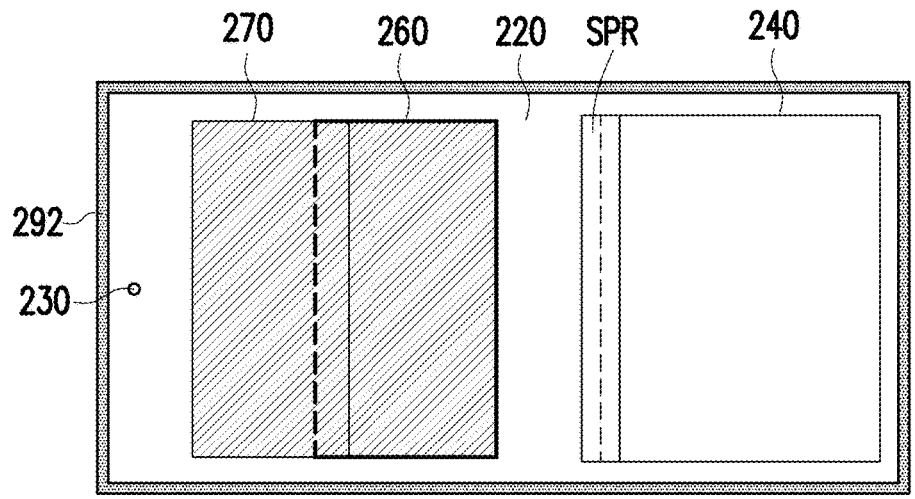
FIG. 36 is a top view of the bio-sensing apparatus of FIG. 35.

FIG. 35 is a cross-sectional view of a bio-sensing apparatus according to an exemplary embodiment of the invention. FIG. 36 is a top view of the bio-sensing apparatus of FIG. 35. The bio-sensing apparatus 200J of FIG. 35 and FIG. 36 is similar to the bio-sensing apparatus 200E of FIG. 30, so that the same or similar devices are denoted by the same or similar referential numbers. A difference between the bio-sensing apparatus 200J and the bio-sensing apparatus 200E is that the bio-sensing apparatus 200J further includes a light absorbing layer 292. The light absorbing layer 292 may absorb light. In other words, the light absorbing layer 292 can be an opaque and non-reflective light-shielding layer. The light absorbing layer 292 covers the sidewall 219 of the light guide 210. The light absorbing layer 292 can absorb a stray light L incident to the sidewall 219 to improve the image capturing quality of the bio-sensing apparatus 200J. In the present embodiment, the light absorbing layer 292 can be an ink layer or an adhesive member, though the invention is not limited thereto, and in other embodiments, the light absorbing layer 292 can be other suitable light absorbing materials.

Figure 37:
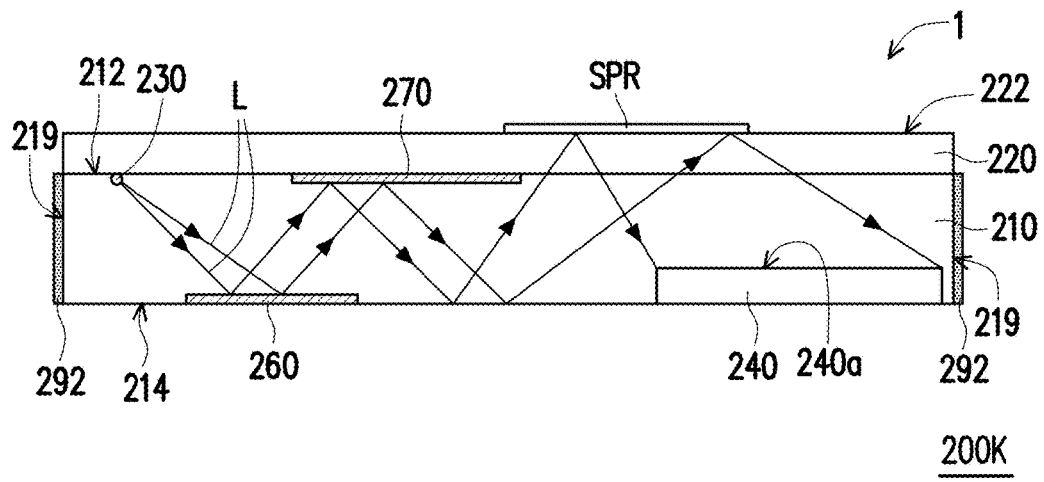
FIG. 37 is a cross-sectional view of a bio-sensing apparatus according to an exemplary embodiment of the invention.
Figure 38:
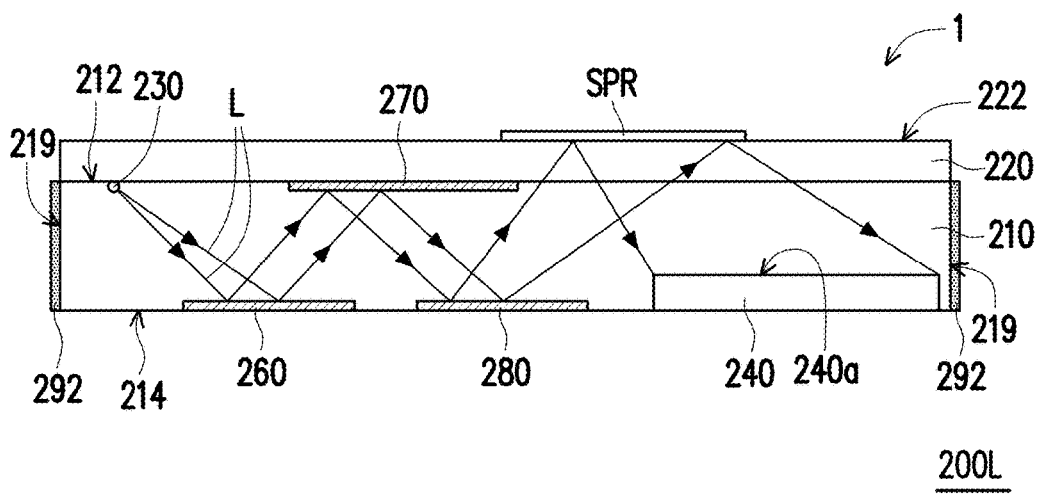
FIG. 38 is a cross-sectional view of a bio-sensing apparatus according to an embodiment of the invention.
Figure 39:
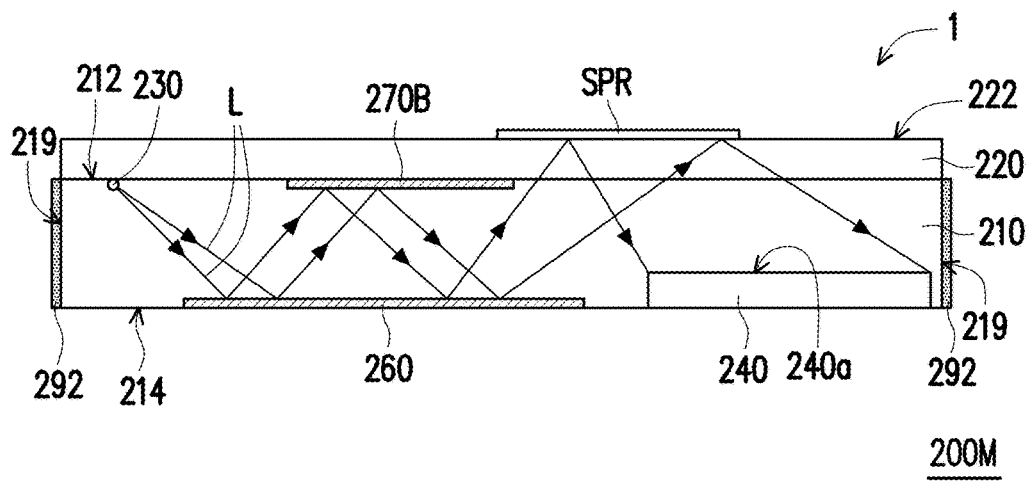
FIG. 39 is a cross-sectional view of a bio-sensing apparatus according to an embodiment of the invention.
Figure 40:
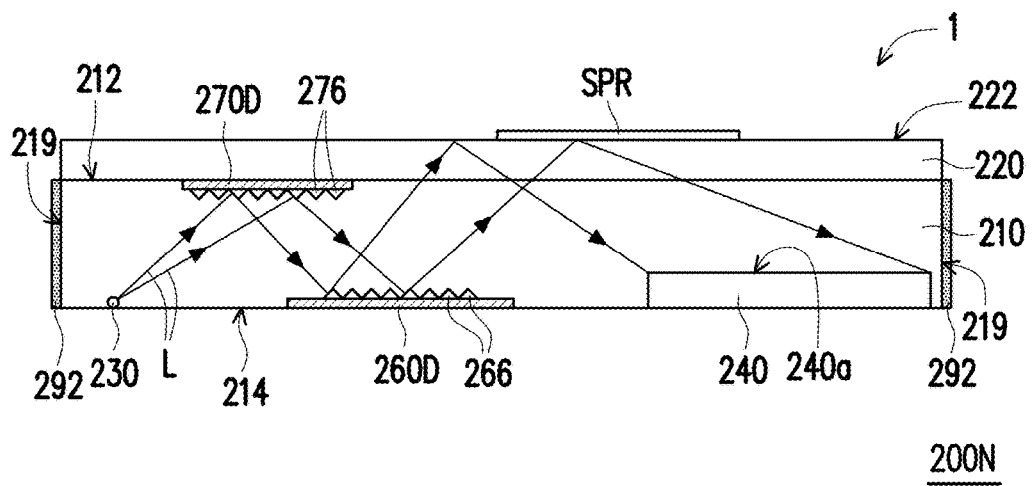
FIG. 40 is a cross-sectional view of a bio-sensing apparatus according to an exemplary embodiment of the invention.

FIG. 37 is a cross-sectional view of a bio-sensing apparatus according to an exemplary embodiment of the invention. FIG. 38 is a cross-sectional view of a bio-sensing apparatus according to an embodiment of the invention. FIG. 39 is a cross-sectional view of a bio-sensing apparatus according to an embodiment of the invention. FIG. 40 is a cross-sectional view of a bio-sensing apparatus according to an exemplary embodiment of the invention. The bio-sensing apparatuses 200K, 200L, 200M, 200N of FIG. 37, FIG. 38, FIG. 39 and FIG. 40 are similar to the bio-sensing apparatuses 200F, 200G, 200H, 200I of FIG. 31, FIG. 32, FIG. 33 and FIG. 34, so that the same or similar devices are denoted by the same or similar referential numbers. A difference between the bio-sensing apparatuses 200K, 200L, 200M, 200N and the bio-sensing apparatuses 200F, 200G, 200H, 200I is that the bio-sensing apparatuses 200K, 200L, 200M, 200N are respectively added with a light absorbing layer 292 covering the sidewall 219 compared to the bio-sensing apparatuses 200F, 200G, 200H, 200I.

Figure 41:
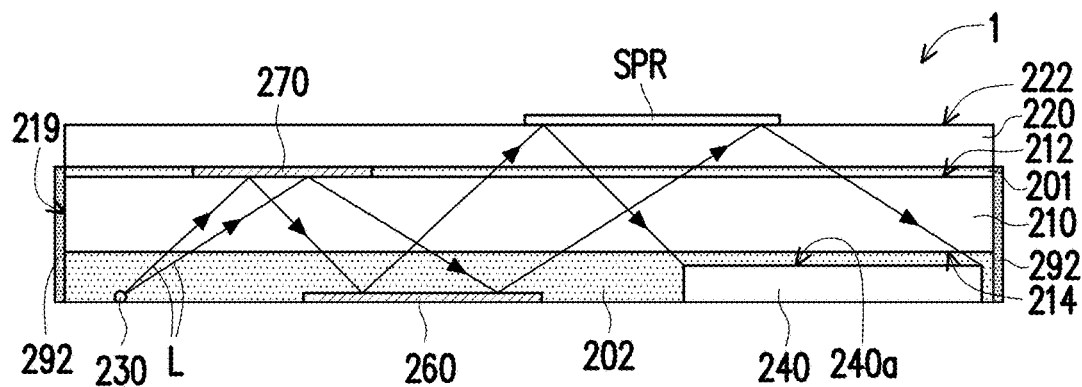
FIG. 41 is a cross-sectional view of a bio-sensing apparatus according to an exemplary embodiment of the invention.

FIG. 41 is a cross-sectional view of a bio-sensing apparatus according to an exemplary embodiment of the invention. The bio-sensing apparatus 200O of FIG. 41 is similar to the bio-sensing apparatus 200E of FIG. 30, so that the same or similar devices are denoted by the same or similar referential numbers. A difference between the bio-sensing apparatus 200O and the bio-sensing apparatus 200E is that the bio-sensing apparatus 200O is added with the light absorbing layer 292 compared to the bio-sensing apparatus 200E. The light absorbing layer 292 at least covers the sidewall 219 of the light guide 210. In the embodiment of FIG. 41, the light absorbing layer 292 may selectively cover the sidewall of the first optical adhesive 201 and/or the sidewall of the second optical adhesive 202, though the invention is not limited thereto.

Figure 42:
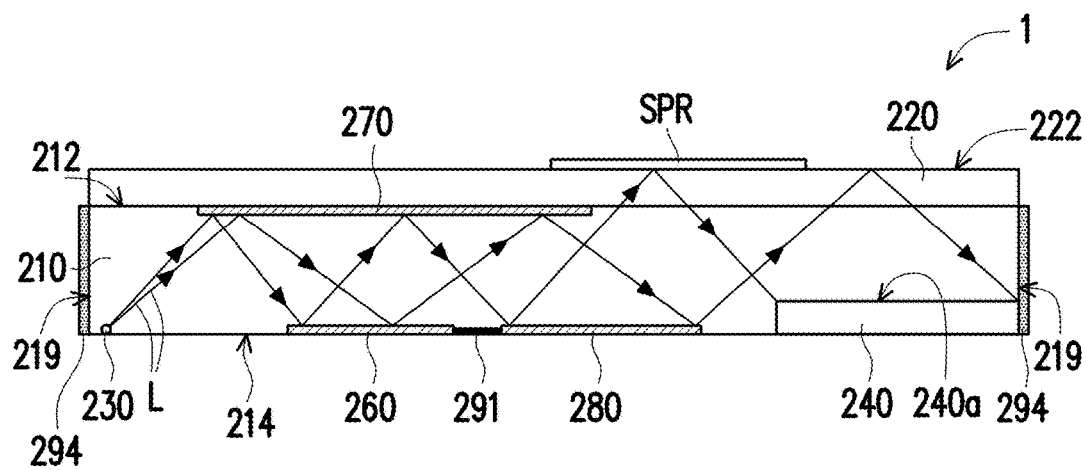
FIG. 42 is a cross-sectional view of a bio-sensing apparatus according to an exemplary embodiment of the invention.

FIG. 42 is a cross-sectional view of a bio-sensing apparatus according to an exemplary embodiment of the invention. Referring to FIG. 42, the bio-sensing apparatus 200 includes a light guide 210. The light guide 210 has a top surface 212 and a bottom surface 214 disposed opposite to each other. The bio-sensing apparatus 200P includes a light-transmitting element 220. The light-transmitting element 220 is disposed on the top surface 212 of the light guide 210. The light-transmitting element 220 has a surface 222 back-facing to the light guide 210.

The bio-sensing apparatus 200P includes a second reflecting device 270 and a first reflecting device 260. The second reflecting device 270 is disposed on the top surface 212 of the light guide 210. The second reflecting device 270 is located between the light-transmitting element 220 and the light guide 210. The first reflecting device 260 is disposed on the bottom surface 214 of the light guide 210. The light guide 210 is located between the second reflecting device 270 and the first reflecting device 260. In the present embodiment, the first reflecting device 260 may be located within an area of the second reflecting device 270, though the invention is not limited thereto. The bio-sensing apparatus 200P includes a light-emitting element 230. The light-emitting element 230 is adapted to emit a light beam L. The light beam L reflected by the second reflecting device 270 and the first reflecting device 260 is transmitted toward the light-transmitting element 220, and is totally reflected by the interface (i.e. the surface 222) between the light-transmitting element 220 and the environment medium 1. The bio-sensing apparatus 200P includes a sensing element 240. The sensing element 240 is disposed on the bottom surface 214 of the light guide 210. The light guide 210 is located between the light-transmitting element 220 and the sensing element 240. The sensing element 240 has a light receiving surface 240a facing to the light guide 210.

It should be noted that the bio-sensing apparatus 200P includes a first light absorbing device 291. The first light absorbing device 291 is disposed on the bottom surface 214 of the light guide 210. The first light absorbing device 291 can absorb the stray light L transmitted to the bottom surface 214, so as to improve the image capturing quality of the bio-sensing apparatus 200P. In the present embodiment, the first light absorbing device 291 may be disposed beside the first reflecting device 260 without overlapping with the first reflecting device 260. Further, the bio-sensing apparatus 200P further includes a third reflecting element 280. The third reflecting element 280 is disposed on the bottom surface 214 of the light guide 210. The first light absorbing device 291 can be located between the first reflecting device 260 and the third reflecting element 280. The light beam L reflected by the second reflecting device 270, the first reflecting device 260 and the third reflecting element 280 is transmitted toward the light-transmitting element 220.

Figure 43:
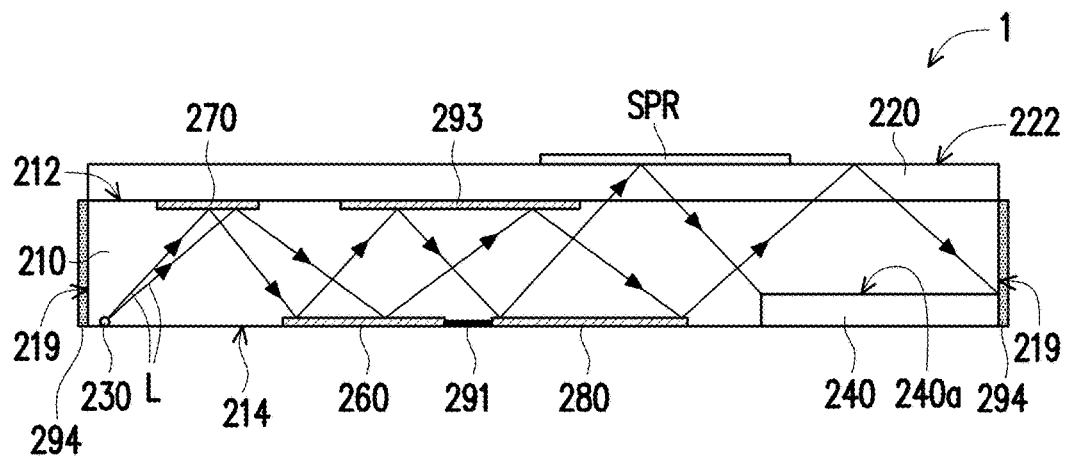
FIG. 43 is a cross-sectional view of a bio-sensing apparatus according to an embodiment of the invention.

FIG. 43 is a cross-sectional view of a bio-sensing apparatus according to an embodiment of the invention. The bio-sensing apparatus 200Q of FIG. 43 is similar to the bio-sensing apparatus 200P of FIG. 42, so that the same or similar devices are denoted by the same or similar referential numbers. A difference between the bio-sensing apparatus 200Q and the bio-sensing apparatus 200P is that the bio-sensing apparatus 200Q further includes a fourth reflecting device 293. The fourth reflecting device 293 is disposed on the top surface 212 of the light guide 210 and is separated from the second reflecting device 270. The light beam L reflected by the second reflecting device 270, the first reflecting device 260, the third reflecting element 280 and the fourth reflecting device 293 is transmitted toward the light-transmitting element 220. In the present embodiment, the light beam L can be sequentially reflected by the second reflecting device 270, the first reflecting device 260, the fourth reflecting device 293 and the third reflecting element 280, and is transmitted toward the light-transmitting element 220.

Figure 44:
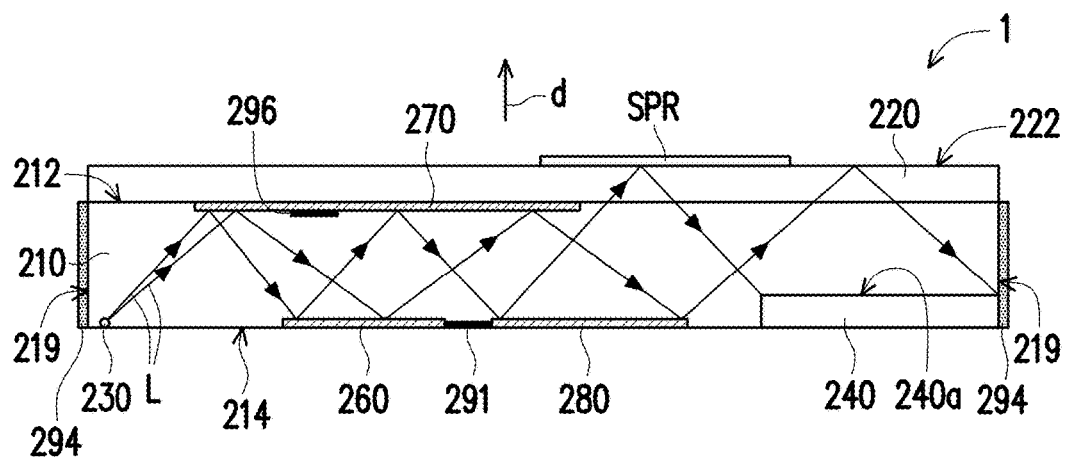
FIG. 44 is a cross-sectional view of a bio-sensing apparatus according to an exemplary embodiment of the invention.

FIG. 44 is a cross-sectional view of a bio-sensing apparatus according to an exemplary embodiment of the invention. The bio-sensing apparatus 200R of FIG. 44 is similar to the bio-sensing apparatus 200P of FIG. 42, so that the same or similar devices are denoted by the same or similar referential numbers. A difference between the bio-sensing apparatus 200R and the bio-sensing apparatus 200P is that the bio-sensing apparatus 200R further includes a second light absorbing device 296. The second light absorbing device 296 is disposed on the top surface 212 of the light guide 210. The second light absorbing device 296 may absorb the stray light L transmitted to the top surface 212, so as to improve the image capturing quality of the bio-sensing apparatus 200R. In the present embodiment, the second light absorbing device 296 can be selectively disposed on the second reflecting element 270 and located between the second reflecting device 270 and the bottom surface 214 of the light guide 210. The first light absorbing device 291 and the second light absorbing device 296 can be staggered, and are not overlapped along a direction d perpendicular to the surface 222.

Figure 45:
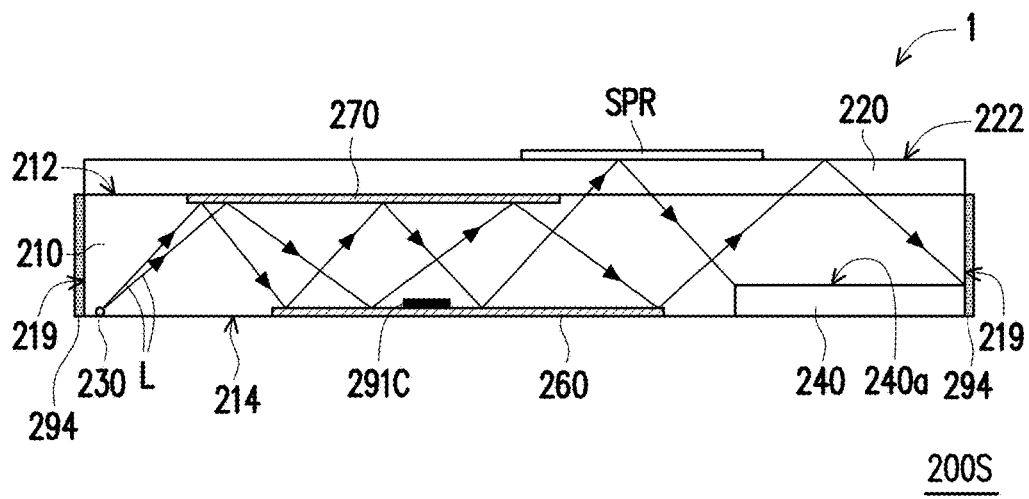
FIG. 45 is a cross-sectional view of a bio-sensing apparatus according to an exemplary embodiment of the invention.

FIG. 45 is a cross-sectional view of a bio-sensing apparatus according to an exemplary embodiment of the invention. The bio-sensing apparatus 200S of FIG. 45 is similar to the bio-sensing apparatus 200P of FIG. 42, so that the same or similar devices are denoted by the same or similar referential numbers. A difference between the bio-sensing apparatus 200S and the bio-sensing apparatus 200P is that the first light absorbing device 291C of the bio-sensing apparatus 200P is disposed on the first reflecting device 260 and is located between the top surface 212 of the light guide 210 and the first reflecting device 260.

Figure 46:
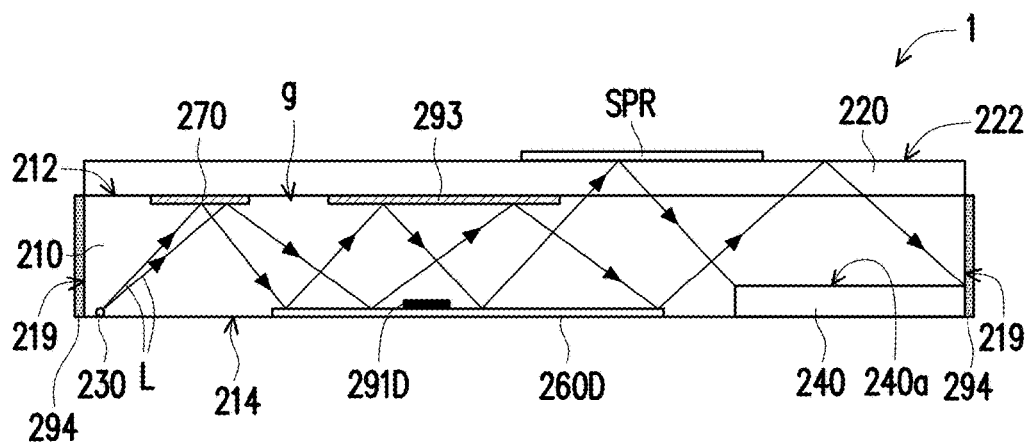
FIG. 46 is a cross-sectional view of a bio-sensing apparatus according to an exemplary embodiment of the invention.

FIG. 46 is a cross-sectional view of a bio-sensing apparatus according to an exemplary embodiment of the invention. The bio-sensing apparatus 200T of FIG. 46 is similar to the bio-sensing apparatus 200Q of FIG. 43, so that the same or similar devices are denoted by the same or similar referential numbers. A difference between the bio-sensing apparatus 200T and the bio-sensing apparatus 200Q is that the bio-sensing apparatus 200T does not include the third reflecting element 280 of the bio-sensing apparatus 200Q, the first reflecting device 260D of the bio-sensing apparatus 200T at least extends from a position right below a gap g between the second reflecting device 270 and the fourth reflecting device 293 to a position right below a tail end of the fourth reflecting device 293, and the first light absorbing device 291D may be disposed on the first reflecting device 260D and is located between the bottom surface 214 of the light guide 210 and the first reflecting device 260D.

It should be noted that in another variation of FIG. 42 to FIG. 46, the light guides 210 have the top surface 212 and the bottom surface 214 opposite to each other and the sidewall 219 connected between the top surface 212 and the bottom surface 214, and the sidewall 219 can also be covered with a light absorbing layer 294. Moreover, the light guide 210 of any of FIG. 30 to FIG. 37 can be a transparent plate or an optical adhesive filled in a location of the light guide 210 (a multi-layer light guide medium shown in FIG. 30 can be used) in the space occupied by the light guide 210, which is not limited by the invention.

Referring to FIG. 22, FIG. 24, FIG. 25, FIG. 27, FIG. 28, FIG. 30, FIG. 31, FIG. 32, FIG. 33, FIG. 34, FIG. 35, FIG. 37, FIG. 38, FIG. 39, FIG. 40, FIG. 41, FIG. 42, FIG. 43, FIG. 44, FIG. 45 and FIG. 46, the bio-sensing apparatuses 200, 200A-200T respectively include surface plasma resonance layers SPR. Functions of the surface plasma resonance layers SPR of the bio-sensing apparatuses 200, 200A-200T and a function of the surface plasma resonance layer SPR of the above bio-sensing apparatus 100 are the same, and which will not be repeated here.

Figure 47:
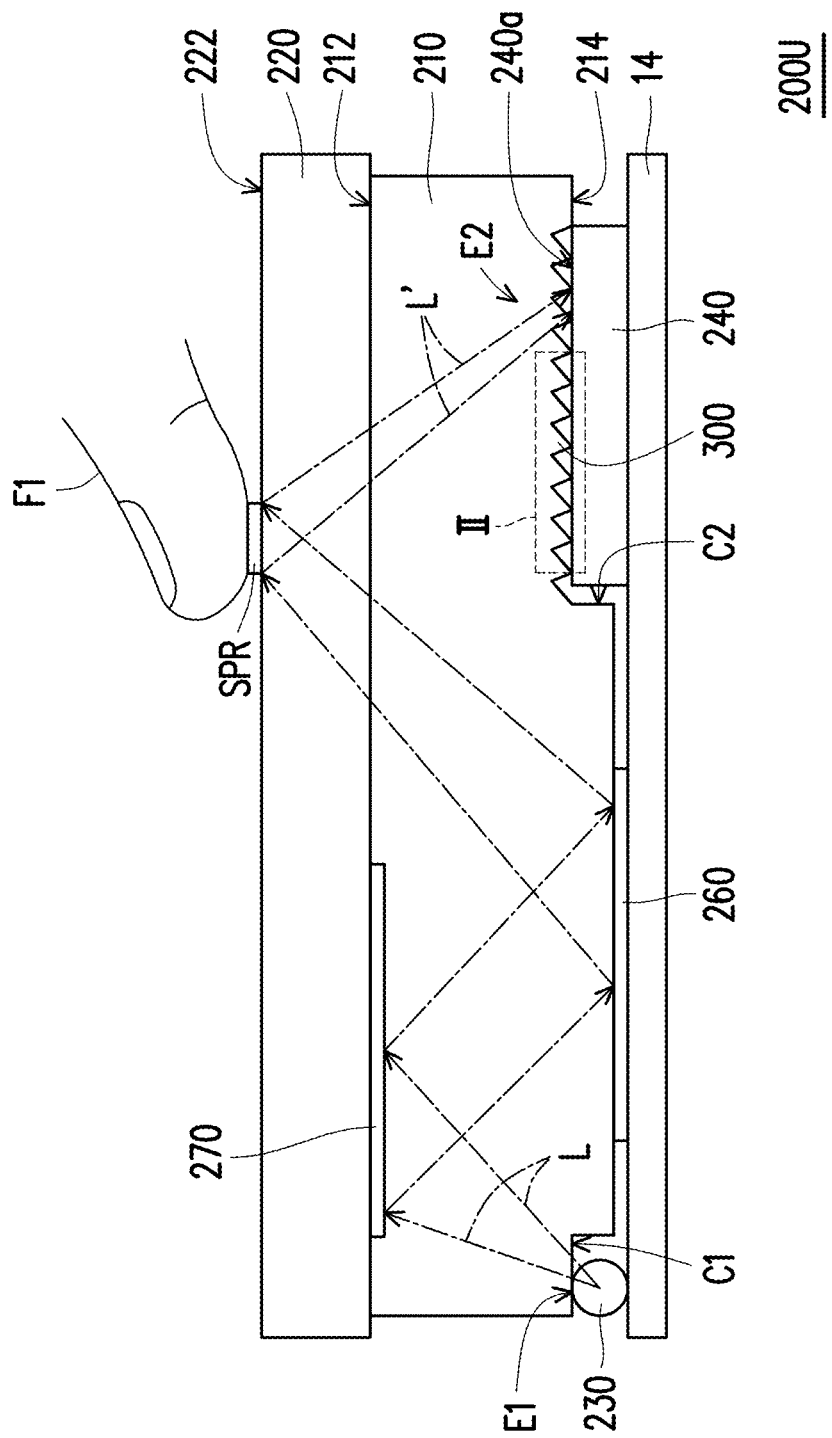
FIG. 47 shows a cross-sectional view of one embodiment of the image capture apparatus of the present disclosure.
Figure 48:
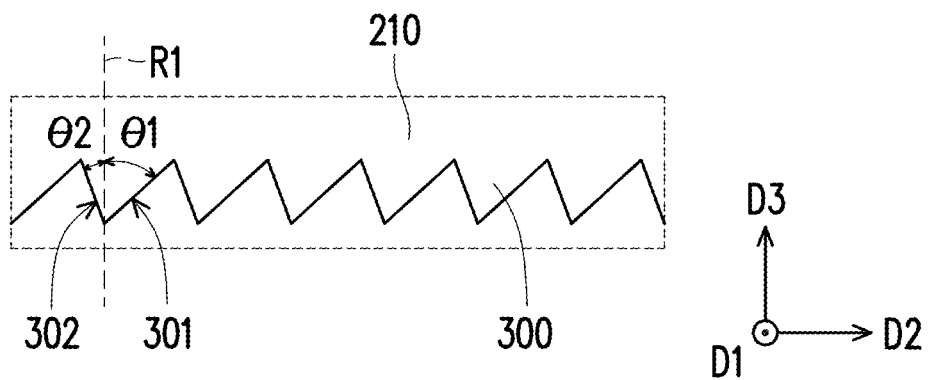
FIG. 48 is a partial enlarged view depicting area II of FIG. 47 of one embodiment of a plurality of enhanced transmission microstructures of the present disclosure.

Please refer to FIG. 47 and FIG. 48. FIG. 47 shows a cross-sectional view of one embodiment of the image capture apparatus of the present disclosure, and FIG. 48 is a partial enlarged view depicting area II of FIG. 47 of one embodiment of a plurality of enhanced transmission microstructures of the present disclosure. An exemplary embodiment of the present disclosure provides a bio-sensing apparatus 200U. The bio-sensing apparatus 200U is used in an environmental medium. In an embodiment, the above-mentioned environmental medium can be gas, water, or other kinds of environmental mediums. The bio-sensing apparatus 200U can used to capture an image of an object F1 for identification, the above-mentioned object F1 can be a user's finger, palm, wrist or eyeball, and the image captured by the bio-sensing apparatus 200U is, for example, a fingerprint, a palm print, a vein, a pupil, or an iris image. However, the present disclosure is not limited thereto.

As shown in FIG. 47, the bio-sensing apparatus 200U according to an exemplary embodiment of the present disclosure includes a substrate 14, a light-emitting element 230, a light guide 210, a light transmitting element 220, and a sensing element 240. The light guide 210 is used to transmit the light beam. The light guide 210 of the exemplary embodiment has a top surface 212 and a bottom surface 214 opposite to the top surface 212. The light guide 210 has a light incident portion E1 and a light emitting portion E2 which are located on the bottom surface 214. The light beam L enters the light guide 210 from the light incident portion E1, passes through the light guide 210, and is totally reflected at least one time to form a signal light beam L', then the light beam L leaves the light guide 210 through the light emitting portion E2 of the light guide 210. In this exemplary embodiment, a plurality of enhanced transmission microstructures 300 are disposed on the light emitting portion E2 of the light guide 210.

It should be noted that when the signal light beam L' enters the environmental medium (such as air or air bubbles) by the light guide 210, in order to prevent the angle of the light beam projecting to the light emitting portion E2 from being greater than the total reflection critical angle of the light guide 210 to cause that the signal light beam L' supposed to be emitted by the light emitting portion E2 will be totally reflected again, the light-emitting portion E2 is disposed with a plurality of enhanced transmission microstructures 300 to break the total reflection of the signal light beam L'.

Specifically, each enhanced transmission microstructure 300 has a light receiving area 301 and a back area 302. In an embodiment, the light receiving area 301 enables an incident angle of the signal light beam L' to be less than the total reflection critical angle of the light guide 210, and the back area 302 enables an incident angle of the signal light beam L' to be greater than the total reflection critical angle. In another exemplary embodiment, the back area 302 is substantially parallel to the main projection direction of the signal light beam L', so that the signal light beam L' is less likely to be projected on the back area 302. In addition, the light receiving area 301 is substantially vertical to the main projection direction of the light beam L, and the light receiving area 301 is greater than back area 302, such that most of the signal light beam L' project to the light receiving area 301 and the signal light beam L' projecting to the light receiving area 301 would not to be totally reflected easily.

Please refer to FIG. 47 and FIG. 48. It should be noted that although a small amount of stray lights may be projected to the back area 302, the stray light will be totally reflected, and it will not emit out from the light emitting portion E2 and interfere with the signal of the sensing element 240 to cause ghosting. In addition, after the signal light beam L' passing through the light receiving area 301, a portion of the light beam will be transmitted through the light receiving surface 240a of the sensing element 240 and the back area 302, then the light beam will be refracted to be another light beam with a greater angle, and the light beam will be totally reflected on an outer surface 110 of the light transmitting element 220. Therefore, the angle of the totally reflected light beam is greater than the original one, resulting in that the light beam travels away from the original path and will not enter the light receiving surface 240a of the sensing element 240 again, so as to avoid the signal overlapping.

Referring to FIG. 48, in this embodiment, the enhanced transmission microstructures 300 are connected with each other, and the cross-sectional shape of each enhanced transmission microstructure 300 may be mountain-shaped, wave-shaped or zigzag-shaped. In the embodiment of FIG. 48, the cross-sectional shape of each enhanced transmission microstructure 300 is zigzag-shaped. In addition, both the light receiving area 301 and the back area 302 of the embodiment are inclined planes.

Figure 49:
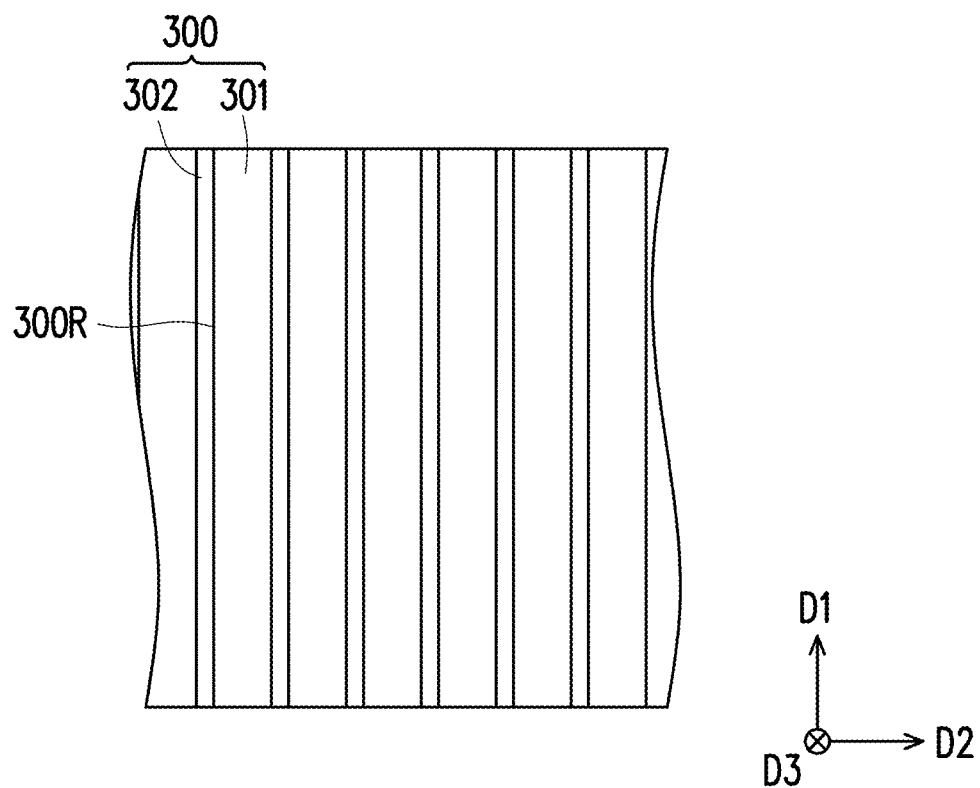
FIG. 49 shows a partial bottom view of the light guide element according to an embodiment of the present disclosure.

Please refer to FIG. 48 and FIG. 49 together. FIG. 49 shows a partial bottom view of the light guide element according to an embodiment of the present disclosure. Furthermore, in this embodiment, each enhanced transmission microstructure 300 is an asymmetric column, and the asymmetric column extends in the first direction D1 and is arranged along the second direction D2.

Each asymmetric column has a ridgeline 300R, that is, a borderline between the light receiving area 301 and the back area 302. In the present embodiment, a vertical reference plane P1 passing through the ridgeline 300R is defined. As shown in FIG. 48, the vertical reference plane P1 is parallel to the third direction D3, which is also parallel to the thickness direction of the light guide 210. The light receiving area 301 and the back area 302 are respectively located at two opposite sides of the vertical reference plane P1. The light receiving area 301 and the vertical reference plane P1 form a first angle $\theta 1$, and the back area 302 and the vertical reference plane P1 form a second angle $\theta 2$. In this embodiment, the first angle $\theta 1$ is greater than the second angle $\theta 2$ to ensure that most of the light beam can be projected to the light receiving area 301 and it will no longer be totally reflected.

Additionally, in this embodiment, with regard to the two adjacent enhanced transmission microstructures 300, the edge of the light receiving area 301 of one enhanced transmission microstructure 300 may overlap the edge of the back area 302 of another enhanced transmission microstructure 300. That is to say, the two adjacent enhanced transmission microstructures 300 do not form a connection area to be connected, which further reduces the probability of total reflection of the light beams. However, in other embodiments, as long as the inclination angle of the connection area with respect to the vertical reference plane P1 can avoid the total reflection of the light beam or does not affect the path of the light beam, the connection area may be disposed between every two adjacent enhanced transmission microstructures 300.

In addition, the shape of the enhanced transmission microstructure 300 according to the embodiment of the present disclosure is not limited to an asymmetric column, and the light receiving area 301 and the back area 302 may also be a curved surface. For example, the curved surface can be a concave surface or a convex surface. Please refer to FIG. 4, which illustrates a partial bottom view of the light guide element according to another exemplary embodiment of the present disclosure. In this embodiment, multiple enhanced transmission microstructures 300 are arranged in an array, and each enhanced transmission microstructure 300 is an eccentric micro-lens.

Figure 50:
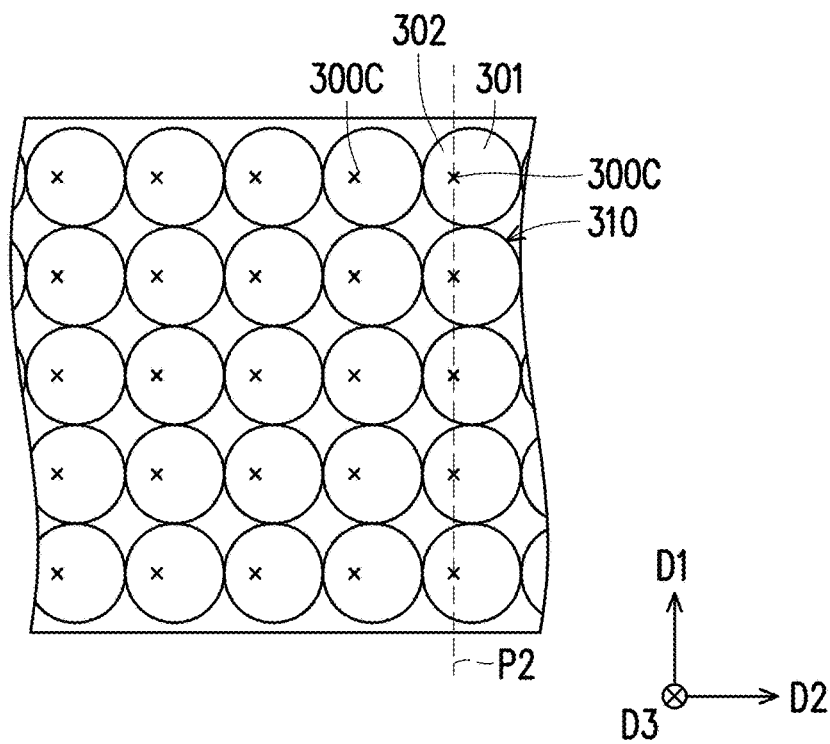
FIG. 50 shows a partial bottom view of the light guide element according to an embodiment of the present disclosure.

As shown in FIG. 50, the bottom cross-sectional shape of each enhanced transmission microstructure 300 is circular; however, in terms of the bottom perspective, the vertex 300C of the enhanced transmission microstructure 300 is offset with respect to the center of the bottom cross-sectional shape (circle). That is, the vertex 300C of the enhanced transmission microstructure 300 is not aligned with the center of the bottom cross-sectional shape (circle). In this embodiment, the edge of one enhanced transmission microstructure 300 is connected to the edge of another enhanced transmission microstructure 300.

Furthermore, in the embodiment, a line P2 is defined by the vertexes 300C of all enhanced transmission microstructures 300 arranged along the first direction D1 in the same row, and the line P2 can differentiate the surface area of each enhanced transmission microstructure 300 into a light receiving area 301 and a back area 102. Specifically, the light receiving area 301 is located at the right side surface area of the line P2, and the back area 302 is located at the left side surface area of the line P2. As shown in FIG. 50, the light receiving area 301 is greater than the back area 302.

Figure 51:
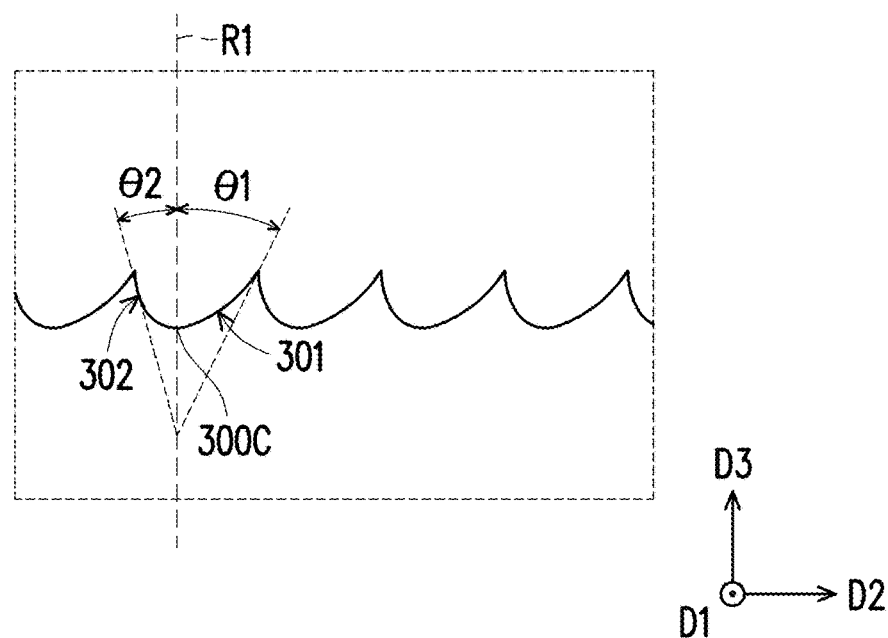
FIG. 51 is a cross-sectional view of the light guide element according to an embodiment of the present disclosure.

Please refer to FIG. 51, which shows a partial cross-sectional view of the light guide element according to yet another embodiment of the present disclosure. Specifically, FIG. 51 is a cross-sectional view depicting the plurality of enhanced transmission microstructures 300 in the second direction D2 as shown in FIG. 50. In this embodiment, the cross-sectional shape of the enhanced transmission microstructure 300 is substantially wavy or mountain-shaped. That is to say, both the light receiving area 301 and the back area 302 are curved surfaces.

In addition, any tangent plane to the light receiving area 301 at any point and a vertical reference plane P1 passing through the vertex 300C form a first angle $\theta 1$, any tangent plane to the back area 302 at any point and the vertical reference plane P1 passing through the vertex 300C form a second angle, and the first angle $\theta 1$ is greater than the second angle $\theta 2$. Accordingly, when the light beam is projected to the light receiving area 301, the incidence angle of the light beam is less than the total reflection critical angle of the light guide 210 that can be ensured, so as to prevent the light beam from being totally reflected.

In other embodiments, the enhanced transmission microstructure 300 can be other eccentric cones, such as an eccentric polygonal cone (the bottom cross-sectional shapes of the enhanced transmission microstructures 300 are triangular), a quadrangular cone or other polygonal cones. The embodiment of the present disclosure does not limit the shape of the enhanced transmission microstructure 300, as long as the probability of the total reflection of the light beam can be reduced (or the probability of the light beam penetrating the light emitting portion E2 can be increased).

Please further refer to FIG. 47. The bio-sensing apparatus 200U in this embodiment further includes a light transmitting element 220. The light transmitting element 220 is disposed on the top surface 212 of the light guide 210 and has an surface 222 which is in contact with the environmental medium and faces away from the light guide 210. If the bio-sensing apparatus 200 is used in an optical fingerprint recognition system for capturing fingerprints and/or veins, the surface 222 of the light transmitting element 220 can be touched or pressed by a finger for detection and recognition.

The bio-sensing apparatus 200U further includes a substrate 14 located at a second side of the light guide 210, a light-emitting element 230, and an sensing element 240; in which, the light-emitting element 230 and the sensing element 240 are both disposed on the substrate 14. The substrate 14 can be a circuit board on which wiring has been already configured in advance. In addition, the material of the substrate 14 is a light absorbing material.

The sensing element 240 is disposed on the substrate 14 corresponding to the plurality of enhanced transmission microstructures 300 of the light guide 210 to capture the image of the object F1. In other words, the light guide 210 is located between the sensing element 240 and the light transmitting element 220.

The sensing element 240 has a light receiving surface 240a for receiving the light beam L emitted by the light emitting portion E2 of the light guide 210. In other words, the light beam is projected to the light receiving surface 240a of the sensing element 240 after passing through the plurality of enhanced transmission microstructures 300.

The light-emitting element 230 is disposed on the substrate 14 and close to the light incident portion E1 of the light guide 210, and the light-emitting element 230 is used to emitting a light beam L transmitted in the light guide 210. In this embodiment, the light-emitting element 230 is disposed outside the light guide 210, and the light beam L generated by the light-emitting element 230 is projected to the light incident portion E1 of the light guide 210.

Further, the bottom surface 214 of the light guide 210 has a first recessed portion C1 for accommodating the light-emitting element 230 and a second recessed portion C2 for accommodating the sensing element 240. The light incident portion E1 of the light guide 210 is located at the first recessed portion C1 and the light emitting portion E2 of the light guide 210 is located at the second recessed portion C2.

As shown in FIG. 47, when the light-emitting element 230, the light guide 210, and the sensing element 240 are all disposed on the substrate 14, the light-emitting element 230 can be fitted and fixed in the first recessed portion C1, and the sensing element 240 can be fitted and be fixed in the second recessed portion C2. In addition, in a feasible embodiment, the plurality of enhanced transmission microstructures 300 are located at the bottom of the second recessed portion C2. In this way, the overall volume of the bio-sensing apparatus 200 can be shortened. However, in some embodiments, the first recessed portion C1 and the second recessed portion C2 can be omitted. In other embodiments, the light-emitting element 230 may be embedded in the light guide 210. Specifically, after the light-emitting element 230 is disposed on the substrate 14, the light guide 210 is formed by steps of potting and curing, such that the light-emitting element 230 is embedded in the light guide 210. Consequently, the light beam L generated by the light-emitting element 230 can be directly transmitted through the light guide 210 without relying on any other medium.

In addition, the light-emitting element 230 in this embodiment of the present disclosure is disposed on the bottom surface 214 of the light guide 210. In other embodiments, the light-emitting element 230 can be disposed on the top surface 212 of the light guide 210.

In addition, the bio-sensing apparatus 200 according to the embodiment of the present disclosure further includes a second reflective element 270 and a first reflective element 260. The second reflective element 270 and the first reflective element 260 are respectively disposed on the top surface 212 and the bottom surface 214 of the light guide 210. Specifically, the second reflective element 270 is located between the light transmitting element 220 and the light guide 210, and the first reflective element 260 is located between the substrate 14 and the light guide 210. In an embodiment, the second reflective element 270 and the first reflective element 260 can be reflective sheets or reflective films formed on the surface of the light guide 210 or may be formed by gratings, but the present disclosure is not limited thereto.

In addition, in this embodiment, the second reflective element 270 and the first reflective element 260 may be staggered with respect to each other and at least partially overlap in the thickness direction of the light guide 210 to guide the light beam L to the light transmitting element 220. In other embodiments, the second reflective element 270 and the first reflective element 260 may be completely staggered without overlapping. Therefore, the present disclosure does not limit the relative positions of the second reflective element 270 and the first reflective element 260 or the reflection of the light beam L, as long as the light beam L can be guided to the light transmitting element 220.

For example, in other exemplary embodiments, light beam L can undergo a total reflection in the light guide 210 and the environmental medium by designing the traveling path of light beam L. In this case, the first reflective element 260 may be omitted. In general, the light beam L generated by the light-emitting element 230 enters the light guide 210 through the light incident portion E1, is sequentially reflected by the second reflective element 270 and the first reflective element 260 to be transmitted in the light transmitting element 220 of the light guide 210, and then causes total reflection at the interface of the light transmitting element 220 and the environmental medium, which is the surface 222 of the light transmitting element 220.

When the object F1 (e.g. a finger) contacts the surface 222 of the light transmitting element 220, the ridges of the finger contact the surface 222, such that a portion of the light beam L cannot be totally reflected, and the sensing element 240 obtains the dark lines corresponding to the ridges of the finger. On the other hand, the valleys of the finger do not touch the surface 222 of the light transmitting element 220, and the other portion of the light beam L can still be totally reflected to form a signal light beam L'. The signal light beam L' is projected toward the light emitting portion E2 of the light guide 210 and directed to the light receiving surface 240a of the sensing element 240 by the plurality of enhanced transmission microstructures 300 of the light guide 210. Subsequently, the light beam L' received by the sensing element 240 is performed an image process by an image processing component to obtain the fingerprint image of the object F1.

This is to say, in the embodiment of the present disclosure, the enhanced transmission microstructures 300 disposed on the light emitting portion E2 of the light guide 210, can be applied to prevent the signal light beam L' from being totally reflected again before entering the sensing element 240, so as to reduce the image resolution of the bio-sensing apparatus 200U.

Figure 52:
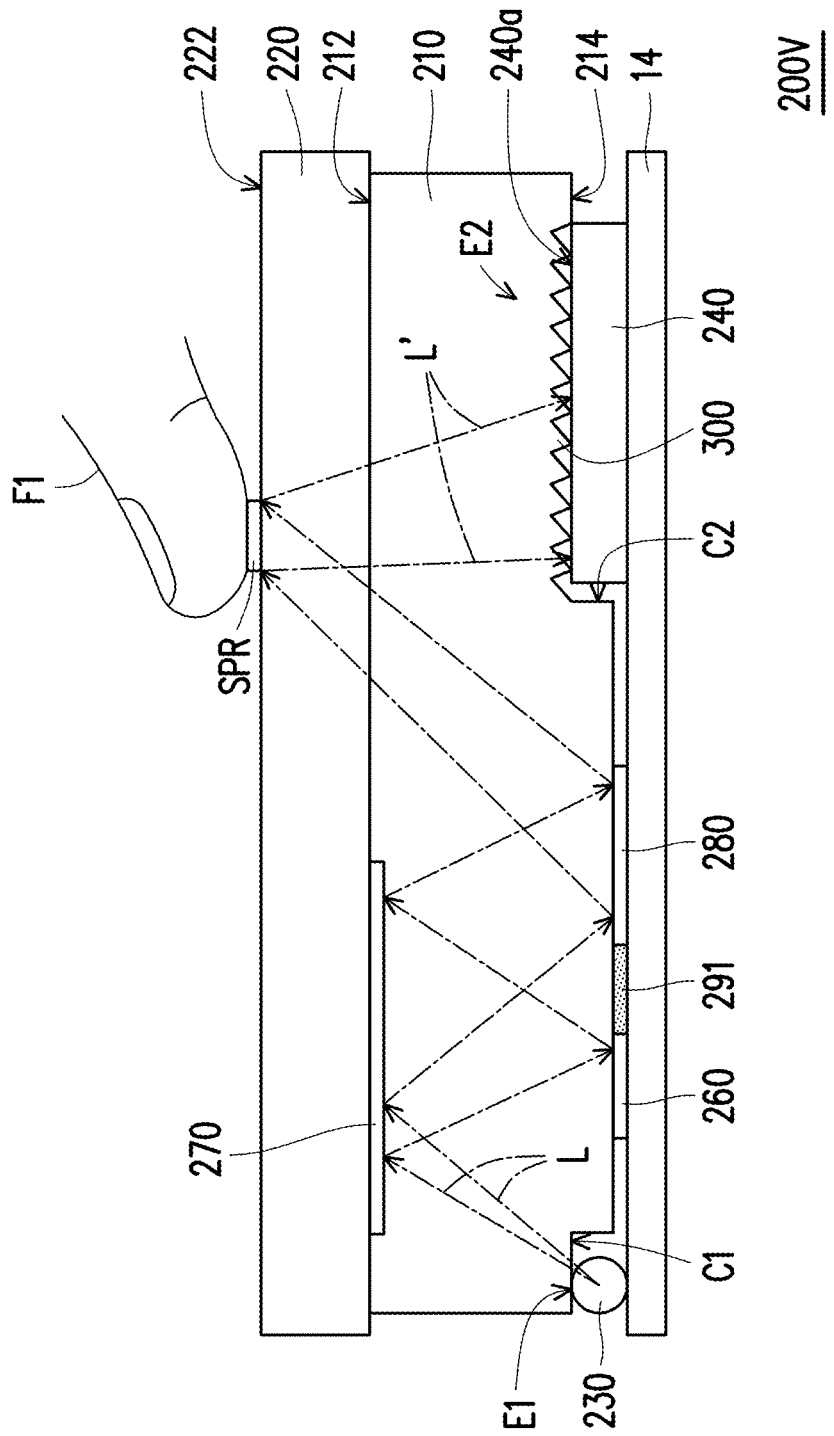
FIG. 52 is a schematic cross-sectional view of a bio-sensing apparatus according to an embodiment of the present disclosure.

Please refer to FIG. 52. FIG. 52 is a schematic cross-sectional view of a bio-sensing apparatus according to an embodiment of the present disclosure. The bio-sensing apparatus 200V of FIG. 52 is the same as the bio-sensing apparatus 200U of FIG. 47 or is denoted with the same component symbols corresponding to FIG. 47, and thus unnecessary details are not repeated. In the embodiment of FIG. 52, the bio-sensing apparatus 200V further includes a third reflective element 280 located on the bottom surface 214 of the light guide 210. That is to say, the first reflective element 260 and the third reflective element 280 are located on the same surface of the light guide 210, but are mutually separated to be arranged. In this embodiment, the light beam L is reflected by the second reflective element 270, the first reflective element 260 and the third reflective element 280 to be transmitted in the light guide 210 and projected to the light transmitting element 220.

In an embodiment, the second reflective element 270 and the first reflective element 260 are completely overlapped in the thickness direction of the light guide 210, and the second reflective element 270 and the third reflective element 280 only partially overlap in the thickness direction of the light guide 210.

Moreover, the bio-sensing apparatus 200V in this embodiment further includes a light absorbing element 291 disposed between the first reflective element 260 and the third reflective element 280. In the present embodiment, the light absorbing element 291 and the second reflective element 270 overlap in the thickness direction of the light guide 210. Further, the vertical projection of the second reflective element 270 may at least partially overlap the light absorbing element 291.

In other exemplary embodiments, the light absorbing element 291 may be disposed on other areas of the light guide 210, that is, the area where the second reflective element 270, the first reflective element 260, and the third reflective element 280 are not disposed. For example, the bio-sensing apparatus 200V further includes a plurality of light absorbing assemblies 18 disposed on two opposite sidewalls of the light guide 210, and the aforementioned sidewall surface refers to the surface connected between the top surface 212 and the bottom surface 214 of the light guide 210. The light absorbing element 291 can be an opaque and not reflective masking layer, for example, an ink layer, an adhesive layer, or a masking sheet, but the foregoing embodiments are not intended to limit the present disclosure.

The light absorbing element 291 can absorb and reduce the stray light which does not follow the predetermined light path, so that the sensing element 240 can be prevented from receiving stray light other than the signal light beam L'. In addition, the light absorbing element 291 can be configured to increase the image capturing area and make the signal light beam L' transmit to the sensing element 240 uniformly, further improving imaging quality.

Figure 53:
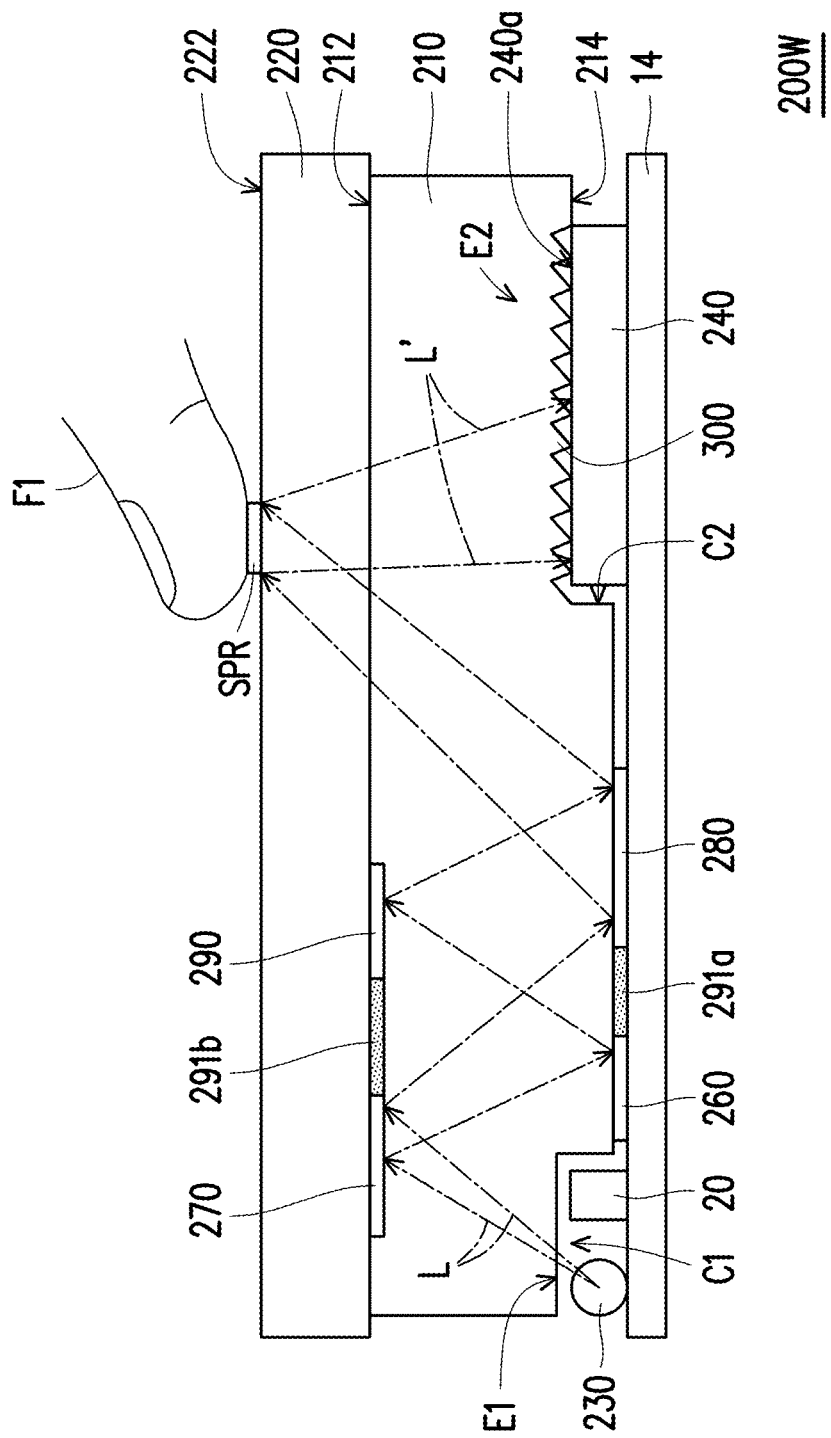
FIG. 53 is a schematic sectional view of a bio-sensing apparatus according to an embodiment of the invention.

Please refer to FIG. 53, which is a cross-sectional view depicting a bio-sensing apparatus according to another exemplary embodiment of the present disclosure. The bio-sensing apparatus 200W of FIG. 53 is the same as the bio-sensing apparatus 200V of FIG. 52 or is denoted with the same component symbols corresponding to FIG. 52, and thus unnecessary details are not repeated. In the embodiment of FIG. 53, the bio-sensing apparatus 200W further includes a fourth reflective element 290 located on the top surface 212 of the light guide 210. That is, the second reflective element 270 and the fourth reflective element 290 are located on an identical surface of the light guide 210, but are mutually separated to be arranged. In this embodiment, the light beam L is sequentially reflected by the second reflective element 270, the first reflective element 260, the fourth reflective element 290 and the third reflective element 280 to be transmitted in the light guide 210 and projected to the light transmitting element 220.

In an embodiment, the second reflective element 270 and the first reflective element 260 at least partially overlap in the thickness direction of the light guide 210, and the fourth reflective element 290 and the third reflective element 280 also partially overlap in the thickness direction of the light guide 210. However, the second reflective element 270 and the third reflective element 280 do not overlap in the thickness direction of the light guide 210.

Moreover, in addition to the light absorbing element 291a disposed between the first reflective element 260 and the third reflective element 280, the bio-sensing apparatus 200 further includes a light absorbing element 291b disposed between the second reflective element 270 and the third reflective element 280. In the present embodiment, the two light absorbing assemblies (18a and 18b) and the second reflective element 270 at least partially overlap in the thickness direction of the light guide 210.

Similar to the embodiment of FIG. 52, the two light absorbing assemblies 291a, 291b can absorb and reduce stray light which does not follow the predetermined light path, thereby preventing the sensing element 240 from receiving stray light other than the signal light beam L'. In addition, the light absorbing element 291 can be configured to increase the image capturing area and make the signal light beam L' transmit to the sensing element 240 more uniformly, thereby improving imaging quality.

Moreover, in this embodiment, the bio-sensing apparatus 200W further includes a block 20 disposed in the first recessed portion C1. The block 20 is disposed between the light-emitting element 230 and the sensing element 240 to prevent the light beam L from being directly received by the sensing element 240. Additionally, the block 20 can limit the divergence angle of the light beam L generated by the light-emitting element 230, so that the light beam L can be controlled to enter the light guide 210 with a predetermined incident angle more accurately. In this way, the light path of the light beam L can be further controlled precisely, and most of the light beams L can be projected toward the object F1, so as to improve the imaging quality of the sensing element 240.

Figure 54:
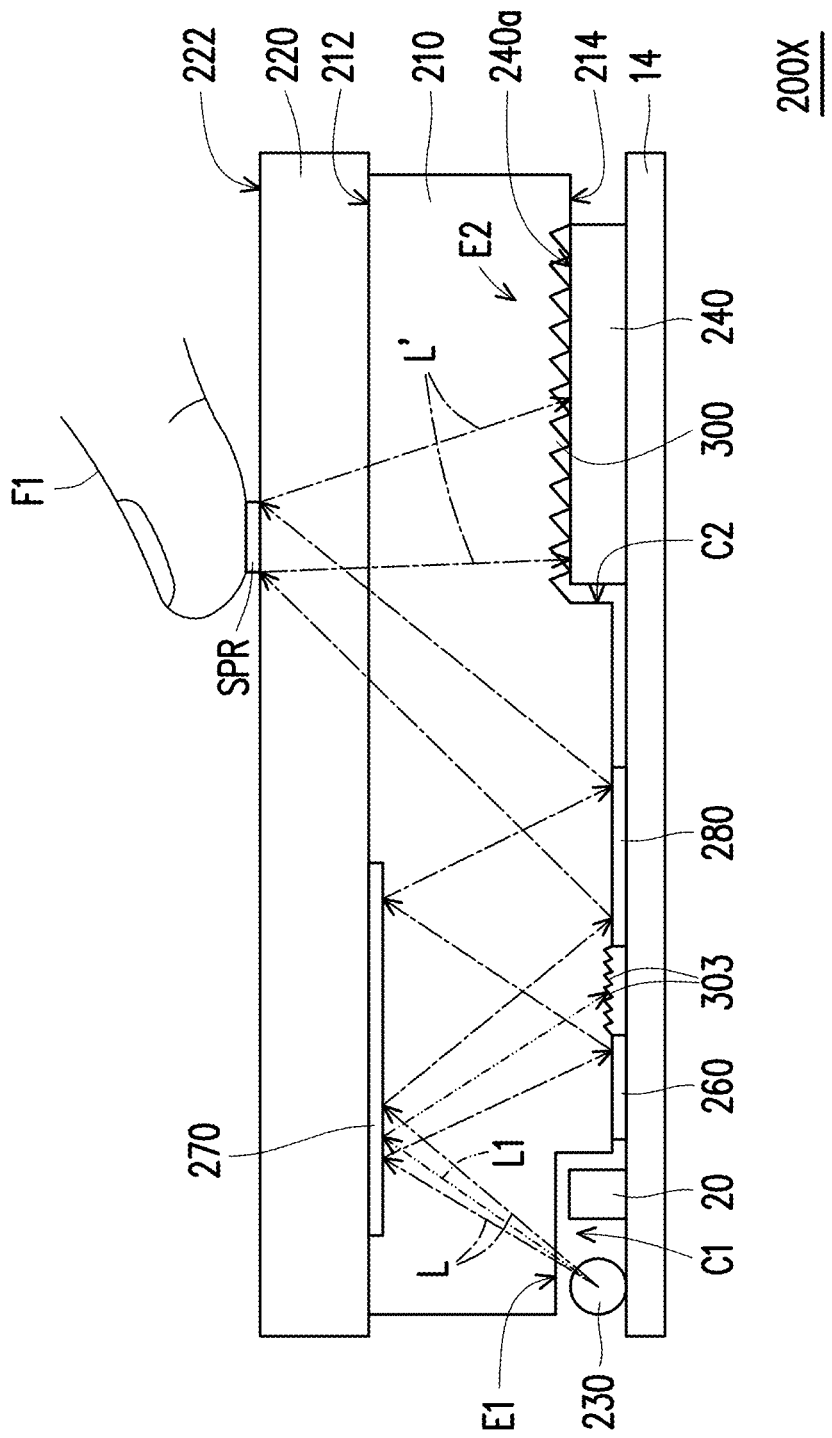
FIG. 54 is a schematic sectional view of a bio-sensing apparatus according to an embodiment of the invention.

Please refer to FIG. 54, which is a schematic cross-sectional view of a bio-sensing apparatus according to an embodiment of the present disclosure. The bio-sensing apparatus 200X of FIG. 54 is the same as the bio-sensing apparatus 200V of FIG. 52 or is denoted with the same component symbols corresponding to FIG. 52, and thus necessary details are not repeated.

In the embodiment of FIG. 54, the light guide 210 includes a plurality of optical microstructures 303 disposed between the first reflective element 260 and the third reflective element 280. In the present embodiment, the distributed location of the plurality of optical microstructures 303 and the second reflective element 270 at least partially overlap in the thickness direction of the light guide 210. Further, the vertical projection of the second reflective element 270 can at least partially overlap the distributed location of the plurality of optical microstructures 303.

The shape of each optical microstructure 303 can be the same as that of the enhanced transmission microstructure 300 described above. For example, the cross-sectional shape of the optical microstructure 303 may also be zigzag-shaped, wavy-shaped or mountain-shaped, but the present disclosure is not limited thereto.

The plurality of optical microstructures 303 may project a portion of the light beam reflected by the second reflective element 270 to pass through the plurality of optical microstructures 303 and then to emit out from the light guide 210. Further, the stray light L1 which does not follow a predetermined path can be emitted out from the light guide 210 through the optical microstructures 303 and absorbed by the substrate 14, so as to prevent the sensing element 240 from receiving Astigmatism L1 other than the signal light beam L'. In addition, the configuration of the optical microstructures 303 can increase the imaging area and make the signal light beam L' transmit to the sensing element 240 more uniformly, which is beneficial for improving the imaging quality.

In addition, like the embodiment of FIG. 53, the bio-sensing apparatus 200X in the embodiment of FIG. 54 further includes a block 20 disposed in the first recessed portion C1. The block 20 is applied to prevent the light beam L from directly projecting to the sensing element 240, and can limit the divergence angle of the light beam L generated by the light-emitting element 230, so that the light beam L can be controlled to enter the light guide 210 with a predetermined incident angle more accurately.

Figure 55:
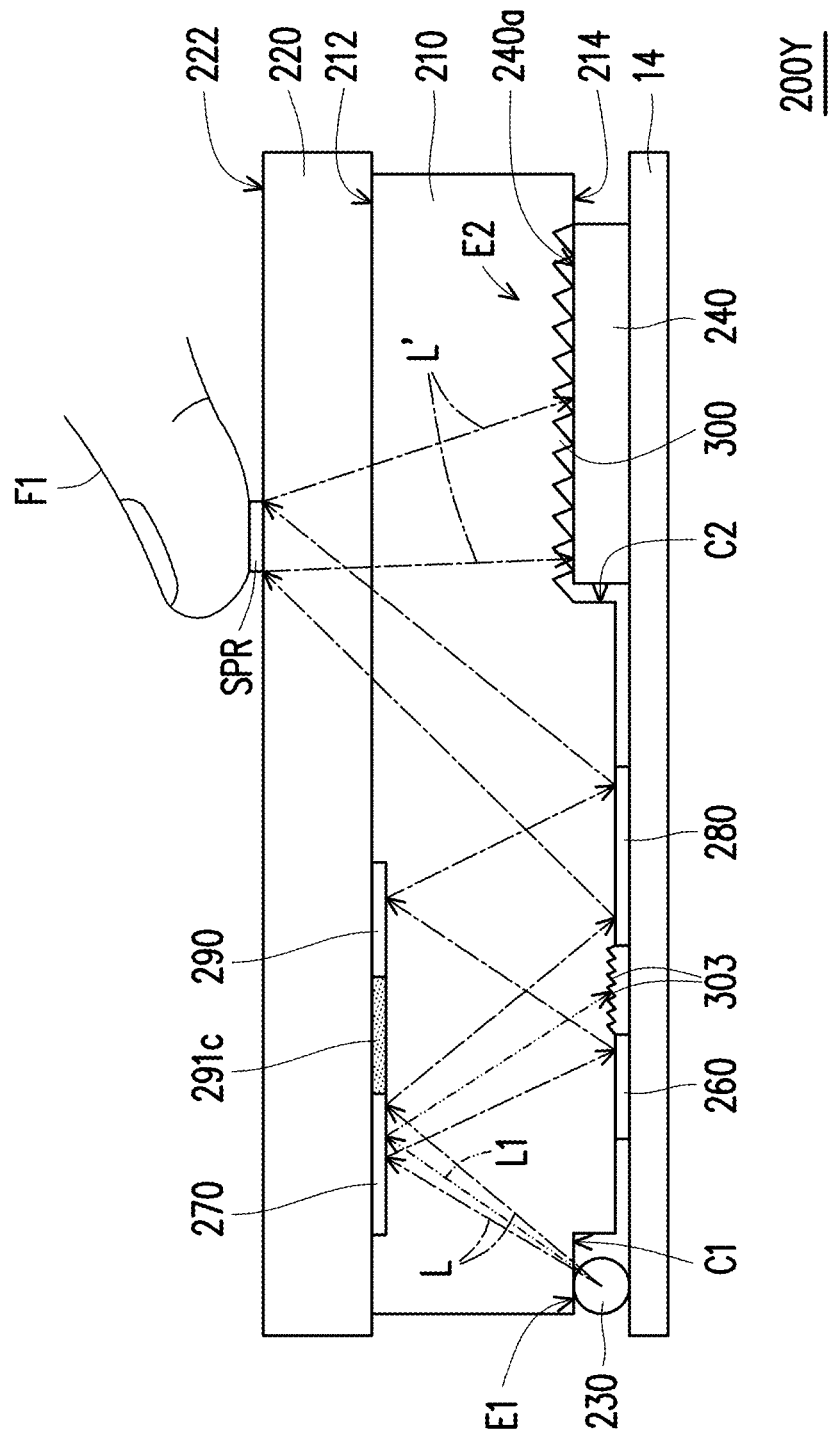
FIG. 55 is a schematic sectional view of a bio-sensing apparatus according to an embodiment of the invention.

Please refer to FIG. 55. FIG. 55 is a cross-sectional view depicting a bio-sensing apparatus according to another embodiment of the present disclosure. The bio-sensing apparatus 200Y of FIG. 55 is the same as the bio-sensing apparatus 200W of FIG. 53 or is denoted with the same component symbols corresponding to FIG. 53, and thus necessary details are not repeated.

In the embodiment of FIG. 55, the bio-sensing apparatus 200Y includes the light absorbing element 291c disposed on the second reflective element 270 and the fourth reflective element 290, and the light guide 210 includes a plurality of optical microstructures 303 disposed between the first reflective element 260 and the third reflective element 280.

In this embodiment, the distributed location of the plurality of optical microstructures 303 does not overlap with the second reflective element 270 and the fourth reflective element 290 in the thickness direction of the light guide 210. In addition, the light absorbing element 291c and the first reflective element 260 at least partially overlap in the thickness direction of the light guide 210, but the light absorbing element 291c and the third reflective element 280 do not overlap in the thickness direction of the light guide 210.

The light absorbing element 291c and the optical microstructures 303 of the present embodiment can allow the stray light L1 that does not follow along a predetermined path emitting out from the light guide 210 and being absorbed by the substrate 14 or directly absorbed by the light absorbing element 291c, so as to avoid the sensing element 240 receiving stray light from the signal light beam L'. In addition, the light absorbing element 291c and the optical microstructures 303 can be configured to increase the image capturing area and make the signal light beam L' transmit to the sensing element 240 more uniformly, thereby improving imaging quality.

Figure 56:
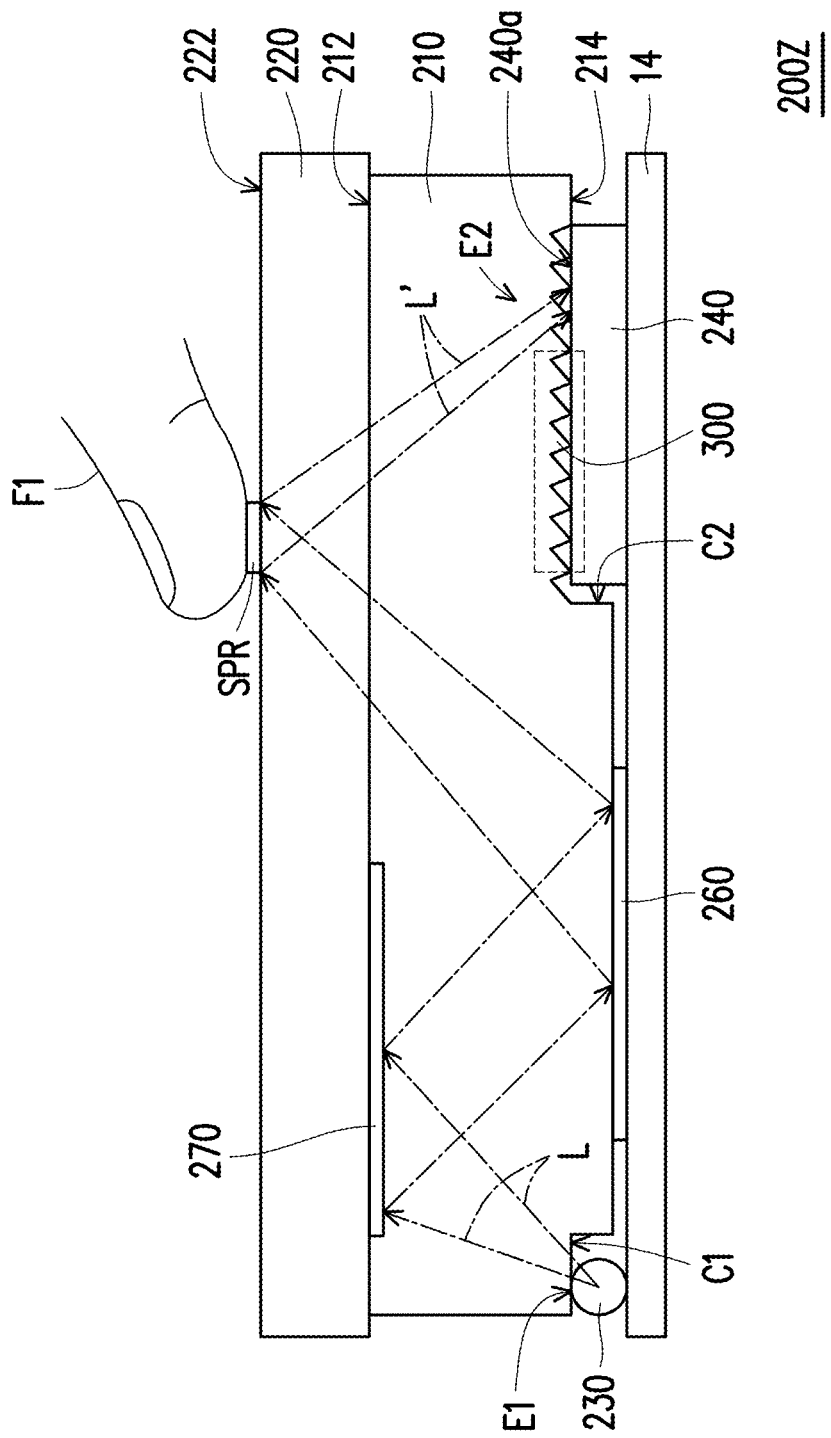
FIG. 56 is a schematic sectional view of a bio-sensing apparatus according to an embodiment of the invention.

Please refer to FIG. 56. FIG. 56 is a cross-sectional view of a bio-sensing apparatus according to an embodiment of the present disclosure. The bio-sensing apparatus 200Z of FIG. 56 is the same as the bio-sensing apparatus 200U of FIG. 47 or is denoted with the same component symbols corresponding to FIG. 47, and thus unnecessary details are not repeated.

In this embodiment, the bio-sensing apparatus 200Z does not include the light transmitting element 220 as shown in FIG. 47. Accordingly, after the light beam L generated by the light-emitting element 230 enters of the light guide 210 through the light incident portion E1, the light beam L is sequentially reflected by the second reflective element 270 and the first reflective element 260, then transmitting in the light guide 210, and then causing total reflection at the interface of the light guide 210 and the environmental medium, which is the surface of the top surface 212 of the light guide 210.

In other words, the surface located on the top surface 212 of the light guide 210 may be served as a contact surface to be contacted by the object F1. When the object F1 (e.g. a finger) contacts the light guide 210 by the top surface 212 of the light guide 210, the ridges of the finger make the light beam L not to be totally reflected, and the sensing element 240 obtains the dark lines corresponding to the ridges of the finger. On the other hand, the valleys of the finger do not touch the top surface 212 of the light guide 210, and the other portion of the light beam L can still be totally reflected to form a signal light beam L'. The signal light beam L' is projected toward the light emitting portion E2 of the light guide 210 and directed to the light receiving surface 240a of the sensing element 240 by the plurality of enhanced transmission microstructures 300 of the light guide 210. Subsequently, the light beam L' received by the sensing element 240 is performed an image process by an image processing component to obtain the fingerprint image of the object F1 for identification.

Figure 57:
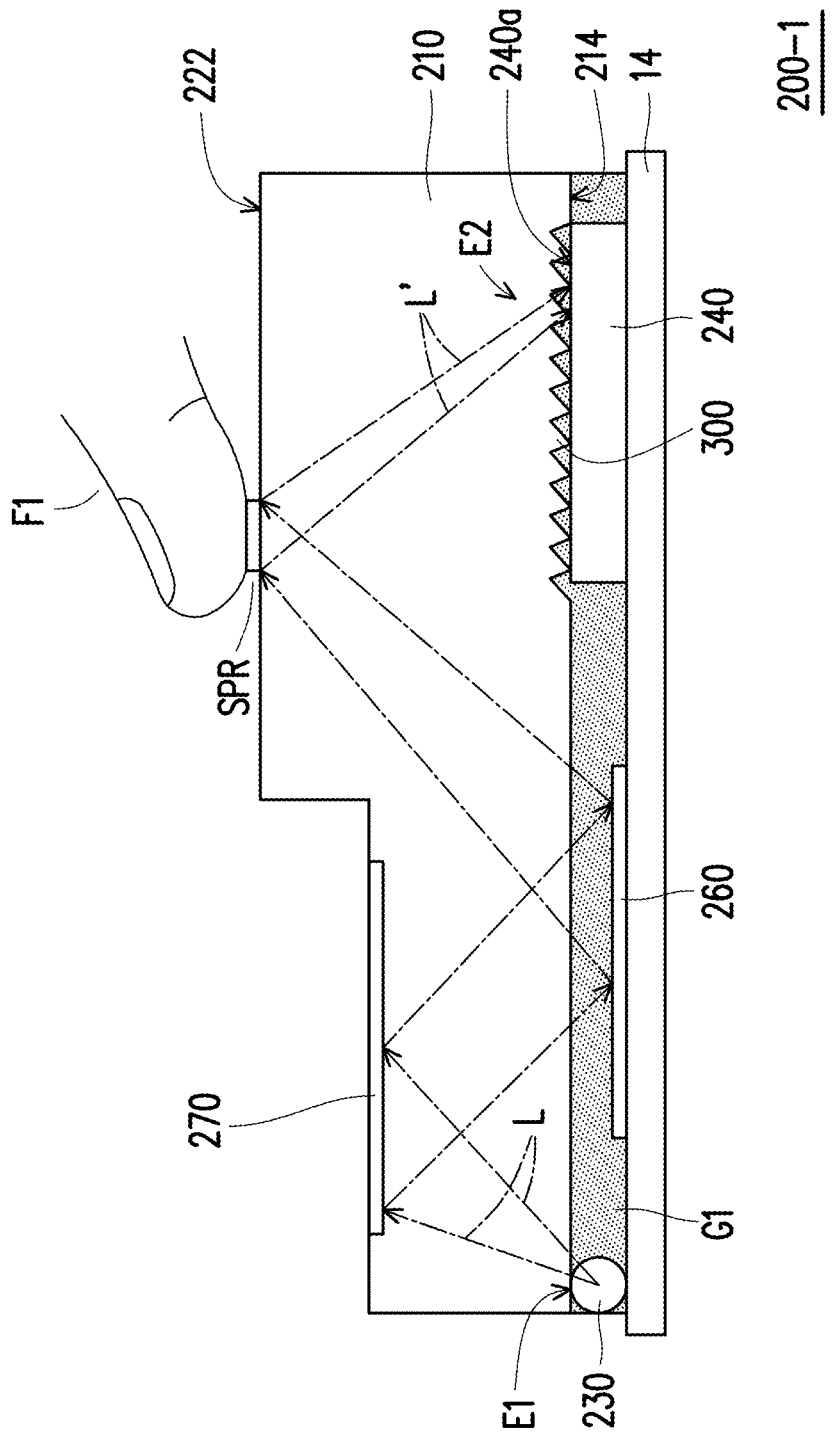
FIG. 57 is a schematic sectional view of a bio-sensing apparatus according to an embodiment of the invention.

FIG. 57 is a cross-sectional view of a bio-sensing apparatus according to an embodiment of the present disclosure. The bio-sensing apparatus 200-1 of this embodiment is the same as the bio-sensing apparatus 200Z of FIG. 56 or is denoted with the same component symbols corresponding to FIG. 56, and thus necessary details are not repeated.

In the present embodiment, the bottom surface 214 of the light guide 210 does not have the first recessed portion C1 and the second recessed portion C2. That is to say, the surface of the light guide 210 on the bottom surface 214 is a flat surface, but the plurality of enhanced transmission microstructures 300 are disposed on the light emitting portion E2 on the bottom surface 214.

In addition, the bio-sensing apparatus 200-1 in this embodiment further includes an optical adhesive G1. The optical adhesive G1 is located between the light guide 210 and the substrate 14 to fix the light guide 210 on the substrate 14, and the light-emitting element 230 and the sensing element 240 are embedded in the optical adhesive G1. Further, the refractive index of the optical adhesive G1 may be substantially the same as that of the light guide 210, for example, may be greater than or equal to 1.4 and less than or equal to 1.6. Therefore, when the light beam L enters the optical adhesive G1 by the light guide 210, or enters the light guide 210 by the optical adhesive G1, the light beam L will follow the predetermined optical path without generating refraction. It should be noted that the optical adhesive G1 does not fill the gap between the sensing element 240 and the light emitting portion E2 (the plurality of enhanced transmission microstructures 300). Therefore, the plurality of enhanced transmission microstructures 300 disposed on the light emitting portion E2 can significantly reduce the probability of the signal light beam L' being totally reflected again at the light emitting portion E2, so as to improve the imaging quality of the sensing element 240.

In addition, in the present embodiment, another recessed portion C3 is disposed on the surface of the top surface 212 of the light guide 210, and the position of the recessed portion C3 corresponds to the position of the second reflective element 270 so as to reduce a portion of the thickness of the light guide 210, thus providing a thinner bio-sensing apparatus for various products.

Moreover, the bio-sensing apparatus 200U-200Y, 200-1 respectively include surface plasma resonance layers SPR. Functions of the surface plasma resonance layers SPR of the bio-sensing apparatuses 200U-200Y, 200-1 and a function of the surface plasma resonance layer SPR of the above bio-sensing apparatus 100 are the same, and which will not be repeated here.

Figure 58:
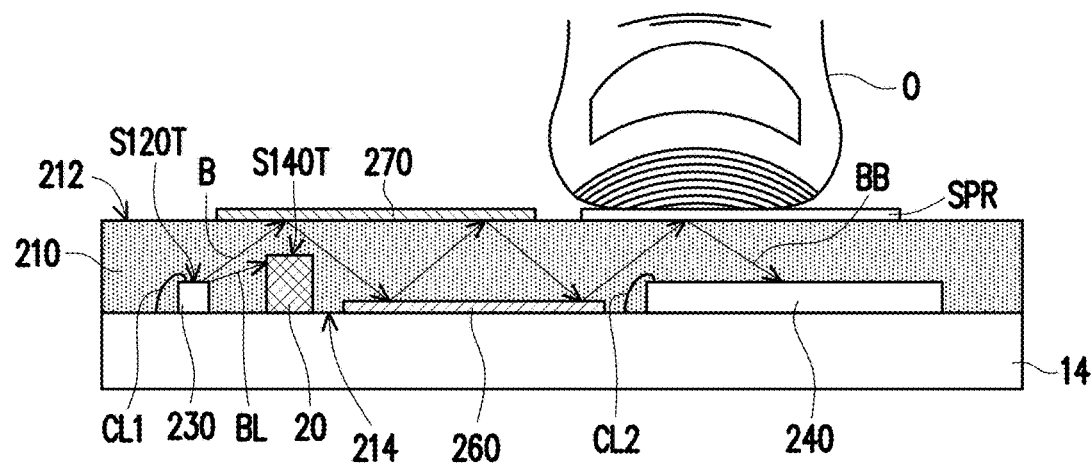
FIG. 58 is a cross-sectional schematic diagram illustrating one aspect of a bio-sensing apparatus according to an embodiment of the invention.

FIG. 58 is a cross-sectional schematic diagram illustrating one aspect of a bio-sensing apparatus according to an embodiment of the invention. Referring to FIG. 58, a bio-sensing apparatus 200-2 is adapted to capture a biometric feature of an object O. In the exemplary embodiment, the object O is, for example, a finger, and the biometric feature is, for example, a fingerprint or a vein, but the invention is not limited hereto. For example, in another embodiment, the object O may also be a palm, and the biometric feature may be a palm print.

The bio-sensing apparatus 200-2 includes a substrate 14, a light-emitting element 230, a sensing element 240, a light shielding element 20, a first reflective element 260, a light guide 210, and a second reflective element 270.

The substrate 14 is used as a carrier board of the foregoing components, and the substrate 14 may include a circuit. For example, the substrate 14 is a printed circuit board (PCB), a flexible printed circuit board (FPCB), a glass carrier board including a circuit, or a ceramic substrate including a circuit, but is not limited hereto.

The light-emitting element 230 is disposed on the substrate 14, and the light-emitting element 230 is electrically connected to the circuit on the substrate 14. For example, the bio-sensing apparatus 200-2 further includes a connecting line (also known as connecting wire) CL1, and the light-emitting element 230 is electrically connected to the circuit on the substrate 14 via the connecting line CL1, but the invention is not limited hereto. The light-emitting element 230 is adapted to provide a beam B for illuminating the object O.

The sensing element 240 is disposed on the substrate 14 and is located next to the light-emitting element 230. Moreover, the sensing element 240 is electrically connected to the circuit on the substrate 14. For example, the bio-sensing apparatus 200-2 further includes a connecting line CL2, and the sensing element 240 is electrically connected to the circuit on the substrate 14 via the connecting line CL2, but the invention is not limited hereto. The sensing element 240 is adapted to receive a portion (e.g., a beam BB) of the beam B reflected by the object O.

The light shielding element 20 is disposed on the substrate 14 and is located between the light-emitting element 230 and the sensing element 240. The light shielding element 20 is adapted to shield a large-angle beam (e.g., a beam BL) emitted by the light-emitting element 230 to avoid interference caused by the large-angle beam directly irradiated to the sensing element 240. For example, the light shielding element 20 is made of a light-absorbing material or is formed by forming a light-absorbing layer on a transparent bulk material. Moreover, a height of the light shielding element 20 may be greater than or equal to a height of the light-emitting element 230 and may be smaller than a height of the light guide 210. In other words, a top surface S140T of the light shielding element 20 may be higher than a top surface S120T of the light-emitting element 230 or is flush with the top surface S120T of the light-emitting element 230. In addition, the top surface S140T of the light shielding element 20 is lower than a top surface S160T of the light guide 210 to allow a partial beam (e.g., the beam B) emitted by the light-emitting element 230 to pass through. In any embodiment of the invention, the light shielding element 20 may be formed by curing a transparent colloid.

The first reflective element 260 is disposed on the substrate 14 and is located between the light shielding element 20 and the sensing element 240. The first reflective element 260 is adapted to reflect the beam B transmitted towards the substrate 14, such that the beam B is transmitted in a direction away from the substrate 14. For example, the first reflective element 260 is a reflective plate or is a reflecting layer formed on the substrate 14 by at least one of electroplating, printing, etching, adhesion, and coating.

The light guide 210 is disposed on the substrate 14 and covers the light-emitting element 230, the sensing element 240, the light shielding element 20, and the first reflective element 260. The light guide 210 is, for example, formed by curing a transparent colloid in a heating process or a light irradiation process. The transparent colloid is, for example, an epoxy, a silicone gel, an optical gel, a resin, or another adequate transparent material.

The second reflective element 270 is disposed above the light shielding element 20 and is located between the light-emitting element 230 and the sensing element 240. Specifically, the second reflective element 270 is located on at least a transmission path of the beam B that comes from the light-emitting element 230 and is not shielded by the light shielding element 20 to reflect the beam B transmitted towards the top surface S160T of the light guide 210, such that the beam B is transmitted towards the first reflective element 260. For example, the second reflective element 270 is a reflective plate or is a reflecting layer formed on the light guide 210 by at least one of electroplating, printing, etching, adhesion, and coating.

In the exemplary embodiment, the second reflective element 270 is disposed on the top surface S160T of the light guide 210 but is not limited hereto. The second reflective element 270 may extend from above the light shielding element 20 towards above the first reflective element 260, and the second reflective element 270 exposes the sensing element 240. The second reflective element 270 may partially overlap with the first reflective element 260 but is not limited hereto. In another embodiment, the second reflective element 270 and the first reflective element 260 fully overlap or do not overlap with each other. Moreover, the first reflective element 260 and the second reflective element 270 may have the same or different reflectivities.

Since the first reflective element 260 and the second reflective element 270 contribute to multiple reflections of the beam B in the light guide 210, the beam B transmitted in the bio-sensing apparatus 200-2 is more uniformized, and the object O thereby receives light in a more uniform manner, which leads the sensing element 240 to capture a complete biometric feature image. Accordingly, the bio-sensing apparatus 200-2 exhibits excellent image capturing quality.

In the exemplary embodiment, the object O is directly pressed on the top surface S160T of the light guide 210 to perform a biometric identification. In an embodiment, the bio-sensing apparatus 200-2 further includes a protective cover plate (not illustrated) or a protective film (not illustrated). The protective cover plate or the protective film is disposed on the light guide 210 and the second reflective element 270, and the object O is pressed on a surface of the protective cover plate or the protective film away from the second reflective element 270 to perform the biometric identification. The protective cover plate or the protective film protects the light guide 210 and the second reflective element 270 located below against scratching, for example.

FIG. 59 to FIG. 63 are cross-sectional schematic diagrams respectively illustrating other aspects of the bio-sensing apparatus according to the embodiment of FIG. 58, wherein the same components are represented by the same numerals and will not be repeatedly described below.

Figure 59:
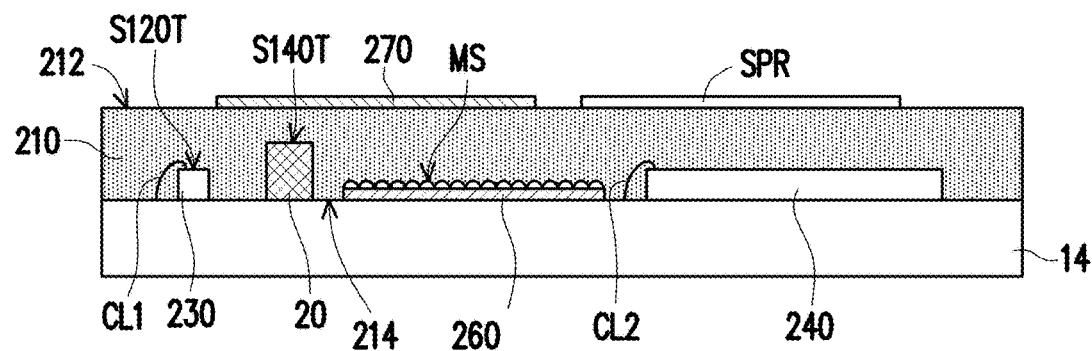
FIG. 59 to FIG. 63 are cross-sectional schematic diagrams respectively illustrating other aspects of the bio-sensing apparatus according to the embodiment of FIG. 58

Referring to FIG. 59, the main differences between a bio-sensing apparatus 200-3 and the bio-sensing apparatus 200-2 of FIG. 58 are described below. In the bio-sensing apparatus 200-3, a plurality of microstructures MS may be formed on the surface of at least one of the substrate 14, the first reflective element 260, the light guide 210, and the second reflective element 270 to increase a reflection amount of the beam B and cause the beam B to be more uniformized. FIG. 59 schematically illustrates a plurality of microstructures MS formed on the surface of the first reflective element 260 away from the substrate 14, but the invention is not limited hereto. In another embodiment, the plurality of microstructures MS are formed on a region of the substrate 14 other than the region disposed with the foregoing components. The top surface S160T of the light guide 210 may be formed with the plurality of microstructures MS, and the second reflective element 270 is disposed on at least a portion of the plurality of microstructures MS. The surface of the second reflective element 270 facing the substrate 14 or the surface away from the substrate 14 may be formed with the plurality of microstructures MS.

It is noted that the plurality of microstructures MS may be thoroughly or partially disposed on the foregoing components, and the plurality of microstructures MS may be disposed on the foregoing components continuously or at an interval. Moreover, in any one implementable exemplary embodiment of the invention, the plurality of microstructures MS may be disposed on the first reflective element 260 or the second reflective element 270 by partial attachment. For example, the plurality of microstructures MS and the first reflective element 260 (or the second reflective element 270) may be attached to each other through an annular adhesive layer (not illustrated), wherein the annular adhesive layer is located between a portion of the plurality of microstructures MS and a portion of the first reflective element 260 (or the second reflective element 270), and the adhesive layer is not disposed between the other portion of the plurality of microstructures MS and the other portion of the first reflective element 260 (or the second reflective element 270), such that the plurality of microstructures MS, the annular adhesive layer, and the first reflective element 260 (or the second reflective element 270) enclose and form an air gap layer (not illustrated).

In the framework of FIG. 59, the bio-sensing apparatus 200-3 may further include at least one protective cover plate (also known as transparent sheet), at least one cover sheet (not illustrated) or at least one protective film (not illustrated) disposed on the light guide 210 and the second reflective element 270. Reference may be made to the relevant paragraphs above for relevant descriptions, which will not be repeated here.

Figure 60:
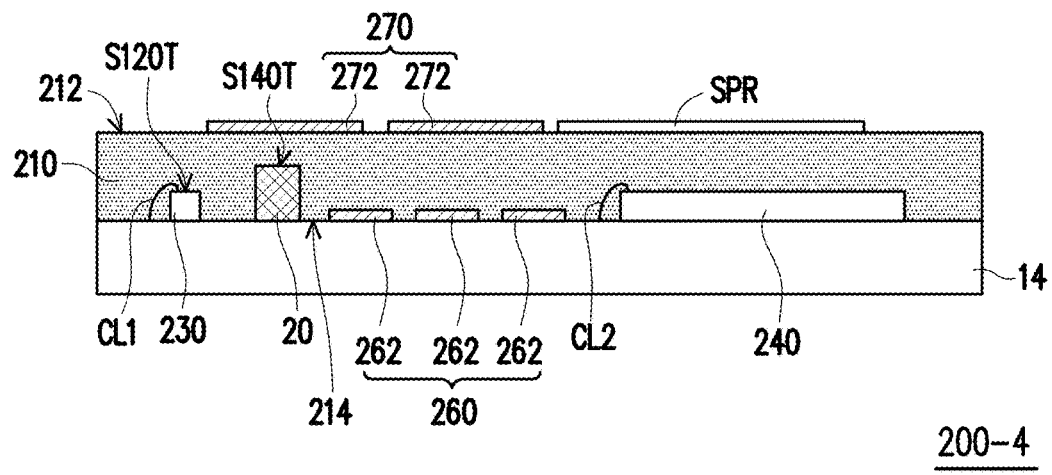

Referring to FIG. 60, the main differences between a bio-sensing apparatus 200-4 and the bio-sensing apparatus 200-2 of FIG. 58 are described below. In the bio-sensing apparatus 200-4, the first reflective element 260 includes a plurality of light-reflecting portions 262 arranged at an interval, and the second reflective element 270 includes a plurality of light-reflecting portions 272 arranged at an interval. Specifically, the first reflective element 260 and the second reflective element 270 are respectively composed of one or more light-reflecting portions (e.g., one or more reflective plates or one or more reflecting layers). When the reflective element is composed of a plurality of light-reflecting portions, the light-reflecting portions may be arranged at an interval. The arrangement at an interval includes arrangement at an equal interval and arrangement at unequal intervals (random distribution). In another exemplary embodiment, only one of the first reflective element 260 and the second reflective element 270 includes the plurality of light-reflecting portions arranged at an interval.

In the framework of FIG. 60, the bio-sensing apparatus 200-4 may further include a protective cover plate (not illustrated) or a protective film (not illustrated) disposed on the light guide 210 and the second reflective element 270. Moreover, a plurality of microstructures MS (see FIG. 59) may be formed on the surface of at least one of the substrate 14, the first reflective element 260 (the light-reflecting portions 262), the light guide 210, and the second reflective element 270 (the light-reflecting portions 272). Reference may be made to the relevant paragraphs above for relevant descriptions, which will not be repeated here.

Figure 61:
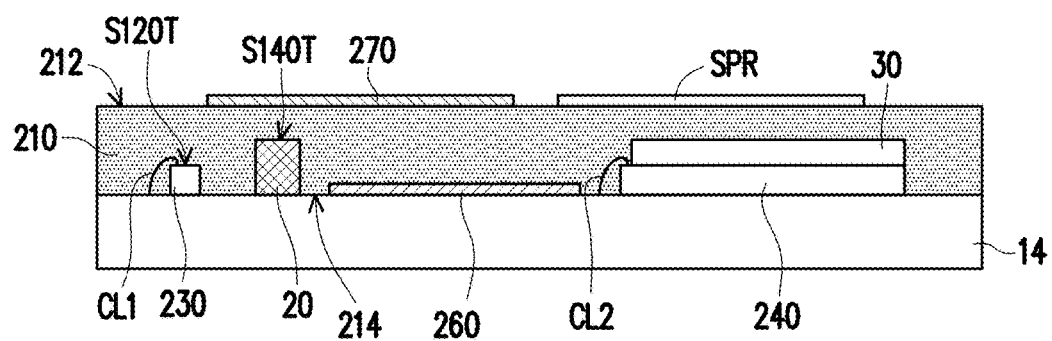

Referring to FIG. 61, the main differences between a bio-sensing apparatus 200-5 and the bio-sensing apparatus 200-2 of FIG. 58 are described below. In the bio-sensing apparatus 200-5, the bio-sensing apparatus 200-5 further includes a spatial filter element 30 disposed on the sensing element 240 and located between the light guide 210 and the sensing element 240. The spatial filter element 30 is adapted to collimate the beam transmitted to the sensing element 240. In another embodiment, the spatial filter element 30 is replaced by a grating. Moreover, the spatial filter element 30 and the grating may be fixed on the sensing element 240 through an adhesive layer (not illustrated) or a fixing mechanism (not illustrated). Alternatively, the spatial filter element 30 may be replaced by a fiber array described in the US prior application Ser. No. 15/151,471 or the CN prior application serial no. 201810194406.6 filed by the Applicant.

In the framework of FIG. 61, the bio-sensing apparatus 200-5 may further include a protective cover plate (not illustrated) or a protective film (not illustrated) disposed on the light guide 210 and the second reflective element 270. Moreover, a plurality of microstructures MS (see FIG. 59) may be formed on the surface of at least one of the substrate 14, the first reflective element 260, the light guide 210, and the second reflective element 270. In addition, at least one of the first reflective element 260 and the second reflective element 270 may include a plurality of light-reflecting portions arranged at an interval (see FIG. 60). Reference may be made to the relevant paragraphs above for relevant descriptions, which will not be repeated here.

Figure 62:
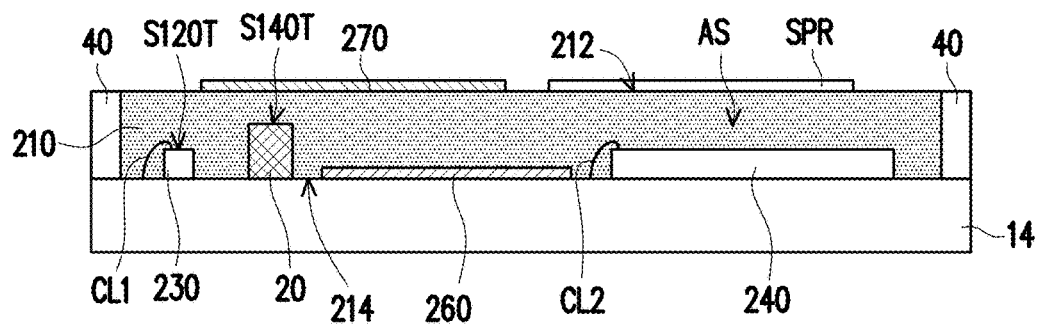

Referring to FIG. 62, the main differences between a bio-sensing apparatus 200-6 and the bio-sensing apparatus 200-2 of FIG. 58 are described below. In the bio-sensing apparatus 200-6, the bio-sensing apparatus 200-6 further includes a wall structure (also known as protective structure) 40. The wall structure 40 is disposed on the substrate 14, wherein the wall structure 40 and the substrate 14 form an accommodation space AS for accommodating the light-emitting element 230, the sensing element 240, the light shielding element 20, and the first reflective element 260. In an exemplary embodiment, the wall structure 40 and the substrate 14 may be integrally formed. For example, the wall structure 40 and the substrate 14 are formed by removing a block from a substrate material, wherein a space occupied by the block before removal is the accommodation space AS. In another exemplary embodiment, the wall structure 40 is fixed on the substrate 14 through a mechanic element or an adhesive layer (not illustrated), and the wall structure 40 and the substrate 14 may have the same or different materials.

In the framework of FIG. 62, the bio-sensing apparatus 200-6 may further include a protective cover plate (not illustrated) or a protective film (not illustrated) disposed on the light guide 210 and the second reflective element 270. Moreover, a plurality of microstructures MS (see FIG. 59) may be formed on the surface of at least one of the substrate 14, the first reflective element 260, the light guide 210, and the second reflective element 270. In addition, at least one of the first reflective element 260 and the second reflective element 270 may include a plurality of light-reflecting portions arranged at an interval (see FIG. 60). Furthermore, the bio-sensing apparatus 200-6 may further include a spatial filter element 30 (see FIG. 61), a grating or a fiber array (described in the prior application Ser. No. 15/151,471 filed by the Applicant) disposed on the sensing element 240 and located between the light guide 210 and the sensing element 240. Reference may be made to the relevant paragraphs above for relevant descriptions, which will not be repeated here.

Figure 63:
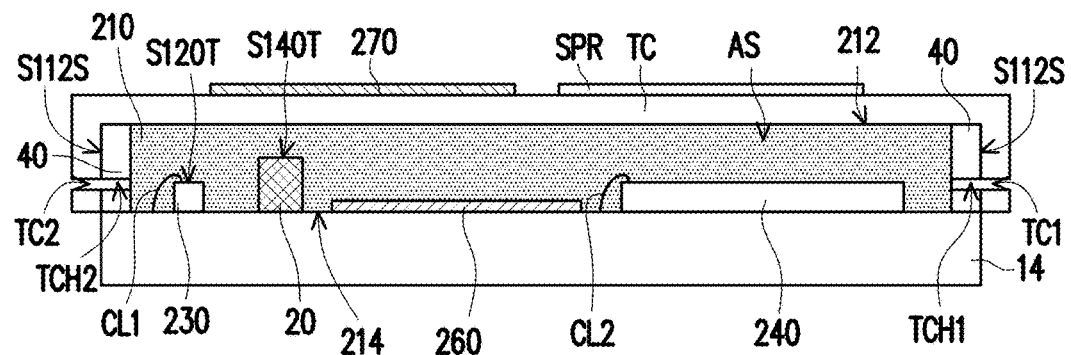

Referring to FIG. 63, the main differences between a bio-sensing apparatus 200-7 and the bio-sensing apparatus 200-6 of FIG. 62 are described below. In the bio-sensing apparatus 200-7, the bio-sensing apparatus 200-7 further includes a transparent cover TC. The transparent cover TC is disposed on the light guide 210 and covers the light-emitting element 230, the sensing element 240, the light shielding element 20, the first reflective element 260, the connecting line (also known as connecting wire) CL1, the connecting line CL2, and the wall structure 40. Moreover, the second reflective element 270 is disposed on the transparent cover TC.

The transparent cover TC includes a gel injection hole TC1 and a vacuum-pumping hole TC2. The gel injection hole TC1 is adapted to fill the transparent colloid for forming the light guide 210, and the vacuum-pumping hole TC2 is adapted to connect to a vacuum-pumping apparatus to pump out air in the accommodation space AS when the transparent colloid is filled in.

In the exemplary embodiment, the transparent cover TC further covers a side wall surface S112S of the wall structure 40, and the gel injection hole TC1 and the vacuum-pumping hole TC2 are respectively formed in a portion of the transparent cover TC covering the side wall surface S112S of the wall structure 40. The wall structure 40 includes a first through-hole TCH1 and a second through-hole TCH2. The first through-hole TCH1 and the second through-hole TCH2 are respectively formed in portions of the wall structure 40 located on two opposite sides of the substrate 14, wherein the first through-hole TCH1 is connected to the gel injection hole TC1, and the second through-hole TCH2 is connected to the vacuum-pumping hole TC2. However, the invention is not limited hereto. The gel injection hole TC1 and the vacuum-pumping hole TC2 may be formed in a portion of the top of the transparent cover TC located on the substrate 14, so that it is not necessary to form the first through-hole TCH1 and the second through-hole TCH2 in the wall structure 40.

In the framework of FIG. 63, the bio-sensing apparatus 200-7 may further include a protective cover plate, a cover sheet (not illustrated) or a protective film (not illustrated) disposed on the transparent cover TC and the second reflective element 270. Moreover, a plurality of microstructures MS (see FIG. 59) may be formed on the surface of at least one of the substrate 14, the first reflective element 260, the light guide 210, and the second reflective element 270. In addition, at least one of the first reflective element 260 and the second reflective element 270 may include a plurality of light-reflecting portions arranged at an interval (see FIG. 60). Furthermore, the bio-sensing apparatus 200-7 may further include a spatial filter element 30 (see FIG. 61), a grating or a fiber array (described in the US prior application Ser. No. 15/151,471 or the CN prior application serial no. 201810194406.6 filed by the Applicant) disposed on the sensing element 240 and located between the light guide 210 and the sensing element 240. Reference may be made to the relevant paragraphs above for relevant descriptions, which will not be repeated here.

Figure 64:
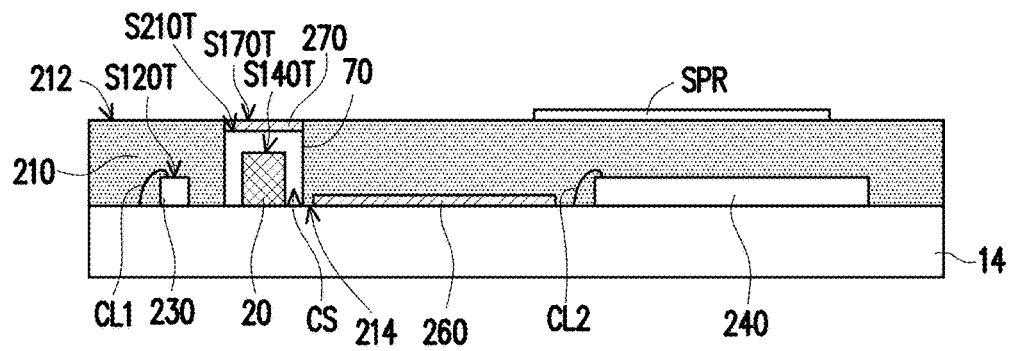
FIG. 64 is a cross-sectional schematic diagram illustrating one aspect of a bio-sensing apparatus according to an exemplary embodiment of the invention.

FIG. 64 is a cross-sectional schematic diagram illustrating one aspect of a bio-sensing apparatus according to an exemplary embodiment of the invention. Referring to FIG. 64, a bio-sensing apparatus 200-8 is similar to the bio-sensing apparatus 200-2 of FIG. 58, wherein the same components are represented by the same numerals and will not be repeatedly described below. The main differences between the bio-sensing apparatus 200-8 and the bio-sensing apparatus 200-2 of FIG. 58 are described below. In the bio-sensing apparatus 200-8, the bio-sensing apparatus 200-8 further includes a transparent base 70. The transparent base 70 is disposed on the substrate 14 and covers the light shielding element 20.

In the exemplary embodiments, the transparent base 70 is a transparent housing disposed to cover the light shielding element 20, and the transparent housing and the substrate 14 form an enclosed space S for accommodating the light shielding element 20. The light shielding element 20 may not fully fill the enclosed space S. In other words, a gap may exist between the light shielding element 20 and the transparent housing. The gap may be filled with an adhesive material for fixing the light shielding element 20 and the transparent housing but is not limited hereto. In another feasible embodiment, the transparent base 70 is a transparent layer formed on a side wall surface and a top surface of the light shielding element 20 by at least one of electroplating, printing, etching, adhesion, and coating, and the transparent layer may be made of one or more transparent materials.

In the exemplary embodiments, the transparent base 70 does not cover the first reflective element 260. In other words, the transparent base 70 does not overlap with the first reflective element 260. However, the invention is not limited hereto. In another embodiment, the transparent base 70 covers a portion of the first reflective element 260 adjacent to the transparent base 70, such that the transparent base 70 partially overlaps with the first reflective element 260.

The second reflective element 270 is disposed on a top surface S210T of the transparent base 70, wherein the top surface S170T of the second reflective element 270 is flush with the top surface 212 of the light guide 210. In other words, the top surface 5170T of the second reflective element 270 and the top surface 212 of the light guide 210 have the same height, but the invention is not limited hereto. In another embodiment, the top surface S170T of the second reflective element 270 is lower than the top surface 212 of the light guide 210, and the light guide 210 further covers the second reflective element 270 and the transparent base 70 located under the second reflective element 270.

In the framework of FIG. 64, the bio-sensing apparatus 200-8 may further include a protective cover plate (or a protective cover sheet, not illustrated) or a protective film (not illustrated) disposed on the light guide 210 and the second reflective element 270. Moreover, a plurality of microstructures MS (see FIG. 59) may be formed on the surface of at least one of the substrate 14, the first reflective element 260, the light guide 210, and the second reflective element 270. In addition, at least one of the first reflective element 260 and the second reflective element 270 may include a plurality of light-reflecting portions arranged at an interval (see FIG. 60). Furthermore, the bio-sensing apparatus 200-8 may further include a spatial filter element 30 (see FIG. 61) or a grating disposed on the sensing element 240 and located between the light guide 210 and the sensing element 240. Moreover, the bio-sensing apparatus 200-8 may further include a wall structure 40 (see FIG. 6). Reference may be made to the relevant paragraphs above for relevant descriptions, which will not be repeated here.

Figure 65:
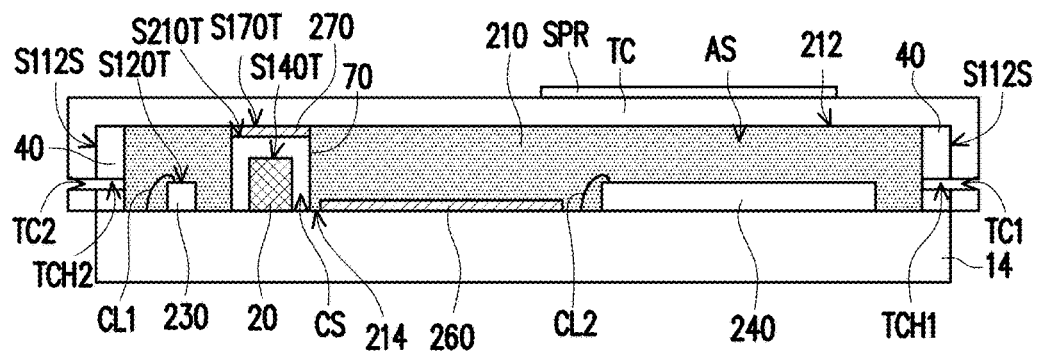
FIG. 65 is a cross-sectional schematic diagram illustrating another aspect of the bio-sensing apparatus according to an embodiment.

FIG. 65 is a cross-sectional schematic diagram illustrating another aspect of the bio-sensing apparatus according to an embodiment. Referring to FIG. 65, a bio-sensing apparatus 200-9 is similar to the bio-sensing apparatus 200-8 of FIG. 64, wherein the same components are represented by the same numerals and will not be repeatedly described below. The main differences between the bio-sensing apparatus 200-9 and the bio-sensing apparatus 200-8 of FIG. 64 are described below. In the bio-sensing apparatus 200-9, the bio-sensing apparatus 200-9 further includes the wall structure 40 (also known as protective structure) and the transparent cover TC. Reference may be made to the relevant paragraphs above for relevant descriptions of the wall structure 40 and the transparent cover TC, which will not be repeated here.

In the framework of FIG. 65, the transparent cover TC protects the light guide 210 and the second reflective element 270 located below. Therefore, it is not necessary to additionally dispose a protective cover plate or a protective film. Moreover, a plurality of microstructures MS (see FIG. 59) may be formed on the surface of at least one of the substrate 14, the first reflective element 260, the light guide 210, and the second reflective element 270. In addition, at least one of the first reflective element 260 and the second reflective element 270 may include a plurality of light-reflecting portions arranged at an interval (see FIG. 60). Furthermore, the bio-sensing apparatus 200-9 may further include a spatial filter element 30 (see FIG. 61) or a grating disposed on the sensing element 240 and located between the light guide 210 and the sensing element 240. Reference may be made to the relevant paragraphs above for relevant descriptions, which will not be repeated here.

Figure 66:
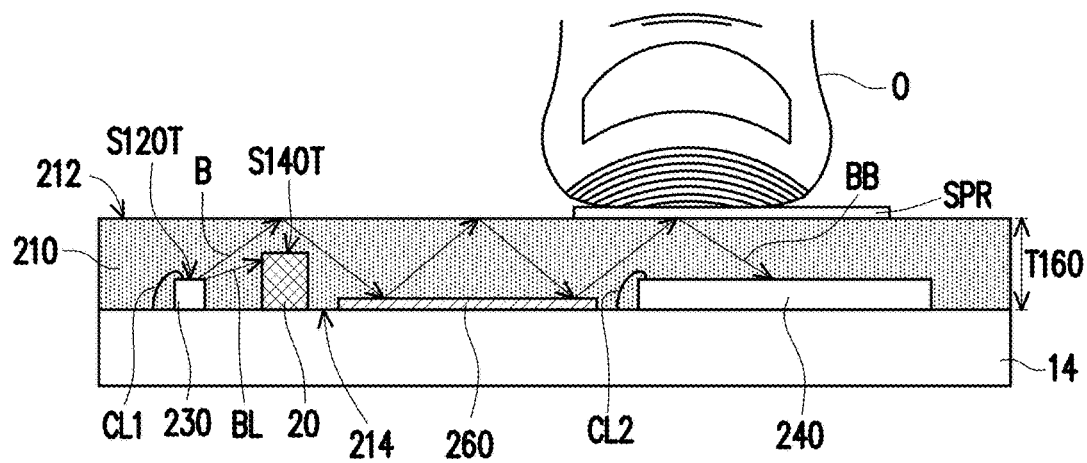
FIG. 66 is a cross-sectional schematic diagram illustrating one aspect of a bio-sensing apparatus according to an embodiment of the invention.

FIG. 66 is a cross-sectional schematic diagram illustrating one aspect of a bio-sensing apparatus according to an embodiment of the invention. Referring to FIG. 66, a bio-sensing apparatus 200-10 is similar to the bio-sensing apparatus 200-2 of FIG. 58, wherein the same components are represented by the same numerals and will not be repeatedly described below. The main differences between the bio-sensing apparatus 200-10 and the bio-sensing apparatus 200-2 of FIG. 58 are described below. In the bio-sensing apparatus 200-10, the second reflective element 270 in FIG. 58 is omitted. In this case, a portion of the beam B transmitted to the top surface 212 of the light guide 210 is transmitted to the first reflective element 260 through internal reflection. Specifically, when a thickness T160 of the light guide 210 is within a range from 0.3 mm to 1.8 mm, a portion of the beam transmitted to the top surface 212 of the light guide 210 and having an angle (the angle included between the beam B and the top surface 212) of no more than 45 degrees can be transmitted to the sensing element 240 via multiple reflections between the top surface 212 and the first reflective element 260, while the other portion of the beam transmitted to the top surface 212 of the light guide 210 and having an angle (the angle included between the beam B and the top surface 212) larger than 45 degrees is refracted out of the light guide 210.

Figure 67:
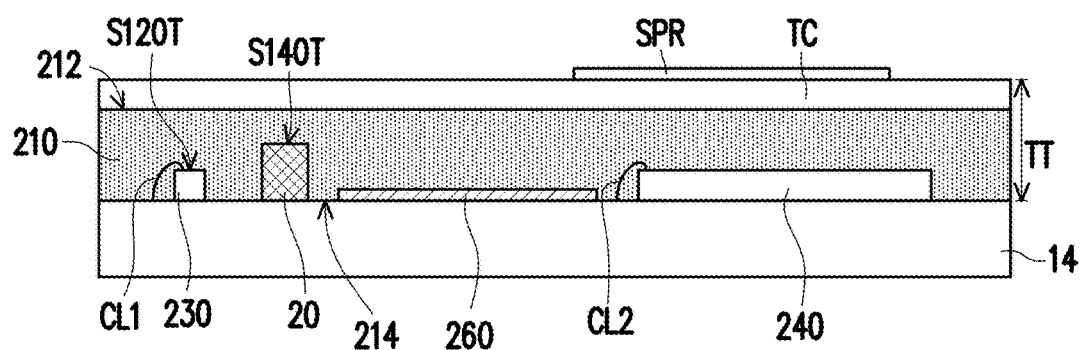
FIG. 67 is a cross-sectional schematic diagram illustrating another aspect of the bio-sensing apparatus according to an embodiment of the invention.

FIG. 67 is a cross-sectional schematic diagram illustrating another aspect of the bio-sensing apparatus according to an embodiment of the invention. Referring to FIG. 67, a bio-sensing apparatus 200-11 is similar to the bio-sensing apparatus 200-10 of FIG. 66, wherein the same components are represented by the same numerals and will not be repeatedly described below. The main differences between the bio-sensing apparatus 200-11 and the bio-sensing apparatus 200-10 of FIG. 66 are described below. In the bio-sensing apparatus 200-11, the bio-sensing apparatus 200-11 further includes a transparent cover TC. The transparent cover TC is adapted to protect the elements located below. Besides, the transparent cover TC allows beam to pass through, so that the beam from the light-emitting element 230 can sequentially pass through the light guide 210 and the transparent cover TC and be transmitted to the object in contact with the transparent cover TC, and the beam reflected by the object can sequentially pass through the transparent cover TC and the light guide 210 and be transmitted to the sensing element 240. For example, the transparent cover TC is a glass cover, but the invention is not limited thereto. In the case that the transparent cover TC is disposed on the light guide 210 and covering the light-emitting element 230, the sensing element 240, the light shielding element 20, the first reflective element 260, and the connecting lines CL1 and CL2, a total thickness TT of the light guide 210 and the transparent cover TC is within a range from 0.3 mm to 1.8 mm to facilitate internal reflection, so that at least a portion of the beam from the light-emitting element 230 can be transmitted to the object in contact with the transparent cover TC an then be transmitted to the sensing element 240.

In the framework of FIG. 66 and FIG. 67, a plurality of microstructures MS (see FIG. 59) may be formed on the surface of at least one of the substrate 14, the first reflective element 260, and the light guide 210. In addition, the first reflective element 260 may include a plurality of light-reflecting portions arranged at an interval (see FIG. 60). Moreover, at least one of the bio-sensing apparatus 200-10 and the bio-sensing apparatus 200-11 may further include a spatial filter element 30 (see FIG. 61), a grating or a fiber array (described in the prior application Ser. No. 15/151,471 filed by the Applicant) disposed on the sensing element 240 and located between the light guide 210 and the sensing element 240. Furthermore, at least one of the bio-sensing apparatus 200-10 and the bio-sensing apparatus 200-11 may further include the wall structure 40 disposed on the substrate 14 (see FIG. 62). Reference may be made to the relevant paragraphs above for relevant descriptions, which will not be repeated here.

Moreover, the bio-sensing apparatus 200-2-200-11 respectively include surface plasma resonance layers SPR. Functions of the surface plasma resonance layers SPR of the bio-sensing apparatuses 200-2-200-11 and a function of the surface plasma resonance layer SPR of the above bio-sensing apparatus 100 are the same, and which will not be repeated here.

Figure 68A:
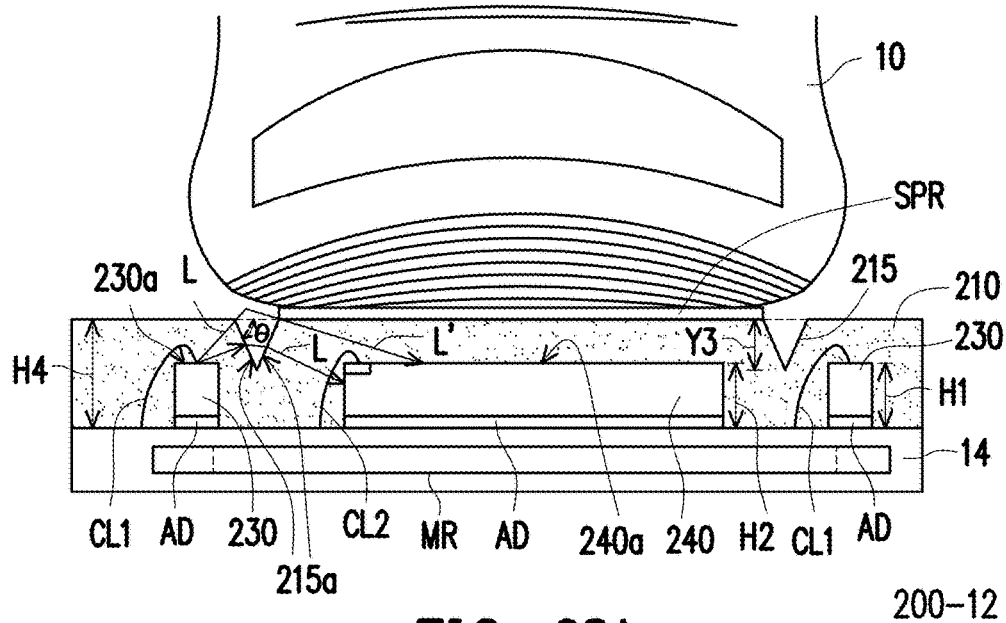
FIGS. 68A and 68B are respectively a schematic cross-sectional view and a schematic top view illustrating a bio-sensing apparatus according to an exemplary embodiment of the invention.
Figure 68B:
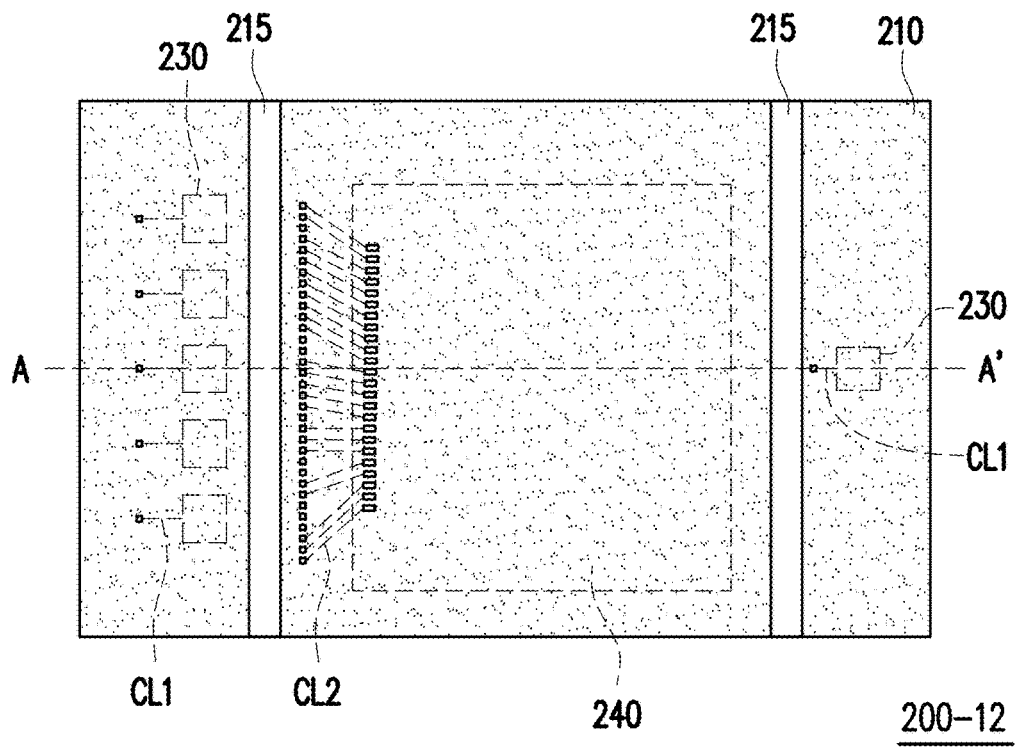

FIGS. 68A and 68B are respectively a schematic cross-sectional view and a schematic top view illustrating a bio-sensing apparatus according to an exemplary embodiment of the invention, wherein FIG. 68A is a schematic cross-sectional view taken along a sectional line A-A' of FIG. 68B. Referring to FIGS. 68A and 68B, a bio-sensing apparatus 100 is adapted to capture a biometric feature of an object 10 to be sensed. In the exemplary embodiment, the object 10 to be sensed is a finger, for example, and the biometric feature is a fingerprint or a vein, for example. However, the invention is not limited thereto. For example, in another embodiment, the object 10 to be sensed may also be a palm, and the biometric feature may be a palm print.

The bio-sensing apparatus 200-12 includes a substrate 14, a plurality of light emitting element 230, a sensing element 240, and a light guide 210.

In order to make a packaging structure of the bio-sensing apparatus 200-12 more applicable, a metal ring MR may be disposed in the substrate 14. The metal ring MR is located between an upper surface and a lower surface of the substrate 14 and surrounds a sensing region of the sensing element 240. Accordingly, when the object 10 to be sensed presses the light guide 210, the apparatus may start operating through charging by induction. Also, the packaging structure of the bio-sensing apparatus 200-12 may enter a temporarily suspended state when idling to save energy.

The light emitting element 230 are disposed on the substrate 14 and electrically connected to the substrate 14. Each of the light emitting element 230 has a light emitting surface 230a. A light beam L is emitted from the light emitting surface 230a of each of the light emitting element 230 toward the object 10 to be sensed.

The sensing element 240 is disposed on the substrate 14 and electrically connected to the substrate 14. In addition, the sensing element 240 is disposed beside the light emitting element 230 to receive portions (i.e., reflected light beams L' having fingerprint pattern information) of the light beams L reflected by the object 10 to be sensed.

In an exemplary embodiment, a pulse width modulation (PWM) circuit is integrated in the sensing element 240. By configuring the pulse width modulation circuit to control a light emitting time of the light emitting element 230 and an image capturing time of the sensing element 240, the light emitting time of the light emitting element 230 and the image capturing time of the sensing element 240 are synchronized, thereby exerting accurate control. However, the invention is not limited thereto.

The light guide 210 is disposed on the substrate 14 and covers the sensing element 240 and the light emitting element 230. The light guide 210 is formed by curing a transparent colloid, such as silica gel, resin, optical adhesive, epoxy resin, or the like, by performing a thermal process or an irradiating process. Therefore, in addition to preventing electrostatic damages to protect the sensing element 240 and the light emitting element 230 covered by the light guide 210, the light guide 210 also allows the light beams L emitted by the light emitting element 230 and the light beams L' reflected by the object 10 to be sensed to pass through.

At least one trench 215 is formed on a surface of the light guide 210 opposite to the sensing element 240. In addition, the at least one trench 215 is located between the sensing element 240 and the light emitting element 230. In the embodiment, the light emitting element 230 are located at opposite sides of the sensing element 240. In addition, the light guide 210 includes two trenches 215. However, the invention is not limited thereto.

In the embodiment, a depth H3 of the trench 215 is less than a thickness H4 of the light guide 210, namely H3<H4. In other words, for the ease of manufacturing, the trench 215 is not required to penetrate through the light guide 210.

In the exemplary embodiment, each trench 215 is a strip-like V-shape trench. In addition, each trench 215 has two inclined surfaces 215a. By adjusting a supplementary angle θ of an angle included between the inclined surface 215a of the two inclined surfaces 215a of the trench 215 that is closer to the corresponding light emitting element 230 and the surface (e.g., a contact surface of the object 10 to be sensed) of the light guide 210 opposite to the sensing element 240, a desirable light utilization rate is rendered. For example, the supplementary angle θ is in a range from 30 degrees to 45 degrees, and a depth H3 of the at least one trench 215 is determined based on a size of the supplementary angle θ. In other exemplary embodiments, a cross-sectional shape of each trench 215 may also be a shape of an inverted trapezoid, an inverted semi-circular shape, or other shapes. The semi-circular shape generally refers to shapes of an incomplete circle, and is not limited to a half of a circle.

The V-shaped trench is able to change traveling paths of the light beams L. Specifically, when traveling to the inclined surface 215a of the trench 215 that is closer to the light emitting element 230, the light beams L emitted by the light emitting element 230 may enter the trench 215 (i.e., emitted out of the light guide 210) through the inclined surface 215a that is closer to the light emitting element 230. A portion of the light beams entering the trench 215 may enter the light guide 210 again through the inclined surface 215a of the trench 215 that is closer to the sensing element 240. With the V-shaped trench changing the traveling paths of the light beams L, the light beams L emitted by the light emitting element 230 are prevented from being directly irradiated on the sensing element 240. Accordingly, an optical interference or crosstalk on the sensing element 240 is reduced, and an identification capability of the bio-sensing apparatus 200-12 is facilitated.

In the exemplary embodiment, a light transmitting medium in the trench 215 is air. However, the invention is not limited thereto. In another embodiment, the trench 215 may be filled with a transparent material whose refractive index is greater than a refractive index of the light guide 210, so as to more preferably prevent the light beams L emitted by the light emitting element 230 from being directly irradiated on the sensing element 240. The transparent material is a transparent material having a high refractive index, such as an optical adhesive curable by light or heat. However, the invention is not limited thereto.

Moreover, a height H2 of the sensing element 240 may be less than a height H1 of the light emitting element 230. In other words, the light emitting surfaces 230a of the light emitting element 230 may be higher than a sensing surface 240a of the sensing element 240 to further reduce the optical interference. The height H2 of the sensing element 240 refers to a distance from the sensing surface 240a of the sensing element 240 to the substrate 14, whereas the height H1 refers to a distance from the light emitting surfaces 230a of the light emitting element 230 to the substrate 14.

One way to make the height H2 of the sensing element 240 less than the height H1 of the light emitting element 230 includes modifying thicknesses of the respective components (the sensing element 240 and the light emitting element 230). Alternatively, under a circumstance that another layer is disposed between the respective components and the substrate 14, a thickness of the another layer may be modified, so that the height H2 of the sensing element 240 may be less than the height H1 of the light emitting element 230. For example, the bio-sensing apparatus 200-12 further includes a plurality of adhesive layers AD. The adhesive layers AD may be disposed between the light emitting element 230 and the substrate 14 and between the sensing element 240 and the substrate 14. The adhesive layers AD are adhesive colloids or double-sided tapes. A combined thickness of each of the light emitting element 230 and the adhesive layer AD below the light emitting device 230 is the height H1 of the light emitting device 230, whereas a combined thickness of the sensing element 240 and the adhesive layer AD below the sensing element 240 is the height H2 of the sensing element 240. By modifying the thickness of the adhesive layer AD below each of the light emitting element 230 and the thickness of the adhesive layer AD below the sensing element 240, the height H2 of the sensing element 240 is set to be less than the height H1 of the light emitting device 230. However, in another embodiment, the height H2 of the sensing element 240 may also be equal to or greater than the height H1 of the light emitting device 230.

In the embodiment, the bio-sensing apparatus 200-12 further includes a plurality of connecting wires CL1, CL2. The connecting wires CL1, CL2 respectively connect the sensing element 240 and the substrate 14 and connect the light emitting element 230 and the substrate 14. Accordingly, the sensing element 240 and the light emitting element 230 are respectively electrically connected to the substrate 14. A material of the connecting wires CL1, CL2 include gold, copper, or the like, for example. However, the invention is not limited thereto. In another embodiment, the sensing element 240 and the light emitting element 230 may also be respectively connected to the circuits on the substrate 14 through solder balls. The connecting wires CL1, CL2 may be omitted accordingly.

The bio-sensing apparatus 200-12 according to the embodiment may be manufactured according to the following. First of all, the light emitting element 230 and the sensing element 240 are adhered to the substrate 14 through the adhesive layers AD. In addition, the heights of the light emitting element 230 and the sensing element 240 may be modified by polishing. Then, the connecting wires CL1, CL2 are formed on the substrate 14 by a wiring device. The connecting wires CL1, CL2 are respectively connected to conductive pads of the light emitting element 230 and a conductive pad of the substrate 14 and connected to a conductive pad of the sensing element 240 and the conductive pad of the substrate 14. Then, a transparent colloid is formed on the substrate 14 by using a gluing device. In addition, the transparent colloid covers the light emitting element 230, the sensing element 240, and the connecting wires CL1, CL2. Subsequently, the transparent colloid is cured by performing a thermal process (such as a baking process) or an irradiating process (such as an ultraviolet light curing process). Then, by performing an etching process, a laser engraving process, or any other suitable patterning process, the at least one trench 215 is formed on the surface of the cured transparent colloid opposite to the sensing element 240. Accordingly, the light guide 210 is formed. In other embodiments, the light guide 210 and the at least one trench 215 may be integrally formed by using a mold. However, the invention is not limited thereto. In an embodiment, a plurality of image capturing units (including the light emitting element 230, the sensing element 240, and the light guide 210) may be manufactured on the substrate 14 at the same time, and a plurality of the bio-sensing apparatus 200-12 may be formed by performing a cutting process.

Accordingly, the bio-sensing apparatus 200-12 of the embodiment may be manufactured to be a fully planar fingerprint identification apparatus, thereby making the apparatus more compatible with other apparatuses in terms of assembling. Moreover, by applying a laminating and glue-injecting process, the bio-sensing apparatus 200-12 according to the embodiment may be manufactured in mass production, so as to reduce the manufacturing cost. Moreover, since the trench 215 of the light guide 210 is able to reduce the optical interference or crosstalk, a light shielding component may be omitted. As a consequence, the manufacturing process is simplified, the components required for manufacturing are reduced, and a module area may also be reduced.

Figure 69A:
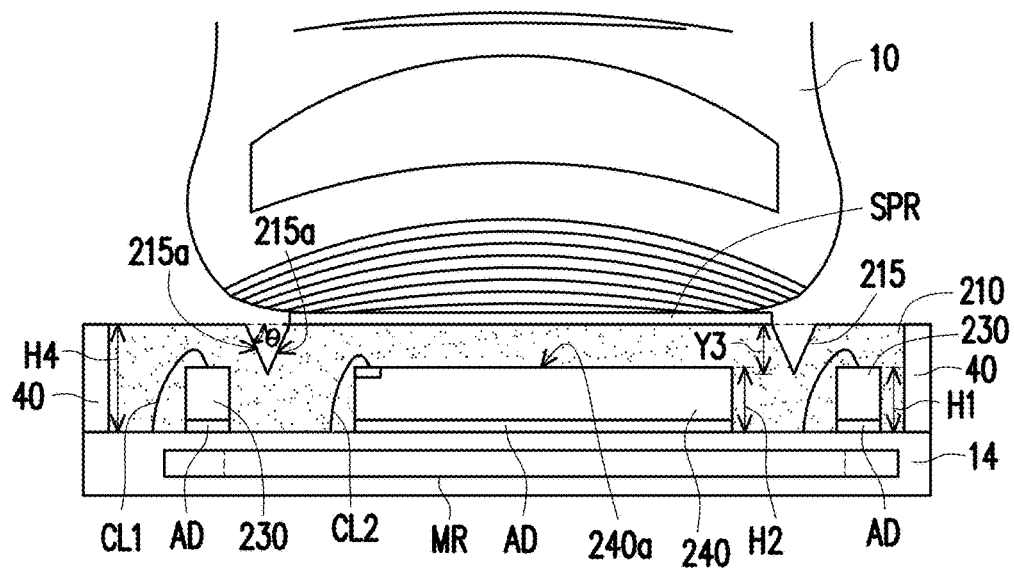
FIGS. 69A and 69B are respectively a schematic cross-sectional view and a schematic top view illustrating a bio-sensing apparatus according to an exemplary embodiment of the invention.
Figure 69B:
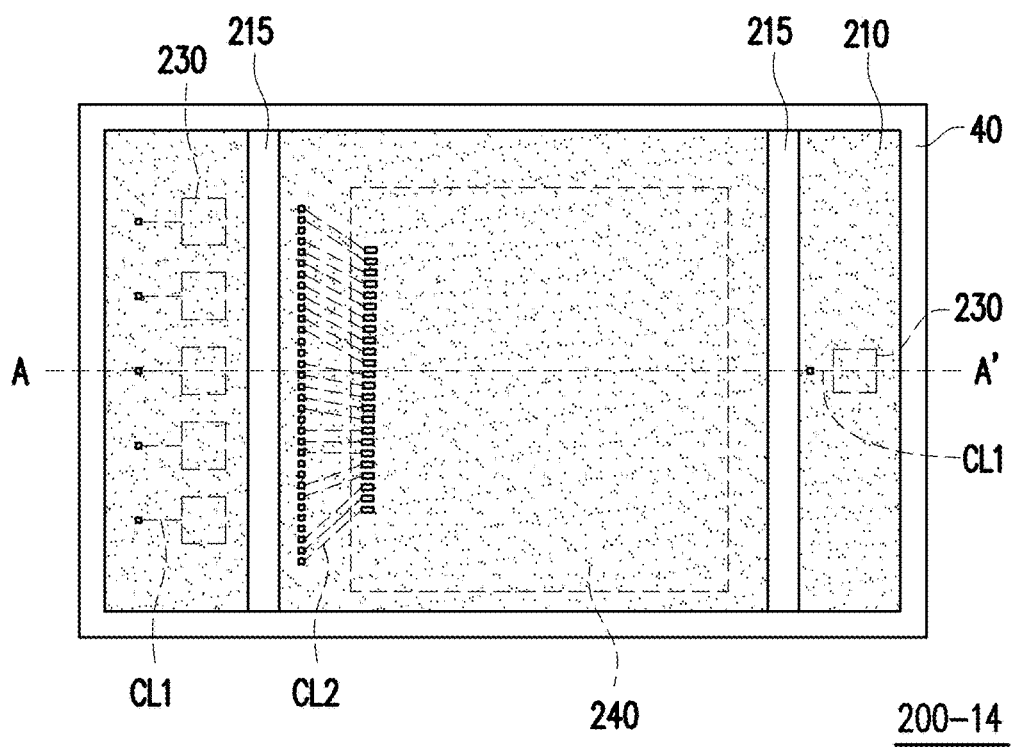

FIGS. 69A and 69B are respectively a schematic cross-sectional view and a schematic top view illustrating a bio-sensing apparatus according to an exemplary embodiment of the invention, wherein FIG. 69A is a schematic cross-sectional view taken along a sectional line A-A' of FIG. 69B. Referring to FIGS. 69A and 69B, a bio-sensing apparatus 200-13 is similar to the bio-sensing apparatus 200-12 of FIG. 68A. The main difference therebetween is described in the following. The bio-sensing apparatus 200-13 further includes at least one wall structure 40. The at least one wall structure 40 surrounds the sensing element 240 and the light emitting element 230. In addition, a material of the at least one wall structure 40 may be the same or different from a material of the substrate 14. It should be noted that the invention does not intend to impose a limitation on this regard.

During the manufacturing, the wall structure 40 may be formed after the sensing element 240 and the light emitting element 230 are disposed and before the light guide 210 is formed. Alternatively, the substrate 14 may be formed like a groove, and a protruding portion on an edge of the groove serves as the wall structure 40. In other words, the at least one wall structure 40 and the substrate 14 may be integrally formed. Disposing the at least one wall structure 40 reduces breakage of the connecting wires CL1, CL2 or dislocation and thus malfunctioning of the sensing element 240 due to an increased gluing pressure when the transparent colloid is injected. Accordingly, a yield of the bio-sensing apparatus 200-13 is increased. In addition, a preferable structural strength of the bio-sensing apparatus 200-13 is also rendered. In an embodiment, the wall structure 40 may be removed by performing a cutting process after the light guide 210 is formed. Accordingly, the bio-sensing apparatus 200-12 shown in FIG. 68A is formed.

Figure 70:
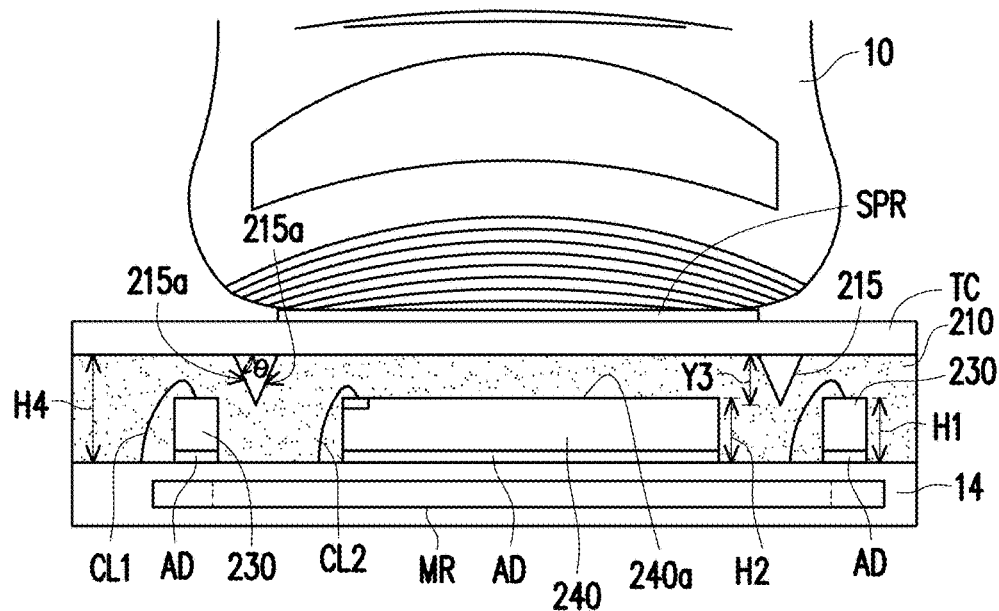
FIG. 70 is a schematic cross-sectional view illustrating a bio-sensing apparatus according to an embodiment of the invention.

FIG. 70 is a schematic cross-sectional view illustrating a bio-sensing apparatus according to an embodiment of the invention. Referring to FIG. 70, a bio-sensing apparatus 200-15 is similar to the bio-sensing apparatus 200-12 of FIG. 68A. The main difference therebetween is described in the following. The bio-sensing apparatus 200-15 further includes a cover plate TC. The cover plate TC is disposed on the light guide 210 and covers the at least one trench 215. In addition, the light transmitting medium in the at least one trench 215 includes air. A material of the cover plate TC includes glass or a transparent plastic material, for example. In an embodiment, the cover plate TC may be attached to the light guide 210 through an adhesive layer (not shown). The adhesive layer may be an adhesive colloid or a double-sided tape. Accordingly, an ability to block moisture is further reinforced and internal components in the bio-sensing apparatus 200-15 is protected. For example, the light guide 210 may be prevented from scratches. In another embodiment, the cover plate TC may be further fixed onto the light guide 210 by a fixing device. Accordingly, the adhesive layer may be omitted.

Under the configuration of FIG. 70, the bio-sensing apparatus 200-15 may further include the wall structure 40 of FIG. 69A. Relevant descriptions may be referred to the previous paragraphs and shall not be repeated in the following.

Figure 71:
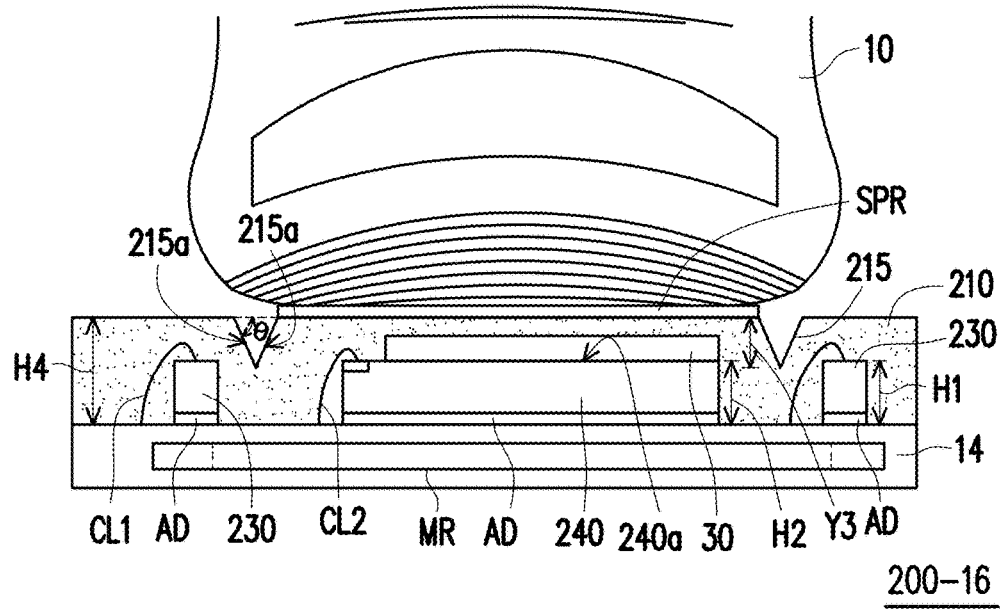
FIG. 71 is a schematic cross-sectional view illustrating a bio-sensing apparatus according to an embodiment of the invention.

FIG. 71 is a schematic cross-sectional view illustrating a bio-sensing apparatus according to an embodiment of the invention. Referring to FIG. 71, a bio-sensing apparatus 200-16 is similar to the bio-sensing apparatus 200-12 of FIG. 68A. The main difference therebetween is described in the following. The bio-sensing apparatus 200-16 further includes a spatial filter element 30. The spatial filter element 30 is disposed on the sensing element 240 and located between the light guide 210 and the sensing element 240 to collimate the light beams transmitted to the sensing element 240. As examples, a pinhole collimator or a fiber collimator may be chosen as the spatial filter element 30. Accordingly, a light intensity of the light beams reflected by the object to be sensed and then sensed by the sensing element 240 is increased, and an identification rate of the bio-sensing apparatus 200-16 is thus increased.

Under the configuration of FIG. 71, the bio-sensing apparatus 200-16 may further include the wall structure 40 of FIG. 69A or the cover plate TC of FIG. 70. Relevant descriptions may be referred to the previous paragraphs and shall not be repeated in the following.

Figure 72:
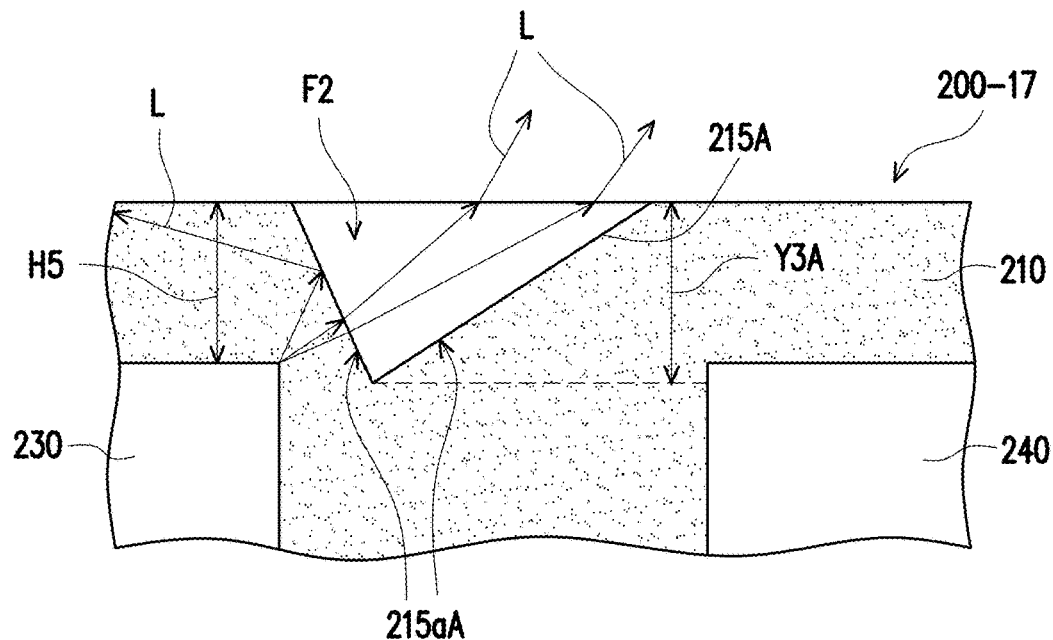
FIG. 72 is another schematic cross-sectional view illustrating a trench of a bio-sensing apparatus according to an embodiment of the invention.

FIG. 72 is another schematic cross-sectional view illustrating a trench of a bio-sensing apparatus according to an embodiment of the invention. Referring to FIG. 72, a bio-sensing apparatus 200-17 is similar to the bio-sensing apparatus 200-12 of FIG. 68A. The main difference therebetween is described in the following. In the bio-sensing apparatus 200-17, degrees of two vertex angles of a trench 215A are different. For example, a supplementary angle of an angle included between an inclined surface 215$a$A of the two inclined surfaces 215$a$A that is closer to the corresponding light emitting element 230 and the surface of the light guide 210 opposite to the sensing element 240 is 66.8 degrees, whereas a supplementary angle of an angle included between the inclined surface 215$a$A of the two inclined surfaces 215$a$A that is closer to the sensing element 240 and the surface of the light guide 210 opposite to the sensing element 240 is 32.5 degrees, and a base angle of the trench 215A is 90 degrees. In other embodiments, the degrees of the two vertex angles of the trench 215A may be exchanged or modified based on the design, and it should be understood that the invention is not limited thereto. In addition, a depth Y3A of the trench 215A is determined by the angles. In the embodiment, the depth Y3A of the trench 215A is greater than a distance H5 from the light emitting surfaces of the respective light emitting element 230 to the surface of the light guide 210 opposite to the sensing element 240. However, the invention is not limited thereto.

In the exemplary embodiment, the trench 215A is filled with a transparent material F2, and a refractive index of the transparent material F2 is greater than a refractive index of the light guide 210. Therefore, when the light beams L emitted by the light emitting element 230 are transmitted to the trench 215A, a portion of the light beams L may undergo total internal reflection by the inclined surface 215$a$A closer to the light-emitting element 230, and another portion of the light beams L may pass through the inclined surface 215$a$A closer to the light emitting element 230 and be transmitted in a direction away from the sensing element 240. Accordingly, the light beams L emitted by the light emitting element 230 may be prevented from being directly irradiated on the sensing element 240, so as to reduce the optical interference or crosstalk.

Figure 73:
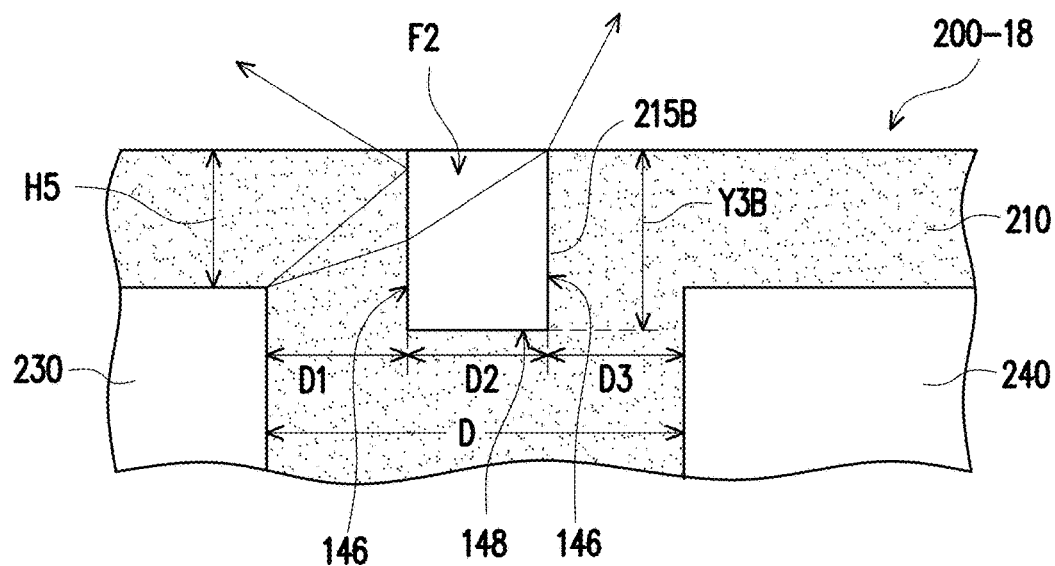
FIG. 73 is a schematic cross-sectional view illustrating a trench of a bio-sensing apparatus according to an embodiment of the invention.

FIG. 73 is a schematic cross-sectional view illustrating a trench of a bio-sensing apparatus according to an embodiment of the invention. Referring to FIG. 73, a bio-sensing apparatus 200-18 is similar to the bio-sensing apparatus 200-12 of FIG. 68A. The main difference therebetween is described in the following. In the bio-sensing apparatus 200-18, a trench 215B is a U-shaped trench. Specifically, the trench 215B has two side surfaces 146 opposite to each other and a bottom surface 148. Based on different manufacturing processes, the bottom surface 148 may be a planar surface, an inclined surface, or a curved surface.

In addition to changing the traveling paths of the light beams through refraction, with the side surface 146 closer to the light emitting element 230, the U-shaped trench also enables total internal reflection of light beams transmitted to the side surface 146, so that the light beams are transmitted in a direction away from the sensing element 240. In the embodiment, a depth Y3B of the trench 215B is greater than the distance H5 from the light emitting surfaces of the respective light emitting element 230 to the surface of the light guide 210 opposite to the sensing element 240. Therefore, most of the light beams transmitted to the side surface 146 of the trench 215B that is closer to the light emitting element 230 undergo the total internal reflection and are transmitted in a direction away from the sensing element 240.

In an exemplary embodiment, a width D2 of the trench 215B (such as the width D2 of the bottom surface 148), a distance D1 from one of the light emitting element 230 corresponding to the trench 215B to the trench 215B, and a distance D3 from the sensing element 240 to the trench 215B are all one-third of a distance D from the one of the corresponding light emitting element 230 to the sensing element 240. However, the invention is not limited thereto.

In the embodiment, the trench 215B is filled with a transparent material F2. A refractive index of the transparent material F2 is less than the refractive index of the light guide 210, so as to generate the total internal reflection. However, in other embodiments, the transparent material F2 may be omitted.

Figure 74A:
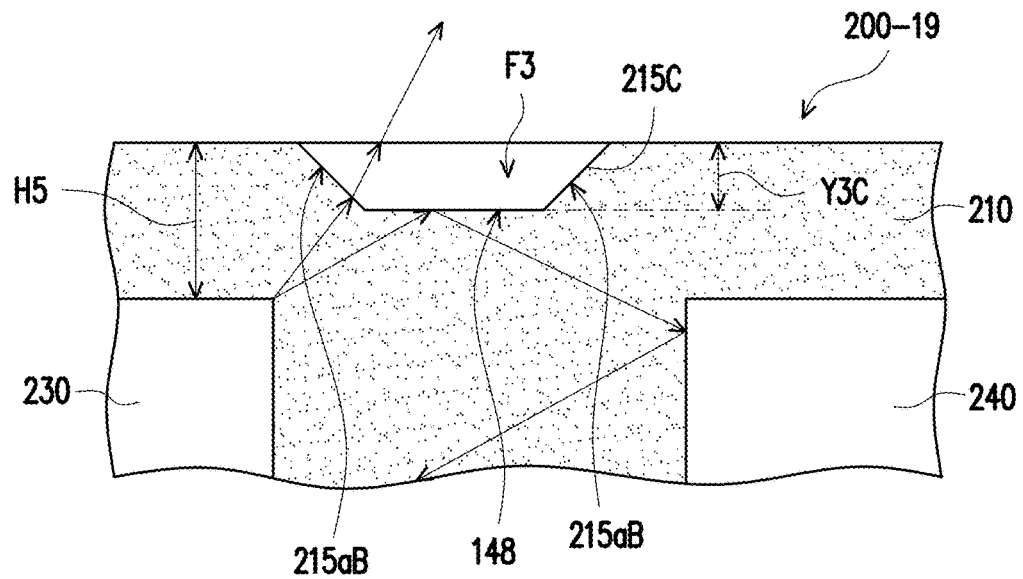
FIGS. 74A to 74B are still another two schematic cross-sectional views respectively illustrating a trench of a bio-sensing apparatus according to embodiments of the invention.
Figure 74B:
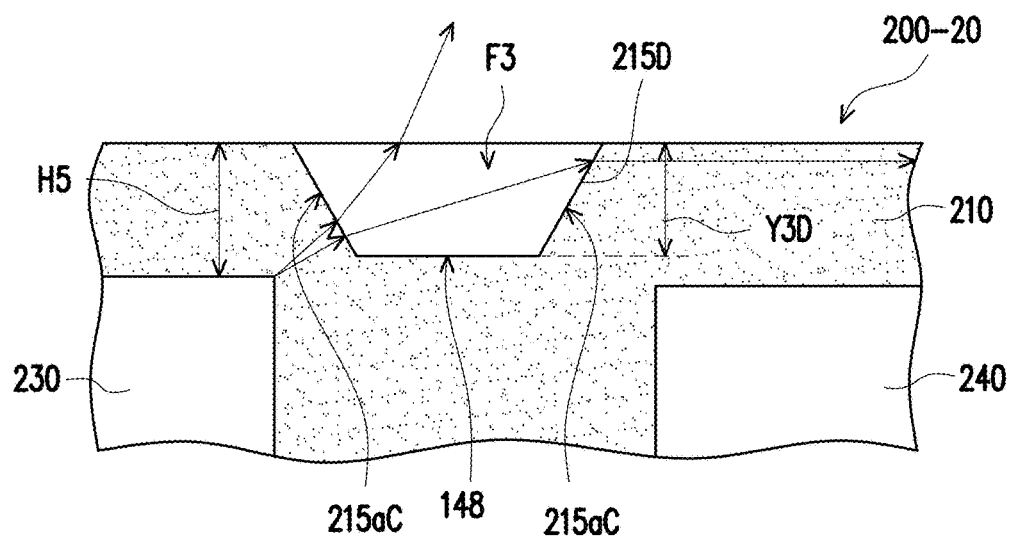

FIGS. 74A to 74B are still another two schematic cross-sectional views respectively illustrating a trench of a bio-sensing apparatus according to embodiments of the invention. Referring to FIGS. 74A and 74B, a bio-sensing apparatus 200-19 and an bio-sensing apparatus 200-20 are similar to the bio-sensing apparatus 200-12 of FIG. 68A. The main difference therebetween is described in the following. In the bio-sensing apparatuses 200-19, 200-20, 100G, trenches 215C, 215D are in shapes of inverted trapezoids. Specifically, the trench 215C (or the trench 215D) has two inclined surfaces 215aB (or two inclined surfaces 215aC) and the bottom surface 148. In the embodiments, the inverted trapezoids as the shapes of the bio-sensing apparatuses 200-19, 200-20 are inverted isosceles trapezoids. However, the invention is not limited thereto.

In addition to changing the traveling paths of the light beams through refraction, with the inclined surface 215aB (or the inclined surface 215aC) closer to the light emitting devices, the trenches in the shapes of inverted trapezoids also enable total internal reflection of the light beams transmitted to the inclined surface 215aB (or the inclined surface 215aC), so that the light beams are not directly emitted to the sensing surface of the sensing element 240. In the bio-sensing apparatuses 200-19, 200-20, depths Y3C and Y3D of the trenches 215C and 142D are less than the distance H5 from the light emitting surfaces of the respective light emitting element 230 to the surface of the light guide 210 opposite to the sensing element 240. Therefore, most of the light beams transmitted to the bottom surfaces 148 of the trenches 215C and 215D are redirected through the total internal reflection at the bottom surface and are not directly emitted to the sensing surface of the sensing element 240 (as shown in FIG. 74A).

In the embodiment, the trenches 215C and 215D are filled with a transparent material F3. In addition, a refractive index of the transparent material F3 is less than a refractive index of the light guide 210, so as to generate the total internal reflection.

Moreover, the bio-sensing apparatus 200-12-200-20 respectively include surface plasma resonance layers SPR. Functions of the surface plasma resonance layers SPR of the bio-sensing apparatuses 200-12-200-20 and a function of the surface plasma resonance layer SPR of the above bio-sensing apparatus 100 are the same, and which will not be repeated here.

Although the embodiments are already disclosed as above, these embodiments should not be construed as limitations on the scope of the invention. It will be apparent to those skilled in the art that various modifications and variations can be made to the disclosed embodiments without departing from the scope or spirit of this invention. In view of the foregoing, it is intended that the invention covers modifications and variations provided that they fall within the scope of the following claims and their equivalents.

What is claimed is:

1. A bio-sensing apparatus, adapted to sense a biopolymer, the bio-sensing apparatus comprising:
    a sensing element, having a sensing surface;
    a spatial filter element disposed on the sensing surface and comprising spatial filter sheets, wherein each of the spatial filter sheets comprising:
        a light-transmitting layer; and
        a spatial filter layer, disposed on the light-transmitting layer and having light-transmitting portions and light-blocking portions, each of the light-transmitting portions is surrounded by light-blocking portions of the light-blocking portions, wherein light-transmitting layers of the spatial filter sheets and spatial filter layers of the spatial filter sheets are stacked alternately in a normal direction of the sensing surface;
    a light-transmitting element disposed on the spatial filter element, the spatial filter element is disposed between the light-transmitting element and the sensing element; and
    a surface plasma resonance layer disposed on the light-transmitting element and adapted to receive the biopolymer, the light-transmitting element is disposed between the surface plasma resonance layer and the spatial filter element.

2. The bio-sensing apparatus as recited in claim 1, wherein the light-blocking portions and the light-transmitting portions are arranged in alternation on the sensing surface along a first direction and a second direction, the first direction is perpendicular to the second direction, and the first direction and the second direction are all perpendicular to the normal direction of the sensing surface.

3. The bio-sensing apparatus as recited in claim 2, wherein the light-blocking portions and the light-transmitting portions are arranged in a chessboard-type manner.

4. The bio-sensing apparatus as recited in claim 1, wherein the light-transmitting portions expose sensing units of the sensing element, spacing between the light-transmitting portions is S, a width of each of the light-transmitting portions is W, and $0.3\,W<S$, a thickness of a light-transmitting layer of a first spatial filter sheet of the spatial filter sheets is T1, a thickness of a light-transmitting layer of a second spatial filter sheet of the spatial filter sheets is T2, and the bio-sensing apparatus satisfies:

$$0.3 \times \frac{W}{S} \times T1 \le T2 \le T1.$$

5. The bio-sensing apparatus as recited in claim 4, wherein the bio-sensing apparatus satisfies:

$$0.3 \times \frac{W}{S} \times T1 \le T2 \le 0.9 \times \frac{W}{S} \times T1.$$

6. The bio-sensing apparatus as recited in claim 4, wherein the bio-sensing apparatus satisfies:

$$0.9 \times \frac{W}{S} \times T1 \le T2 \le T1.$$

7. The bio-sensing apparatus as recited in claim 1, wherein the spatial filter layers comprises a first spatial filter layer, a second spatial filter layer and a third spatial filter layer, the first spatial filter layer, the second spatial filter layer and the third spatial filter layer are overlapped with each other, light-transmitting portions of the first spatial filter layer comprises first light-transmitting portions, light-transmitting portions of the second spatial filter layer comprises second light-transmitting portions, light-transmitting portions of the third spatial filter layer comprises third light-transmitting portions, and the spatial filter element satisfies a condition below:
 a size of each of the third light-transmitting portions is larger than or equal to a size of each of the second light-transmitting portions, and the size of each of the second light-transmitting portions is larger than a size of each of the first light-transmitting portions; or
 the size of each of the third light-transmitting portions is larger than the size of each of the second light-transmitting portions, and the size of each of the second light-transmitting portions is larger than or equal to the size of each of the first light-transmitting portions.

8. The bio-sensing apparatus as recited in claim 7, wherein the size of each of the third light-transmitting portions is larger than the size of each of the second light-transmitting portions, the size of each of the second light-transmitting portions is larger than the size of each of the first light-transmitting portions, and the first spatial filter layer, the second spatial filter layer, and the third spatial filter layer are sequentially arranged from the sensing element towards the light-transmitting element or from the light-transmitting element towards the sensing element.

9. The bio-sensing apparatus as recited in claim 1, wherein light-transmitting portions of the spatial filter layers corresponding to one sensing unit of the sensing element are arranged along an oblique direction, the oblique direction and a normal direction of a surface of the light-transmitting element have an included angle θ, and 0°<θ<90°.

10. The bio-sensing apparatus as recited in claim 9, wherein the light-transmitting portions of a spatial filter layer are arranged at a spacing P, at least one light-transmitting portion of the spatial filter layer has a diameter K, the spatial filter layer is disposed on a light-transmitting layer, the light-transmitting layer has a thickness H, and the diameter K, the spacing P, and the thickness H satisfy:

$$\left(\frac{H}{P-D}\right) \le 0.5.$$

11. The bio-sensing apparatus as recited in claim 9, wherein light-transmitting portions of one spatial filter layer closest to the sensing element of the spatial filter layers of the spatial filter elements are respectively aligned with sensing units of the sensing element, and light-transmitting portions of the other spatial filter layers of the spatial filter element are not aligned with the sensing units of the sensing element.

12. The bio-sensing apparatus as recited in claim 1, further comprising:
 a light guide, disposed on the sensing element;
 at least one light source, disposed beside the light guide and configured to emit a light beam; and
 a reflector, disposed between the light guide and the spatial filter element, wherein the reflector has light transmitting portions, each of the light-transmitting portions of the spatial filter element overlaps at least one transmitting portion of the light transmitting portions of the reflector;
 wherein the light beam is sequentially diffused by a fingerprint of a finger and passes through the light guide, the at least one light transmitting portion of the reflector and each of light-transmitting portions of the spatial filter element to be transmitted to the sensing element.

13. The bio-sensing apparatus as recited in claim 12, wherein the reflector has at least one reflective portion disposed on the light-blocking portions of the spatial filter element.

14. The bio-sensing apparatus as recited in claim 12, wherein the light transmitting portions of the reflector are apertures of a reflective layer which overlap the light-transmitting portions of the spatial filter element respectively.

15. The bio-sensing apparatus as recited in claim 12, wherein the reflector is a reflective diffractive element.

16. The bio-sensing apparatus as recited in claim 15, wherein the light-transmitting portions of the spatial filter element are arranged in a direction, each of the light-transmitting portions has a width W1 in the direction, each of the light transmitting portions of the reflective diffractive element has a width W3 in the direction, and W3≤W1.

17. The bio-sensing apparatus as recited in claim 15, wherein the reflective diffractive element comprises:
 a light transmitting film; and
 a reflective pattern layer, disposed on the light transmitting film.

18. A bio-sensing apparatus, comprising:
 a light guide, comprising:
  a top surface; and
  a bottom surface, opposite to the top surface;
 a first reflection device, disposed on the bottom surface of the light guide;
 a light-transmitting element, disposed on the bottom surface of the light guide;
 a sensing element, disposed beside the bottom surface of the light guide;
 a light-emitting element, used to emit a light beam, wherein the light beam is reflected by the first reflection device so as to be transmitted to the sensing element; and a surface plasma resonance layer disposed on the light guide and adapted to receive the biopolymer, wherein the light guide is located between the surface plasma resonance layer and the sensing element.

19. The bio-sensing apparatus as recited in claim 18, wherein the light guide further comprising:
a light incident surface, connected between the top surface and the bottom surface, wherein an acute angle α is included between the light incident surface and the top surface.

20. The bio-sensing apparatus as recited in claim 19, wherein the acute angle α satisfies a formula (1):

$$\theta_i \le \alpha - \sin^{-1}\left(\frac{n_1}{n_2}\right), \quad (1)$$

wherein $\theta_i$ is an angle of the light beam entering the light guide through the light incident surface, $n_1$ is a refractive index of an environment medium, and $n_2$ is a refractive index of the light guide.

21. The bio-sensing apparatus as recited in claim 19, wherein the acute angle α satisfies a formula (2):

$$\theta_i \le \sin^{-1}\left\{\frac{n_2}{n_1}\sin\left[\alpha - \sin^{-1}\left(\frac{n_1}{n_2}\right)\right]\right\}, \quad (2)$$

wherein $\theta_i$ is an incident angle of the light beam entering the light incident surface, $n_1$ is a refractive index of an environment medium, and $n_2$ is a refractive index of the light guide.

22. The bio-sensing apparatus as recited in claim 18, further comprising:
a second reflection device, disposed on the bottom surface of the light guide, wherein the light beam is reflected by the first reflection device and the second reflection device so as to be transmitted to the sensing element.

23. The bio-sensing apparatus as recited in claim 18, further comprising:
a light-transmitting element, disposed on the top surface of the light guide;
a first optical adhesive, disposed between the light-transmitting element and the top surface of the light guide, and the light-transmitting element being connected to the top surface of the light guide through the first optical adhesive; and
a second optical adhesive, disposed between the bottom surface of the light guide and the sensing element, and the sensing element being connected to the bottom surface of the light guide through the second optical adhesive, wherein a material of the light guide is different to a material of the first optical adhesive and/or a material of the second optical adhesive.

24. The bio-sensing apparatus as recited in claim 23, wherein the light guide is a glass.

25. The bio-sensing apparatus as recited in claim 18, wherein the bottom surface of the light guide has a light emitting portion, and the light emitting portion has enhanced transmission microstructures, and the light beam undergoes at least one total reflection in the light guide to form a signal light beam passing through the enhanced transmission microstructure and then received by the sensing element.

26. The bio-sensing apparatus as recited in claim 25, wherein the light guide has a total reflection critical angle, and each enhanced transmission microstructure includes a light receiving area enabling an incident angle of the signal light beam to be less than the total reflection critical angle, and a back area enabling an incident angle of the signal light beam to be greater than the total reflection critical angle, and the light receiving area is greater than back area.

27. The bio-sensing apparatus as recited in claim 26, wherein each of the enhanced transmission microstructures is an asymmetrical pillar having a ridgeline, the light receiving area and a vertical reference plane passing through the ridgeline form a first angle, and the back area and the vertical reference plane form a second angle, and the first angle is greater than the second angle.

28. The bio-sensing apparatus as recited in claim 26, wherein the enhanced transmission microstructures are arranged in an array, each of the enhanced transmission microstructures is an eccentric micro-lens having a vertex, any tangent plane to the light receiving area at any point and a vertical reference plane passing through the vertex form a first angle, any tangent plane to the back area at any point and the vertical reference plane passing through the vertex form a second angle, and the first angle is greater than the second angle.

29. The bio-sensing apparatus as recited in claim 18, further comprising:
a light shielding object disposed on a substrate and located between the light-emitting element and the sensing element, wherein the first reflective element located between the light shielding object and the sensing element, and the light guide covers the sensing element, the light-emitting element, the light shielding object and the first reflective element.

30. The bio-sensing apparatus as recited in claim 18, wherein microstructures are formed on a surface of at least one of the first reflective element and the light guide.

31. The bio-sensing apparatus as recited in claim 18, wherein the first reflective element comprises light-reflecting portions arranged at an interval.

32. The bio-sensing apparatus as recited in claim 18, further comprising:
a substrate, wherein the light guide, the first reflective element, the sensing element and the light-emitting element are disposed on the substrate;
connecting lines respectively connecting between the substrate and the sensing element and between the substrate and the light-emitting element; and
a wall structure disposed on the substrate, wherein the wall structure and the substrate form an accommodation space for accommodating the light-emitting element, the sensing element and the first reflective element.

* * * * *